United States Patent
Eggers et al.

(12) 
(10) Patent No.: US 6,299,583 B1
(45) Date of Patent: Oct. 9, 2001

(54) MONITORING TOTAL CIRCULATING BLOOD VOLUME AND CARDIAC OUTPUT

(75) Inventors: Philip E. Eggers, Dublin; Eric A. Eggers, Columbus; Andrew R. Eggers, Ostrander, all of OH (US)

(73) Assignee: Cardiox Corporation, Dublin, OH (US)

( * ) Notice: Subject to any disclaimer, the term of this patent is extended or adjusted under 35 U.S.C. 154(b) by 0 days.

(21) Appl. No.: 09/361,076

(22) Filed: Jul. 26, 1999

Related U.S. Application Data

(63) Continuation-in-part of application No. 09/040,167, filed on Mar. 17, 1998, now Pat. No. 5,928,155.

(51) Int. Cl.[7] .................................................. A61B 5/028

(52) U.S. Cl. ........................... 600/526; 600/341; 600/479

(58) Field of Search ..................................... 600/322, 341, 600/342, 368, 478, 479, 481, 486, 508, 526

(56) References Cited

U.S. PATENT DOCUMENTS

| | | |
|---|---|---|
| 3,269,386 | 8/1966 | Sherman . |
| 3,304,413 | 2/1967 | Lehmann et al. . |
| 3,359,974 | 12/1967 | Khalil . |
| 3,433,935 | 3/1969 | Sherman . |
| 3,618,591 | 11/1971 | Bradley et al. . |
| 3,670,715 | 6/1972 | Perilhou et al. . |
| 3,678,922 | 7/1972 | Philips et al. . |
| 3,820,530 | 6/1974 | Gilford et al. . |

(List continued on next page.)

FOREIGN PATENT DOCUMENTS

| | | |
|---|---|---|
| 0235811 | 9/1987 | (EP) . |
| WO 88/06426 | 7/1988 | (WO) . |

OTHER PUBLICATIONS

Assadi, A. "Interaction of Planar Polymer Schottky Barrier Diodes with Gaseous Substances." *Sensors and Actuators B*, 1994; 20: 71–77.
Bachman C. "Diagnosis of Urea of Cycle Disorders." *Enzyme* 1987; 38: 233–241.
Banister EW. Cameron BJC. "Exercise—Induced Hyperammonemia: Peripheral and Central Effects." *International Journal of Sports Medicine* 1990; 11: S 129–S 142.
Batshaw ML, Brusilow SW. "Valproate–Induced Hyperammonemia." *Annals of Neurology* 1982; 11: 319–321.
Batshaw ML. "Hyperammonemia." *Current Problems in Pediatrics* 1984; 14 (11): 1–69.
Batshaw ML, Monahan PS. "Treatment of Urea Cycle Disorders." *Enzyme* 1987; 38: 242–250.
Batshaw ML. "Inborn Errors of Urea Synthesis." *Annals of Neurology* 1994; 35: 133–141.
Bessman AN, Evans JM. "The Blood Ammonia in Congestive Heart Failure." *American Heart Journal* 1955; 715–719.
Breningstall, GN. "Neurologic Syndromes in Hyperammonemic Disorders." *Pediatric Neurology* 1986; 2: 253–62.
Brockmoller J, Roots I. "Assessment of Liver Metabolic Function." *Clinical Pharmacokinetic Concepts* 1994; 27 (3): 216–248.

(List continued on next page.)

Primary Examiner—Jeffrey R. Jastrzab
(74) *Attorney, Agent, or Firm*—Mueller and Smith, LPA

(57) ABSTRACT

A system and method for measuring total circulating blood volume and cardiac output employing an analyte diffusion approach. The analyte sensor as well as the analyte-containing fluid infusion procedure may be carried out with instruments which are inserted in the bloodstream at peripheral locations of the body spaced from the heart. A controller is provided to automatically carry out these measurements as well as to provide threshold comparisons for alerting the practitioner to excursion in the parameters. The preferred analyte containing fluid is an ammoniacal fluid and the preferred sensed components is ammonia gas.

94 Claims, 37 Drawing Sheets

U.S. PATENT DOCUMENTS

| | | |
|---|---|---|
| 4,015,593 | 4/1977 | Dings et al. . |
| 4,217,910 | 8/1980 | Khalil . |
| 4,236,527 | 12/1980 | Newbower et al. . |
| 4,240,441 | 12/1980 | Khalil . |
| 4,316,391 | 2/1982 | Tickner . |
| 4,507,974 | 4/1985 | Yelderman . |
| 4,572,206 | 2/1986 | Geddes et al. . |
| 4,595,015 | 6/1986 | Jansen et al. . |
| 4,597,848 | 7/1986 | Oka et al. . |
| 4,671,295 | 6/1987 | Abrams et al. . |
| 4,682,895 | 7/1987 | Costello . |
| 4,685,470 | 8/1987 | Sekii et al. . |
| 4,722,347 | 2/1988 | Abrams et al. . |
| 4,733,669 | 3/1988 | Segal . |
| 4,785,823 | 11/1988 | Eggers et al. . |
| 4,791,935 | 12/1988 | Baudino et al. . |
| 4,807,629 | 2/1989 | Baudino et al. . |
| 4,819,655 | 4/1989 | Webler . |
| 4,841,981 | 6/1989 | Tanabe et al. . |
| 4,869,263 | 9/1989 | Segal et al. . |
| 4,949,724 | 8/1990 | Mahutte et al. . |
| 5,046,505 | 9/1991 | Sekii et al. . |
| 5,088,491 | 2/1992 | Schaldach . |
| 5,092,339 | 3/1992 | Geddes et al. . |
| 5,383,468 | 1/1995 | Nakayama et al. . |
| 5,395,505 | 3/1995 | Band et al. . |
| 5,413,592 | 5/1995 | Schroeppel . |
| 5,435,308 | 7/1995 | Gallup et al. . |
| 5,443,074 | 8/1995 | Roelandt et al. . |
| 5,453,248 | 9/1995 | Olstein . |
| 5,458,128 | 10/1995 | Polanyi et al. . |
| 5,464,434 | 11/1995 | Alt . |
| 5,536,783 | 7/1996 | Olstein et al. . |
| 5,607,644 | 3/1997 | Olstein et al. . |
| 5,611,338 | 3/1997 | Gallup et al. . |
| 5,647,359 | 7/1997 | Kohno et al. . |
| 5,928,155 * | 7/1999 | Eggers et al. .......................... 600/526 |

OTHER PUBLICATIONS

Brusilow SW, Batshaw ML, Waber L. "Neonatal Hyperammonemic Coma." *Advances in Pediatrics* 1982; 29: 69–103.

Brusilow, SW, Danney, M, Waber, LJ, et al. "Treatment of Episodic Hyperammonemia in Children with Inborn Errors of Urea Synthesis." *The New England Journal of Medicine* 1984; 310: 1630–1634.

Burtis CA, Ashwood ER (eds). *Teitz Textbook of Clinical Chemistry* (second edition). Philadelphia: W.B. Saunders Company, 1994. pp. 1487–1489.

Burton, B.K. Abstract of "Inborn Errors of Metabolism in Infancy: A Guide to Diagnosis." *Pediatrics* 1998; 102(6).

Canzanello VJ, Rasmussen RT, McGoldrick MD. "Hyperammonemic Encephalopathy During Hemodialysis." *Annals of Internal Medicine* 1983; 99 (2): 190–191.

Cha, GS. Liu, D, Meyerhoff, ME, et al. "Electrochemical Performance, Biocompatibility, and Adhesion of New Polymer Matrices for Solid–State Ion Sensor." *Analytical Chemsitry* 1991; 63(17): 1666–1672.

Chaves–Carbollo, E. "Detection of Inherited Neurometabolic Disorders." *Pediatric Neruology* 1992; 39 (4): 801–820.

Ciana, LD, Caputo, G. "Robust, reliable biosensor for continuous monitoring of urea during dialysis." *Clinical Chemistry* 1996; 47 (7): 1079–1085.

Clark, LC, Lyons, C. "Electrode Systems for Continuous Monitoring in Cardiovascular Surgery." Annals New York Academy of Sciences. 1962 pp. 29–45.

Cunningham, FG, McDonald, PC, Gant, NF, Williams *Obstertrics*. Appleton & Lange Norwalk: 1989.

Diamond DA, Blight A, Ransley PG. "Hyperammonemic Encephalopathy: A Complication Associated with the Prune Belly Syndrome." *Journal of Urology* 1989; 142: 361–362.

Duarte J, Macias S, Coria F, Fernandez E, Claveria LE. "Valproate–Induced Coma: Case Report and Literature Review." *Annals of Pharmacotherapy* 1993; 27: 582–583.

Evans J, et al. "Altered Liver Function of Chronic Congestion Heart Failure." *American Journal of Medicine* 1952; 13: 704–712.

Ferenci, P, Herneth, A, Steindl, P. "Newer Approaches to Therapy of Hepatic Encephalopathy." *Seminars in Liver Disease*. 1996; 16 (3): 329–338.

Fonseca–Wollheim F. "The influence of pH an various anions on the distribution of $NH_4+$ in human blood." *European Journal of Clinical Chemistry and Clinical Biochemistry* 1995; 33 (5): 289–294.

Fricker R, Doptis P, Hornak M, Li C. "Development of and optimized ammonia assay for the Kodak Ektachem Analyzer." *Clinical Chemistry* 1990; 36 (6): 1072.

Furst, P, Josephson, B, et al. "Nitrogen Balance after Intravenous and Oral Administration of Ammonium Salts to Man." *J. Appl. Physiol.* 1969; 26(1): 13–22.

Gowenlock AH, McMurray JR, McLaughlan DM (eds). *Varley's Pratical Clinical Biochemistry* (sixth edition). Boca Raton: CRC Press, Inc., 1988. pp. 742–749.

Green A. "When and how should we measure plasma ammonia?" *Clinical Biochemistry* 1988; 25: 199–209.

Hindfelt, B. "The Distribution of Ammonia between Extracellular and Intracellular Compartments of the Rat Brain." *Clinical Science and Molecular Medicine* 1975; 48: 33–37.

Hsia YE. "Inherited Hyperammonemic Syndromes." *Gastroenteroloy* 1974; 67: 347–374.

Huizenga JR, Tangerman A, Gips CH. "A Rapid Method for Blood Ammonia Determination Using the New Blood Ammonia Checker (BAC) II." *Clinica Chimica Acta* 1992; 210: 153–155.

Imler M, Frick A, Schliener JL, Stahl A. "An Automated Microassay for Blood Ammonia." *Journal Clinical Chemistry and Clinical Biochemistry* 1979; 17: 247–250.

Iosefoshn M, Hicks JM. "Ektachem Multilayer Dry–Film Assay for Ammonia Evaluated." *Clinical Chemistry* 1985; 31 (12): 2012–2014.

Jacquez, JA, Poppell, JW, Jeltsch, R. "Solubility of ammonia in human plasma." *Journal of Applied Physiology*. 1959; 14(2): 255–258.

Jurgens, P. "New Aspects on Etiology, Biochemistry and Therapy of Portal Systemic Encephalopathy: A critical Survey." *Nutrition* 1997; 13: 560–570.

Kasal C. "Agent Ammonia: A New Total Liquid Assay System for Blood Ammonia Levels for the Abbott Spectrum." *Clinical Chemistry* 1988; 34 (6): 1188–1189.

Kotin P, et al. "Cardiac or congestive cirrhosis of the liver." *American Journal of Pathology* 195 1; 27: 561–570.

Kubasik NP, Lisuzzo CW, Same DG, et al. "Multilayered film analysis: Evaluation of ammonia and creatinine slides." *Clinical Biochemsitry* 1984; 17: 15–18.

Lahdesmaki, I, Lewenstam, A., Ivaska, A. "A polyprrole–based Amperometric Ammonia Sensor." *Talanta* 1996; 43: 125–134.

Lamiell JJ, Ducey JP, Freesekepczyk BJ, Musio FO, Hansberry Kl. "Essential amino acidinduced adult hyperammonemic encephalopathy and hypophosphatemia." *Critical Care Medicine* 1990; 18 (4): 451–452.

Leonard JV. "Hyperammonemia in childhood." In: Clayton BE, ed. *Chemical Pathology and the Sick Child*. Oxford: Blackwell, 1984: 96–119.

Leevy, CM, Leevy, CB, Howard, MM. "Indocyanine Green and the Liver." *Problems in Liver Diseases*. Stratton Intercontinental Medical Book Corporation. New York: 1977.

Lockwood, AH, McDonald, JM, etal. "The Dynamics of Ammonia Metabolism in Man." *Clin. Invest.* 1979; 63:449–460.

Martin, WJ, Matzke, GR. "Treating Severe Metabolic Alkalosis." *Clinical Pharmacology* 1982; 1: 42–48.

Msall M, Batshaw ML, Suss R, Brusilow SW, Mellits ED. "Neurologic Outcome in Children with Inborn Errors of Urea Synthesis: Outcome of Urea–Cycle Enzymopathies." *New England Journal of Medicine* 1984; 310: 1500–1505.

Nelson, RM, Seligson, D. "Studies on Blood Ammonia in Normal and Shock States." *Surgery*. 34(1): 1–8.

Oster J, et al. "Exacerbation of Hepatic Encephalopathy by Chronic Renal Failure." *Clinical Nephrology*1978; 9: 254–257.

Ozand PT, Gascon GG. "Organic Acidurias: A Review Part 2." *Journal of Child Neurology* 1991; 6: 288–303.

Queres, JC. "Hyperammonemia and *Helicobacter pylori*." *The Lancet* 1995; 346–713.

Quiles R, Fernandez–Romero JM, Fernandez E, De Castro MDL. "Continuous flow assay of ammonia in plasma using immobilized enzymes." *Analytica Chimica Acta* 1994; 294 (1): 43–47.

Ratnaike RN, Buttery JE, Hoffman S. "Blood Ammonia Measurement Using a Simple Reflectometer." *Journal of Clinical Chemistry and Clinical Biochemistry* 1984; 22(1): 105–108.

Russell, A. The Implications of Hyperammonemia in Rare and Common Diseases, Including Migraine.

Ryder KW, Olson JF, Kahnoski S. "Hyperammonemia After Transurethral Resection of the Prostate: A Report of 2 Cases." *Journal of Urology*1984; 132: 995–997.

Tanner, RL. "Ammonia Metabolism." *American Journal of Physiology*1978; 235(4) F265–F277.

Thomas DW, Sinatra FR, Hack SL, Smith TM, Platzker ZCG, Merritt RJ. "Hyperammonemia in Neonates Receiving Intravenous Nutrition." *Journal of Parenteral and Enteral Nutrition* 1982; 6 (6): 503–506.

Van Thiel, DH. "Assesment of Liver Function: The Current Situation" *J. Okla. State Med. Assoc.* 1995; 88: 11–16.

Vellekoop, MJ, Lubking, GW, et al. "Intergrated–circuit–compatible Design and Technology of Acoustic–wave–based Mircosensors." *Sensors and Actuators A*1994; 44: 249–263.

Walser M, Stewart PM. "Organic Acidaemia and Hyperammonemia: Review." *Journal of Inherited and Metabolic Disease* 198 1; 4 (4): 177–182.

Wilkerson, JE, Batterton, DL, Horvath, SM. "Excercise–Induced Changes in Blood Ammonia Levels in Humans." *European Journal of Applied Physiology*. 1977; 37: 255–263.

Wilson, BE, et al. "Rapidly Fatal Hyperammonemic Coma in Adults—Urea cycle enzyme deficiency." *West J. Med.* 1994; 161: 166–168.

Yang, VC, Ma, S, et al. "A Novel Electrochemical Heparin Sensor." *ASAIO Journal* 1993; 39: M195–M201.

Yoshida EM, Ostrow DN, Erb SR, Fradet G. "Hyperammonemia After Heart–Lung Transplantation." *Gastroenterology* 1997; 112 (6): 2162.

Zhang, SF, "Evaluation of fluorescent dyes for in vitro pH measurement." *Med. & Biol., Eng. & Comput.* 1994, 32: 224–227.

Astiz ME, Galera–Santiago A, Rackow EC. "Intravascular volume and fluid therapy for severe sepsis." *New Horizons* 1993; 1 (1): 127–136.

Baek SM, Makabali G. Byron–Brown CW, Kusek JM, Shoemaker WC. "Plasma expansion in surgical patients with high central venous pressure: the relationship of blood volume to hematocrit, CVP, pulmonary wedge pressure, and cardiorespiratory changes." *Surgery* 1975; 78: 304–315.

Beard EF, Nicholson JW, Wood EH. "Application of an ear oximeter for estimation of cardiac output by the dye method in man." *Journal of Laboratory and Clinical Medicine* 1950; 36: 798.

Besa EC. "Physiological Changes in Blood Volume."*CRC Critical Reviews in Clinical Laboratory Science* 1975; : 67–79.

Bickell WH, Bruttig SP, Millnamow GA, O'Bener J, Wade CE. "The detrimental effect of intravenous crystalloid after aortotomy in swine." *Surgery*199 1; 110: 529–536.

Bone RC. "The pathogenesis of sepsis." *Annals of Internal Medicine* 199 1; 115:457–459.

Bradley EC, Barr JW. "Determination of Blood Volume Using Indocyanine Green (Cardio–Green) Dye." *Life Sciences* 1968; 7 (1): 1001–1007.

Brown E, Hopper J, Hodges JL, Bradley B, Wennesland R, Yarnauchi H. "Red Cell, Plasma, and Blood Volume in Healthy Women Measured by Radiochromium Cell–Labeling and Hematocrit." *Journal of Clinical Investigation* 1962; 12: 2182–2190.

Burge CM, Skinner SL. "Determination of hemoglonbin mass and blood volume with CO: evaluation and application of a method." *Journal of Applied Physiology* 1995; 79 (2): 623–631.

Busse MW, Zisowsky S, Henschen S, Panning B, Reilmann L. "Determination of circulating blood volume by measurement of indocyanine green dye in hemolysate: A preliminary study." *Life Science* 1990; 46: 647–652.

Cade, R. et al. "Hepatorenal Syndrome." *American Journal of Medicine* 1987; 82: 427–438.

Christensen P, Eriksen B, Hennenberg SW. "Precison of a new bedside method for estimation of the circulating blood volume." *Acta Anaesthesiologica Sandinavica* 193; 7: 622–627.

Clancy MJ, Alderman J, Case C, Taylor KJW. "The use of ultrasound in the non–invasive detection of changes in the renal circulation in response to blood loss using an animal model." *Resuscitation* 1995; 30: 161–167.

Cunningham FG, et al. Gant NF: Williams Obstetrics. 18th edition, Norwalk, Connecticut, Appleton & Lange, 1989.

Dagher FJ, Lyons JH, Finlayson DC, Shamsai J, Moore FD. Blood Volume Measurement: A Critical Study. Prediction of Normal Values: Controlled Measurement of Sequential Changes: Choice of a Bedside Method. *Advances in Surgery* 1969; 1: 69–109.

Dahn MS, Lange MP, Wilson RF, Jacobs LA, Mitchell RA. "Hepatic blood flow and splanchnic oxygen consumption measurements in clinical sepsis." *Surgery* 1990; 107: 295–301.

Dawidson I, Ottosson J, Reich J. "Infusion volumes of Ringer's lactate and 3% albumin solution as they relate to survival after resuscitation of a lethal intestinal ischernic shock." *Cir. Shock* 1986; 18: 277.

Davison, AM. "Hepatorenal failure." *Nephrol. Dialysis Transplantation* 1966; 11(8): 24–31.

Fairbanks VF, Klee GG, Wiseman GA, Hoyer JD, Terreri A, Petitt RM, Silverstein MN, "Measurement of Blood Volume and Red Cell Mass: Re–examination of $^{51}Cr$ and 1251Methods." *Blood Cells, Molecules, and Diseases* 1996;22 (15): 169–186.

Fukui M, Shigemi K. "Determination of single and repeated red cell volumes by the indicator dilution method using carbon monoxide as the indicator." *Critical Care Medicine* 1989; 17 (11): 1119–1202.

Gattinoni L, Brazzi L, Pelosi P, Latini R, Tognoni G, Pesenti A, et al. "A trial of goal–oriented hemodynamic therapy in critically ill patients." Sv02 Collaborative Group. *New Enlgand Journal of Medicine* 1995; 333: 1025–1032.

Gehring H, Nahm W, Klotz KF, Zais 0, Schreiber R, Schuren P, Schmucker P. "Plasmavolumenbestimmung mit dern Farbstoff ICG bei Anderung des intravasalen" *Volumens. Infusionther Transfusionsmed* 1996; 23: 86–91.

Gibson JG, Peacock WC, Seligman AM, Sack T. "Circulating red cell volume measured simultaneiusly by the radioactive iron and dye methods." *Journal of Clinical Investigation* 1946; 25: 838–847.

Godje 0, Peyerl M, Seebauer T, Dewald 0, Reichart B. "Reproducibiltiy of Double Indicator Dilution Measurement of Intrathoracic Blood Volume Compartments, Extravascular Lung Water, and Liver Function." *Chest* 1988; 113: 1070–1077.

Golper TA, Walczyk M. "Treatment of the overhydrated patient in the intensive care unit." Balliere's Clinical Anesthesiology 1988; 2 (3): 729–756.

Gray SJ, Frank H. "The simultaneous determination of red cell mass and plasma volume with radioactive sodium chromate and chromic chloride." *Journal of Clinical Investigation* 1953; 32: 1000–1004.

Grehant M, Quinquard E. "Mesures du volume du snag contenu dans L'organisme d'un mammifere vivant." *C.R. Acad. Sci. Paris* 1882; 94: 1450.

Hahn PF, Balfour WM, Ross JF, Bale WF, Whipple GH. "Red cell volume circulating and total as determined by radio ion." *Science* 1941; 93:87.

Haljamae H. "The pathophysiology of shock." *Acta Anesthesiology Scand. Suppl.* 1993; 98: 3–6.

Hankins G., et al. Critical Medicine and the Obstetric Patient. Textbook of Critical Care Medicine 1995; Chap. 8: WC Shoemaker, et al. Editors, WB Saunders Company, Philadelphia.

Hayes MA, Timmins AC, Yau EH, Palazzo M, Hinds CJ, Watson D. "Elevation of systemic oxygen delivery in the treatment of critically ill patients." *New England Journal of Medicine* 1993; 330: 1717–1722.

Henschen S, Busse MW, Zisowasky S, Panning B. "Determination of Plasma Volume and Total Blood Volume Using Indocyanine Green: A Short Review." *Journal of Medicine* 1993; 24 (1): 1027.

Hill DM, Warren SE, Mitas JA, Swerflin AHR. "Hepatic coma after open heart surgery." *South Med Journal* 1980; 73:906–911.

Holmes MA, Weiskopf B. "Determination of plamsa volume in swine by the enzyme–dilution method." *American Journal of Physiology* 1987; 2 1: R 1003–R 1008.

Horton JW, Burnweit CA. "Hemodynamic function in acute pancreatitis." *Surgery* 1988; 103 (5): 538–546.

Iijima T, Aoyagi T, Iwao Y, Masuda J, Fuse M, Kobayashi N, Sankawa H. "Cardiac Output and Circulating Blood Volume Analysis by Pulse Dye–Densitometry." *Journal of Clinical Monitoring* 1997; 13: 81–89.*

Johner C, Chamney PW, Schneditz D, Kramer M. "Evaluation of an ultrasound volume monitor." *Nephrology Dialysis Transplantation* 1988; 13: 2098–2103.*

Kisch H, Leucht S, Lichtarck–Aschoff M, Pfeiffer UJ. "Accuracy and reproducibility of the measurement of actively circulating blood volume with an integrated fiberoptic monitoring system." *Critical Care Medicine* 1995; 23 (5): 885–893.*

Kivik P. "Relationship between hemodynamics and blood volume changes after cardiopulmonary bypass during coronary artery bypass grafting." *European Journal of Cardiothoracic Surgery* 1993; 7 (5): 231–234.*

Kleinknecht D, Pallot JL. "Epidemiology and prognosis of acute renal insufficiency in 1997." *Recent data. Nephrologie* 1998; 19 (2): 49–55.*

Krafft P, Fridrich P, Pernerstorfer T, Fitzgerald RD, Koe D, et al. "The acute respiratory distress syndrome: definitions, severity and clinical outcome." *Intensive Care Medicine* 1996; 22: 519–529.*

Kudo T, Suzuki S, Iwabuchi T. "Importance of monitoring the circulating blood volume in patients with cerebral vasospasm after subarachnoid hemorrhage." *Neurosurgery* 198 1; 9 (5): 5 14–520.*

Lang CH, Bagby GJ, Ferguson JL, Spitzer JJ. "Cardiac output and redistribution of organ blood flow in hypermetabolic sepsis." *American Journal of Physiology* 1984; 246: R3 3 1–R3 37.*

Lee LM, Gumowski J. "Adrenocortical insufficiency: a medical emergency." *AACN Clinical Issues Critical Care Nurses* 1992; 3 (2): 319–330.*

Leevy CM, Leevy CB, Howard MM. Indocyanine Green and the Liver. In Problems in Liver Disease (ed Davidson CS). New York: Stratton Intercontinental Medical Book Corporation, pp. 42–52.*

Liepert DJ, Rosenthal MH, Thomas SJ. "Shock: A comparative physiologic approach to mechanisms and therapy." *Seminars in Anesthesia* 1999; 18 (1): 1–14.*

Little RA, Gorman D, Allgower M. Shock index revisited. In: J.L. Vincent (ed), Update to Intensive Care and Emergency Medicine 10. Update 1990. New York: Springer, 1990; 505–512.

Lucas CE, Ledgerwood AM, Shier MR, Bradley VE. "The renal factor in the post traumatic 'fluid overload' syndrome." *Journal of Trauma* 1977; 17 (9): 667–676.

Miyahara A, Ohkawa H, Ishihara H, Matsuki A. "Changes in the Initial Distribution Volume of Glucose and Plasma Volume Following Volume Challenge in Dogs." *Infusionsther Transfusionsmed* 1995; 22: 274–279.

Mythen MG, Webb AR. Perioperative "Plasma Volume Expansion Reduces the Incidence of Gut Mucosal Hypoperfusion During Cardiac Surgery." *Archives of Surgery* 1995; 130: 423429.

Nomof N, Hopper J, Brown E, Scott K, Wennesland R. "Simultaneous determination of the total volume of red blood cells by use of carbon monoxide and chromium51 in health and diseased subjects." *Journal of Clinical Investigation* 1954; 33: 1382–1387.

Pacheco A, Martins C, Kreimeier U, Frey L, Messmer K. "Hypertonic volume therapy: feasibility in the prevention and treatment of multiple organ failure and sepsis." *Rev. Paul Med* 1995; 113 (6): 1053–1060.

Posen S, Clubb JS, Neale FC, Hotchkis D. "The measurement of plasma volume by enzyme dilution." *Journal of Laboratory and Clinical Medicine* 1965; 65: 530–538.

Ritz E. "Diuretics in renal failure." *Wien Med Wochenshcr* 1996; 146 (16): 443–446.

Robert JH, Toledano AE, Toth LS, Premus G, Dreiling DA. "Hypovolemic shock, pancreatic blood flow, and pancreatitis." *International Journal of Pancreatology* 1988; 3(4): 283–292.

Rockel A, Abdelhan–lid S, Fiegel P, Menth M, Walb D, Schneditz D. "Characterization of refilling types by continuous blood volume monitoring during hemodialysis." *Kidney International Supplement* 1993; 41: S67–S69.

Roob JM, Schneditz D, Haas GM, Horina JH, Pogglitsch H. "Continuous registration of blood volume changes during haemodialysis by ultrasonic measurement." *Wochenschrift* 1990; 102 (5).

Santoro A, Mancini E, Paolini F, Cavicchibli G, Bosetto A, Zuccelli P. "Blood volume regulation during hemodialysis." *American Journal of Kidney Disease* 1998; 32 (5): 739–748.

Santoro, A, Mancini, E, Padini F, Zucchelli, P. "Blood Volume Monitoring And Control." Neophrol. Dial Transplant 1996; 11 (Supp 2): 42–47.

Schad H, Haider M, Brechtelsbauer H. "Determination of plasma volume with indocyanine green." *Anaesthetist* 1987; 36: 608–614.

Shier MR, Bradley VE, Ledgerwood AM, et al. "Renal function and the postresuccitative hypertension syndrome." *Surgical Forum* 1975; 26: 56–58. 131–135.

Shimodate Y, Koh H, et al. "Comparison of glucose and sucrose as an indicator for dilution volumetry in haernorrhagic shock." *European Journal of Anesthesiology* 1995; 12: 397–401.

Shippy CR, Appel PL, Shoemaker WC. "Reliability of clinical monitoring to assess blood volume in critically ill patients." *Critical Care Medicine* 1984; 12: 107.

Shirani KZ, Vaughan GM, Mason AD, Pruitt BA. "Update on current therapeutic approaches in burns." *Shock* 1996; 5 (1): 4–16.

Shoemaker W, Bryan–Brown C, Quigley L, et al. "Body fluid shifts in depletion and post stress and their correction with adequate nutrition." *Surgical Gynecology and Obstetrics* 1973; 136: 371–374.

Shoemaker WC, Schluchter M, Hopkins JA, Appel PL, Schwartz S, Chang P. "Fluid therapy in emergency resuscitation: Clinical evaluation of colloid and crystalloid regimens." *Critical Care Medicine* 198 1; 9: 367–368.

Shoemaker WC, Appel PL, Kram HB. "Tissue oxygen debt as a determinant of lethal and nonlethal postoperative organ failure." *Critical Care Medicine* 1988; 16: 1117–1120.

Shoemaker WC, Appel PL, Bishop MH, Hardin E. "Temporal Blood Volume, Hemodynamic and Oxygen Transport Patterns in ARDS," *Critical Care Medicine* 1994: A86.

Silbergleit R, Satz W, McNamara RM, Lee DC, Schoffstall JM. "A new model of uncontrolled hemorrahage that allows correlation of blood pressure and hemorrhage." *Academic Emergency Medicine* 1996; 3 (10): 917–921.

Sivan Y, et al. "Acute Hepatic Failure after Open–heart Surgery in Children." *Pediatr. Cardiol* 1987; 8: 127–130.

Sterling K, Gray SJ. "Determination of the circulating red cell volume in man by radioactive chromium." *Journal of Clinical Investigation* 1950; 29: 1614–1619.

Steuer RR, Germain MJ, Leypoldt JK, Cheung AK. "Enhanced fluid removal guided by blood volume monitoring during chronic hemodialysis." *Artificial Organs* 1988; 22 (8): 627–632.

Stiller S, Schallenberg U, Gladziwa U, Ernst E, Mann H. "Short time dialysis with continuous blood volume control." *International Journal of Artificial Organs* 1990; 13: 83–86.

Tollofsrud S, Noddeland H. "Hypertonic saline and destran after coronary artery surgery mobilizes fluid excess and improves cardiorespiratory functions." *Acta Anesthesiology Scand.* 1998; 42 (2): 154–161.

Tschaikowsky K, Meisner M, Durst R, Rugheimer E. "Blood volume determination using hydroxyethyl starch: A rapid and simple intravenous injection method." *Critical Care Medicine* 1997; 25 (4): 599–606.

Trunkey D. "Trauma." *Scientific American* 1983; 249: 28–35.

Veillon C, Patterson KY, Nagey DA, Tehan AM. "Measurement of Blood Volume with an Enriched Stable Isotope of Chromium (53Cr) and Isotope Dilution by Combined Gas Chromotography–Mass Spectrometry." *Clinical Chemistry* 1994; 40 (1); 71–73.

Wagner DL. "Shock in the operating room." *American Journal of Emergency Medicine* 1984; 2 (1): 92–99.

Wallin CJ. "Indicator dilution measurement of lung water: Considerations of the method." *Acta Anaesthesiologica Scandinavica* 1998; 42 (3): 383.

Wang P, Zhou M, Rana MW, Ba ZF, Chaudry IH. "Differential alterations in microvascular perfusions in various organs during early and late sepsis." *American Journal of Physiology* 1992; 263: G38–G43.

Wang P, Ba Z, Talt SM, Zhou M, Chaudry IH. "Alterations in Circulating Blood Volume During Polymicrobial Sepsis." *Circulatory Shock* 1993; 40: 92–98.

Wangensteen SL, Eddy DM, Ludewig RM. "The hydrodynamics of arterial hemorrhage." *Surgery* 1968; 64: 912–921.

Warden GD. "Burn shock resuscitation." *World Journal of Surgery* 1992; 16 (1): 16–23.

Welsby I, Mythen M. "Plasma volume support in cardiac surgery." *Baillere's Clinical Anesthesiology* 1997; 11 (1): 105–125.

Wennesland R, Brown E, Hopper J, et al. "Red cell, plasma, and blood volume in healthy men measured by radiochromium (Cr51) cell tagging and hematocrit: Influence of age somatotype and habits of physical activity on the variance after regression of values to height and weight combined." *Journal of Clinical Investigation* 1959; 38: 1065–1077.

Zhang B, Huang YH, Chen Y, Yang Y, Hao ZL, Xie SL. "Plasma tumor necrosis factor–alpha, its soluble receptors and interleukin—I beta levels in critically burned patients." *Burns* 1998; 24 (7): 599–603.

Abrams, JH, Weber, RE, et al. "Transtracheal Doppler: A New Procedure for Continuous Cardiac Output Measurement." *Anesthesiology* 1989 70: 134–138.

Afonso, S, Rowe, GG, et al. "Intravascular and Intracardiac Blood Temperatures in Man." *J. Appl. Phisiol.* 17(4): 706–708.

Assadi, A., Spetz, A., et al. "Interaction of Planar Polymer Schottky Barrier Diodes with Gaseous Substances." *Sensors and Actuators* B 1994; B 71–77.

Cass, AE, Davis, G. "Ferrocene–Mediated Enzyme Electrode for Amperometric Determination of Glucose." *Anal. Chem.* 1964; 56: 667–671.

Cha, GS, Liu, D. et al. "Electrochemical Performance, Biocompatibility, and Adhesion of New Polymer Matrices for Solid–State Ion Sensors." *Anal. Chem.* 1991; 63: 1666–1672.

Clark, LC, Lyons, C. "Electrode Systems for Continuous Monitoring in Cardiovascular Surgery." Annals of NY Academy of Surgery 1962 pp. 29–45.

Furst, P, Josephson, B, et al. "Nitrogen Balance after Intravenous and Oral administration of Ammonium Salts to Man." *J. Appl. Physiol.* 1969; 26(1): 13–22.

Ganz, W, Donoso, CS, et al. "A New Technique for Measurement of Cardiac Output in Thermodilution by Man." *The American Journal of Cardiology* 1971; 27: 392–396.

Green, A. "When and How Should We Measure Plasma Ammnonia?" *Clin. Biochem* 1988; 25: 199–209.

Lahdesmaki, I. Lewenstam, A, et al. "A Propyrrole–based Amperometric Ammonia Sensor." *Talanta* 1996; 43: 125–134.

Lockwood, AH, McDonald, JM, et al. "The Dynamics of Ammonia Metabolism in Man." *J. Clin. Invest.* 1979 63: 449–460.

Moore, FA, Haenel, JB, et al. "Alternatives to Swan–Ganz Cardiac Output Monitoring." *Surgical Critical Care* 1991; 71(4): 699–721.

Schreuder, JJ, Jansen, JR, et al. "Continuous Output Monitoring During Cardiac Surgery." Update in Intensive Care and Emergency. Ed. J.L. Vincent. New York: Springer–Versky, 1990 pp. 413–416.

Schweiss, ed., *Continuous Measurement of Blood Oxygen Saturation in the High Risk Patient* San Diego: Beach International, Inc. 1983.

Segal, J, Pearl, RG, et al. "Instantaneous and Continuous Cardiac Output Obtained with a Doppler Pulmonary Artery Catheter." *JACC* 1989; 13(6): 1382–1392.

Vellekoop, MJ, Lubking, GW, et al. "Integrated–circuit––compatible Design and Technology of Acoustic–wave––based microsensors." *Sensors and Actuators* A 1994 44: 249–263.

\* cited by examiner

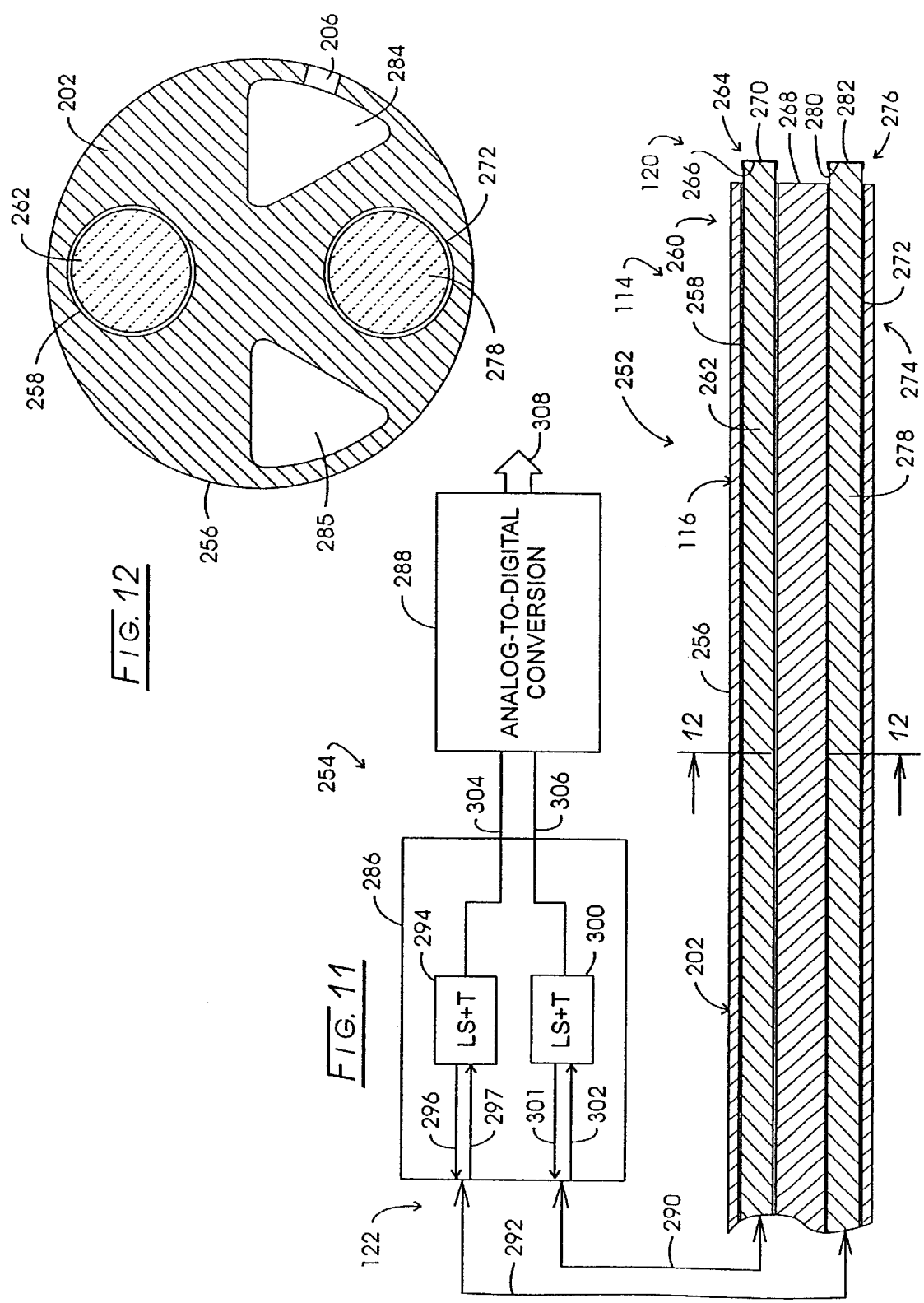

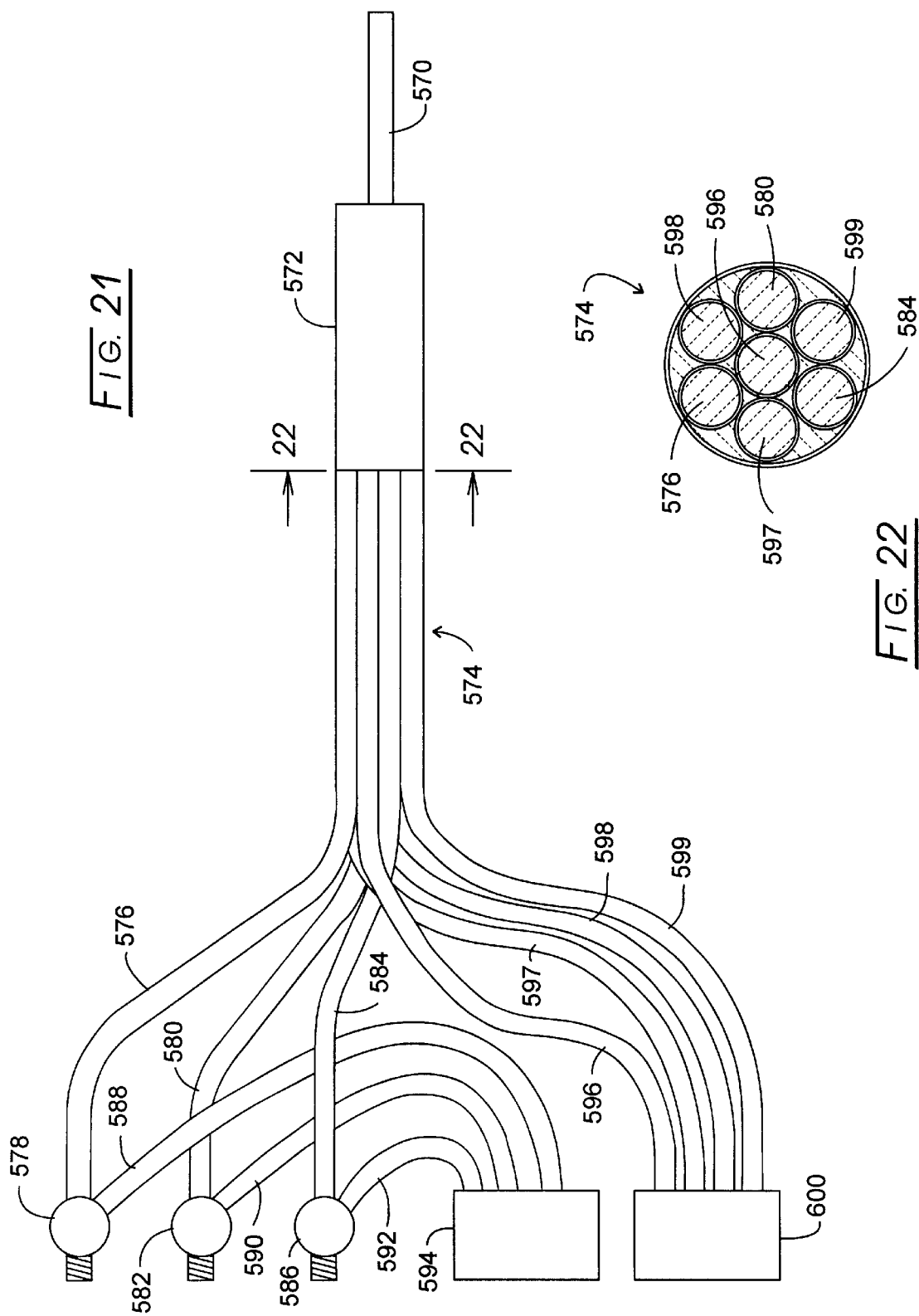

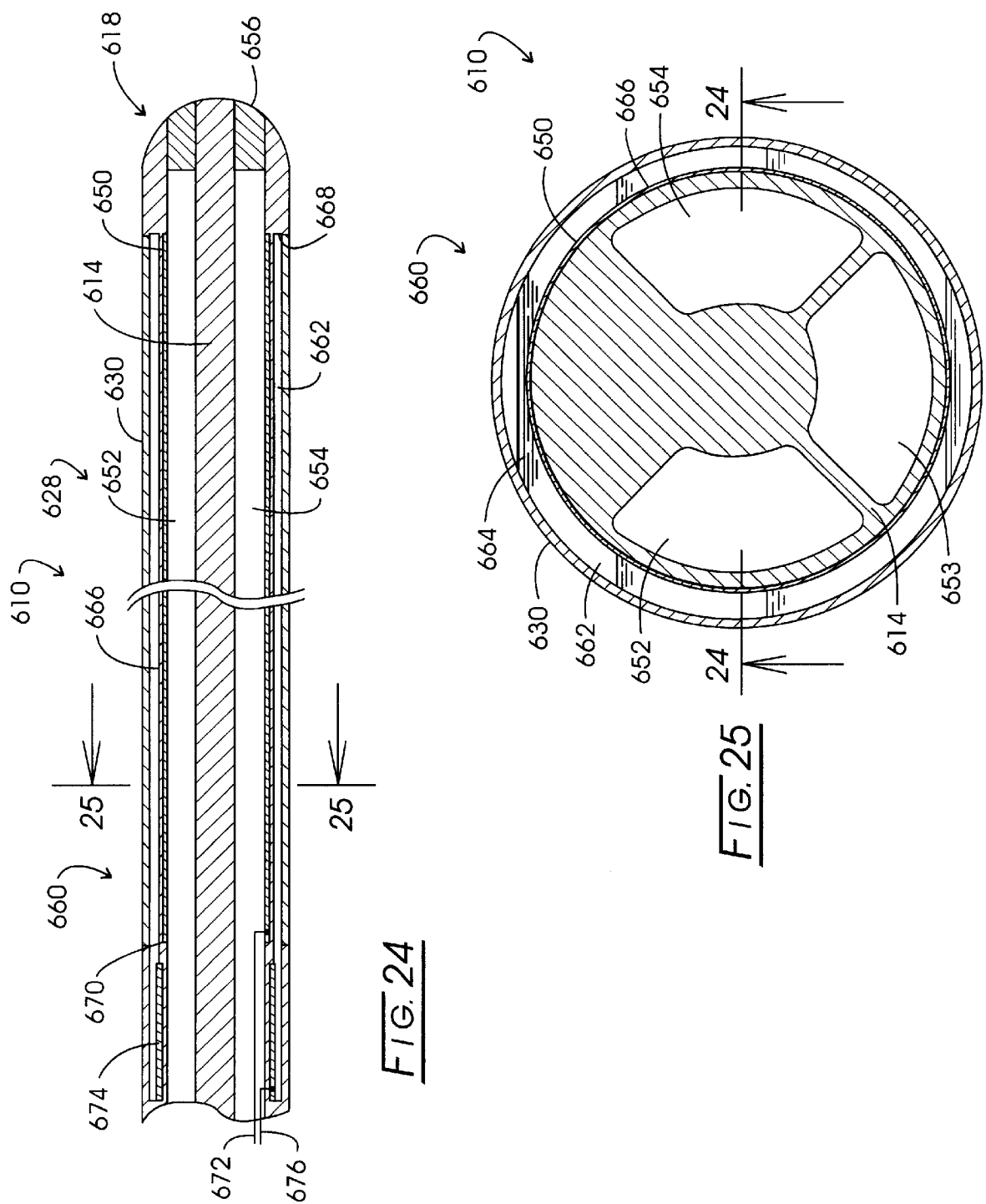

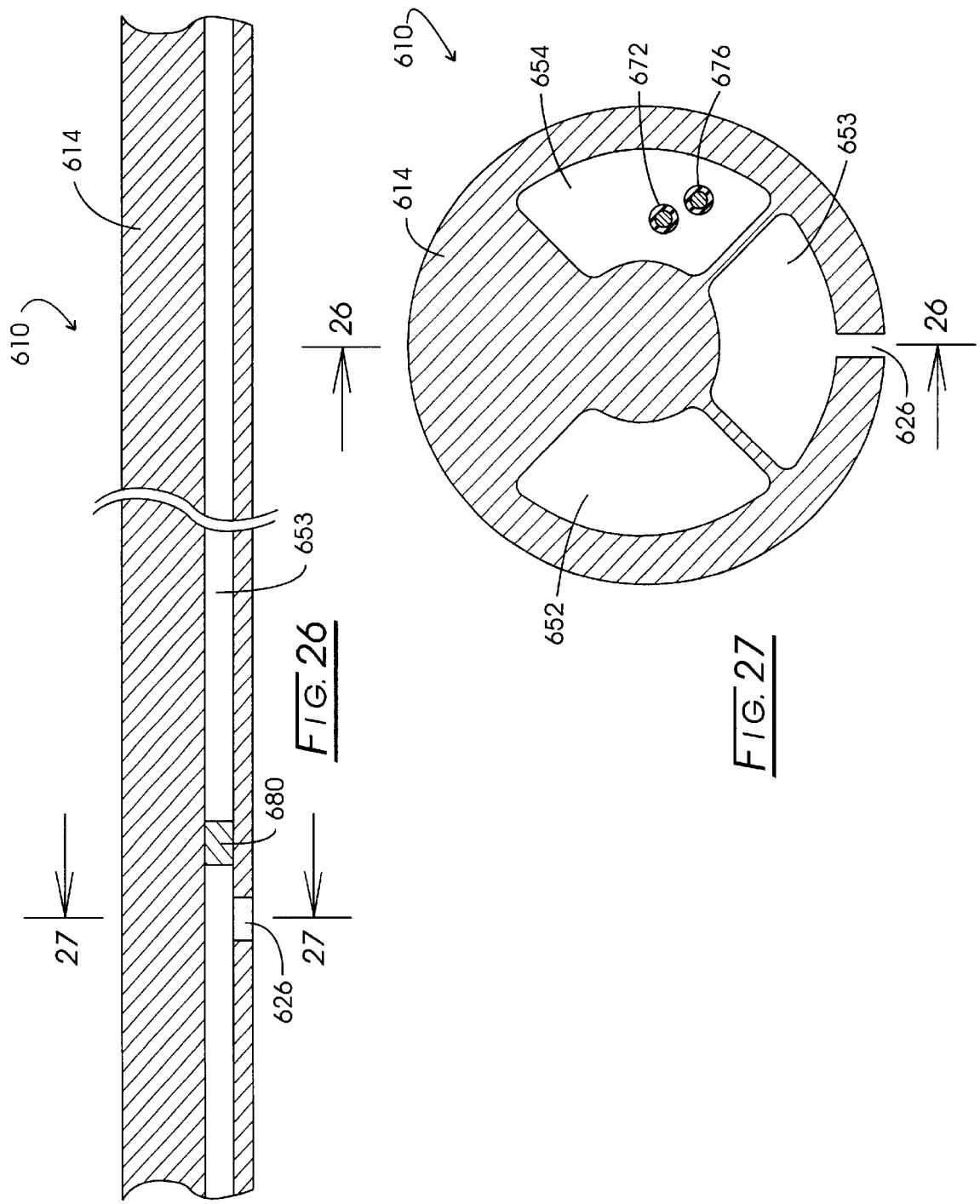

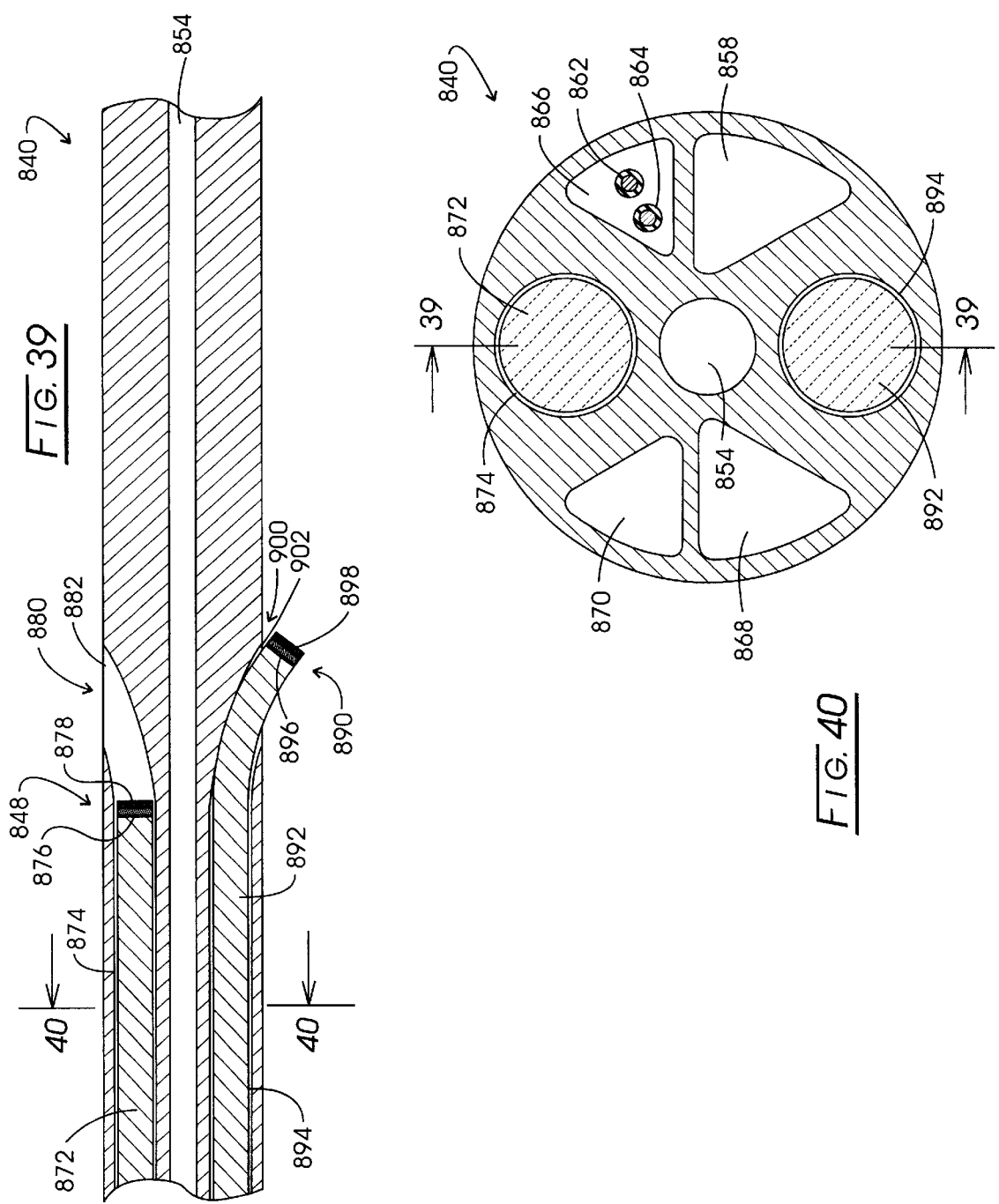

MONITORING TOTAL CIRCULATING BLOOD VOLUME AND CARDIAC OUTPUT

CROSS-REFERENCE TO RELATED APPLICATIONS

The present application for U.S. patent is a continuation-in-part of application Ser. No. 09/040,167 filed Mar. 17, 1998, now U.S. Pat. No. 5,928,155 issued Jul. 27, 1999.

BACKGROUND OF THE INVENTION

The determination of cardiac output, or measurement of the blood volumetric output of the heart is of substantial importance for a variety of medical situations. Intensivists utilize such information along with a number of additional pulmonary factors to evaluate heart patients within intensive care units. A variety of approaches have been developed for measuring this output, all of which exhibit certain limitations and/or inaccuracies. In effect, the volumetric aspect of cardiac output provides information as to the sufficiency of oxygen delivery to the tissue or the oxygenation of such tissue. When combined with other measurements, an important evaluation of the status of the cardiovascular system of a patient may be achieved.

Currently, the more accepted approach for deriving cardiac output values is an indicator dilution technique which takes advantage of refinements made earlier in pulmonary catheter technology. With the indicator dilution approach, a signal is inserted into the blood upstream from the pulmonary artery, and the extent of signal dilution can then be correlated with stroke volume or volumetric output of the heart. Of these indicator dilution methods, thermodilution is the present technique of choice, and in particular, that technique employing a cold liquid injectate as the signal This approach necessarily is invasive, requiring placement of a Swan-Ganz type pulmonary artery catheter such that its tip or distal end functions to position a temperature sensor just beyond the right ventricle within the pulmonary artery. The indicator employed is a bolus of cold isotonic saline which is injected from the indwelling catheter into or near the right atrium. Downstream blood temperature then is monitored to obtain a dilution curve relating temperature deviation to time, such curves sometimes being referred to as "wash out" curves. Combining the area under this thermodilution curve with the amount of energy subtracted by cooling of the blood provides a measure of the rate at which the heart is pumping blood, such rate usually being expressed in liters per minute. If cardiac output is high, the area under the thermodilution curve for a given applied energy, Q, will be relatively small in accordance with the well-known Stewart-Hamilton relationship. Conversely, if cardiac output is low, the area under the thermodilution curve for a given amount of applied energy, Q will be relatively large. See in this regard:

Ganz, et al., "A New Technique for the Measurement of Cardiac Output by Thermodilution in Man," *American Journal of Cardiology*, Vol. 27, April, 1971, pp 392–396.

In a typical procedure, a cold bolus of saline at ice or room temperature in an mount of about 5–10 milliliters is injected through the catheter as a measurement procedure which will require about two minutes to complete. For purposes of gaining accuracy, this procedure is repeated three or four times and readings are averaged. Consequently, the procedure requires an elapsed time of 4–5 minutes. In general, the first measurement undertaken is discarded inasmuch as the catheter will have resided in the bloodstream of the body at a temperature of about 37° C. Accordingly, the first measurement procedure typically is employed for the purpose of cooling the dilution channel of the catheter, and the remaining measurements then are averaged to obtain a single cardiac output value. Thus, up to about 40 ml of fluid is injected into the pulmonary system of the patient with each measurement which is undertaken. As a consequence, this procedure is carried out typically only one to two times per hour over a period of 24 to 72 hours. While practitioners would prefer that the information be developed with much greater frequency, the procedure, while considered to be quite accurate, will add too much fluid to the cardiovascular system if carried out too often. Of course, the accuracy of the procedure is dependent upon an accurate knowledge of the temperature, volume, and rate of injection of the liquid bolus. Liquid volume measurements during manual infusions are difficult to make with substantial accuracy. For example, a syringe may be used for injecting through the catheter with the result that the volume may be identified only within several percent of its actual volume. Operator error associated with volume measurement and rate of injection also may be a problem. Because the pulmonary catheters employed are somewhat lengthy (approximately 30 to 40 inches), it is difficult to know precisely the temperature of the liquid injectate at the point at which it enters the bloodstream near the distal end of that catheter. Heat exchange of the liquid dispensing device such as a syringe with the catheter, and the blood and tissue surrounding the catheter upstream of the point at which the liquid is actually released into the blood may mean that the injectate temperature is known only to within about five percent of its actual temperature. Notwithstanding the slowness of measurement and labor intensity of the cold bolus technique, it is often referred to as the "gold standard" for cardiac output measurement by practitioners. In this regard, other of determining cardiac output typically are evaluated by comparison with the cold bolus approach in order to determine their acceptability.

Another technique of thermodilution to measure cardiac output employs a pulse of temperature elevation as the indicator signal. In general, a heating coil is mounted upon the indwelling catheter so as to be located near the entrance of the heart. That coil is heated for an interval of about three seconds which, in turn, functions to heat the blood passing adjacent to it. As is apparent, the amount of heat which can be generated from a heater element is limited to avoid a thermocoagulation of the blood or damage to tissue in adjacency with the heater. This limits the extent of the signal which will be developed in the presence of what may be considered thermal noise within the human body. In this regard, measurement error will be a result of such noise phenomena because of the physiological blood temperature variation present in the body. Such variations are caused by respirations, coughing, and the effects of certain of the organs of the body itself. See in this regard:

Afonzo, S., et al.., "Intravascular and Intracardiac Blood Temperatures in Man," *Journal of Applied Physiology*, Vol. 17, pp 706–708, 1962.

See also, U.S. Pat. No. 4,595,015.

This thermal noise-based difficulty is not encountered in the cold bolus technique described above, inasmuch as the caloric content of a cold bolus measurement is on the order of about 300 calories. By contrast, because of the limitations on the amount of heat which is generated for the temperature deviation approach, only 15 or 20 calories are available for the measurement. Investigators have attempted to correct for the thermal noise problem through the utilization of filtering techniques, for example, utilizing moving averages over 6 to 12 readings. However, where such corrective filtering approaches are utilized, a sudden downturn in the hemodynamic system of a patient will not be observed by the practitioner until it may be too late. The effective measurement frequency or interval for this technique is somewhat extended, for example about 10 minutes, because of the inaccuracies encountered. In this regard, a cardiac output value is achieved only as a consequence of a sequence of numerous measurements. In general, the approach does not achieve the accuracy of the above-discussed cold bolus technique. Thermodilution techniques involving the use of electrical resistance heaters are described, for example, in U.S. Pat. Nos. 3,359,974; 4,217,910; 4,240,441; and 5,435,308.

Other approaches to the elimination of an injectate in thermodilution procedures have been, for example, to introduce the thermal signal into the flowing blood by circulating a liquid within the catheter, such liquid preferably being cooler than the blood temperature. See in this regard, U.S. Pat No. 4,819,655. While, advantageously, no injectant is utilized with such procedure, the method has the disadvantage that only a limited thermal signal is available as compared with the cold bolus approach, and, thus, the measurement is susceptible to error due to physiological temperature variations. As another example, a technique has been proposed wherein a stochastic excitation signal present as a series of thermal pulses of varying duration is inserted within the bloodstream, and the resultant output signal downstream, now present as blood temperature variation, is measured. The blood flow rate then is extracted by cross-correlating the excitation signal and measured output signal. See U.S. Pat. No. 4,507,974.

Dilution and conductivity dilution techniques, also involving injection of an auxiliary liquid such as a dye or saline solution into the bloodstream are known. See in this regard, U.S. Pat. Nos. 3,269,386; 3,304,413; 3,433,935; 3,820,530; 4,572,206; and 5,092,339. A resulting dye dilution or conductivity dilution curve will be seen to be similar to the above-discussed thermodilution curve. Dye dilution and conductivity dilution procedures exhibit certain of the deficiencies discussed in connection with the injected liquid bolus-based thermodilution approach, namely difficulty in precisely controlling the rate of manual injection and measuring the injectate volume as well as an unsuitability of the procedure for frequent or repeated use over long periods of time. The above-noted dye dilution procedures have been employed for a relatively extensive period of time. In general, a dye is injected into the bloodstream and then a blood sample is drawn, typically from a major artery, at various intervals of time. The technique is quite labor intensive and, because of the extensive amount of dye which is required to obtain an accurate measurement. the frequency of measurement is very low. In particular, if the frequency is attempted to be enhanced, then the signal-to-noise ratio encountered becomes unacceptable as the background color of the blood continues to change. The saline solution approach involves the injection of a hypertonic saline solution having a much higher salt content per unit volume than, for example, typical isotonic saline solution which is about 0.9% sodium chloride. Following injection of the hypertonic saline solution, the electrical resistivity of the blood is evaluated. The method has been criticized inasmuch as such an extensive amount of electrolyte is added to the blood for each measurment, the electrolyte balance in the body becomes adversely affected. Note that the technique looks at electrical charges in a direct fashion as they exist in the bloodstream. Another indicator-dilution method for determining cardiac output involves, the utilization of a cation, preferably lithium, which is not already present in the blood. This cation is injected as a bolus into the blood. A cation selective electrode is used to measure concentration and subsequently develop a resulting cation dilution curve in a manner similar to a thermodilution measurement. Cation-dilution cardiac output measurement methods share certain of the same deficiencies as discussed above for liquid-bolus-based thermodilution methods. See U.S. Pat. No. 5,395,505.

Ultrasonic echocardiography has been employed for the instant purpose. With this invasive method, a plurality of microbubbles is introduced into the blood upstream of the measurement position. As described in U.S. Pat. No. 4,316,391, an ultrasonic pulse is generated from a position opposite and spaced from the region of the flowing microbubbles, for example, using an ultrasonic transducer/receiver located outside of the body. A reflective ultrasonic image, created by reflection of the ultrasonic pulse from the microbubble dispersions is measured and correlated with cardiac output, i.e. flow rate, using conventional dilution techniques. This method preferably employs microbubbles comprising a gelatin membrane-encased "inert" gas such as nitrogen or carbon dioxide to perform each measurement. As a consequence, the method is not suitable for performing clinical measurements continuously or even intermittently for an extended period of time due to the accumulation of bubble membrane material that must be cleared from the body by the body's own cleansing processes.

A derivation of cardiac output by simultaneously measuring blood velocity and vessel geometry has been described, for example, in U.S. Pat. Nos. 4,733,669 and 4,869,263. With this approach, a Doppler pulmonary artery catheter system is provided which develops instantaneous vessel diameter measurements and a mapping of instantaneous blood velocity profiles within the main pulmonary artery. From such data, an instantaneous cardiac output then is calculated. See in this regard the following publication:

"Instantaneous and Continuous Cardiac Output Obtained with a Doppler Pulmonary Artery Catheter," *Journal of the American College of Cardiology*, Vol. 13, No. 6, May, 1989, pp 1382–1392.

A similar approach has been described which involves a technique wherein a piezoelectric ultrasound transducer is placed in the trachea of a patient in proximity to the aorta or pulmonary artery. Ultrasound waves then are transmitted toward the path of flow of blood in the artery and are reflected and received. The cross-sectional size if the artery is measured, based upon the Doppler frequency difference between the transmitted and received waves. Imaging techniques such as X-ray or radioisotopic methods also have been used. See generally the following publication:

"Transtracheal Doppler: A New Procedure for Continuous Cardiac Output Measurement," *Anesthesiology*, Vol. 70, No. 1, Jan. 1989, pp 134–138.

See additionally, U.S. Pat. Nos. 4,671.295 and 4,722,347.

A pulse contour technique for measuring blood velocity which requires a secondary calibration is described in the following publication:

"Continuous Cardiac Output Monitoring During Cardiac Surgery," *Update in Intensive Care and Emergency Medicine*, Berlin: Springer-Verlag, 1990, pp 413–417.

Another approach employs a so-called "hot wire" anemometer or heated thermistor as described in U.S. Pat. No. 4,841,981; EP 235811; U.S. Pat No. 4,685,470, and WO88/06426.

Any of the velocity-based measurement techniques for deriving cardiac output confront a rather basic difficulty not present with indicator dilution approaches. That difficulty resides in the necessity for knowing the geometric cross section of the vessel through which blood is flowing. In this regard, the geometry and diametric extent of the pulmonary artery is not known and is dynamic, changing with the pulsation nature of blood flow. Of course, the velocity measurements themselves must account for the surface effect of the interior of the vessel, velocity varying from essenially a zero value at the interior surface or lumen of the vessel to a maximum value towards the interior of that vessel.

A non-invasive technique evaluating thoracic electrical bioimpedance to derive cardiac outputs has been studied, for example, using electrocardiographic signals (ECG). However, cross-correlation of the results with the well-accepted thermodilution technique have led to questions of reliability.

For a general discourse looking to alternatives to the current indicator dilution method of choice, reference is made to the following publication:

"Alternatives to Swan-Ganz Cardiac Output Monitoring" by Moore, et al., *Surgical Clinics of North America*, Vol. 71, No. 4, Aug. 1991, pp 699–721.

A correlate to the diagnostic, cardiac output (CO) is the corresponding value for total circulating blood volume (CVB). The first and most important therapeutic goal for hemorrhagic, post operative, cardiogenic, traumatic, neuogenic for septic shock is to restore blood volume to normal levels. Determining blood volume, however, has been an elusive undertaking. Typically, other hemodynamic parameters such as mean arterial pressure (MAP), wedge pressure (WP) or occlusion pressure, central venous pressure (CVP) and hematocrit (Hct) are used by clinicians to infer blood volume. However, such inferentially based approaches do not accurately reflect blood volume except at more extreme departures from normal levels. See in this regard:

Shippey, C. R., Appel, P. L., Shoemaker, W. C., "Reliability of Clinical Monitoring to Access Blood Volume in Critically Ill Patents", *Critical Care Medicine*, Vol. 12, No. 2, pp 107–112 (1984)

A broad variety of patient conditions are associated with the abnormal blood volume levels referred to as "hypovolemia" (circulating volume too low) and "hypervolemia" (circulating volume too high). Hypovolemia occurs commonly during surgery and represents a significant cause of intestinal hypoperfusion. Hypoperfusion occurs as a response to any reduction in circulating blood volume as blood is directed away from the intestinal vascular bed in favor of vital organs. Management of circulating blood volume is essential prior to, during and following cardiopulmonary bypass procedures, inasmuch as avoiding hypovolemia improves organ perfusion and reduces morbidity and mortality. Circulating blood volume data also is important for carrying out the treatment of patients with ruptured cerebral aneurysms who often are hypovolemic. Hemorrhegic shock following traumatic injury is caused by extensive blood loss or blood loss induced trauma in the central nervous system. Failure to recognize the presence or extent of blood loss is an important factor in avoiding the loss of the patient. While hypotensive injury victims routinely receive rapid fluid resuscitation, an excessive addition of fluid into the vascular system may increase bleeding and worsen the outcome, see:

Silbergleit, Schultz, et al, "A New Model of Uncontrolled Hemorrhage that Allows Correlation of Blood Pressure and Hemorrhage", *Academic Emergency Medicine*, Vol. 3 No. 10, pp 917–921 (1996).

Hypovolemia is one of the principal defects contributing to cardiovascular instability and circulatory failure during septic shock. During sepsis, microcirculation often is severely impaired to exacerbate the problem of hypervolemia. Hypovolemia-induced hypotension is reported to complicate approximately 30% of all dialysis treatments. Short duration hemodialysis involving ultra filtration can cause hypovolemia unless corrective action is taken such as reducing the filtration rate or interrupting the hemodialysis process to allow for compensatory changes in the patients circulating blood volume. Acute renal failure occurs most commonly in a setting of surgery and trauma due to hypovolemia, sepsis, obstetric complications, hemolytic reaction and poisoning. A principal challenge to practitioners treating burn patients is the management of circulating blood volume in the presence of excessive plasma loss at the burn sites. Hypovolemia is a common complication of patients with burns.

Conventional methods for measuring circulating blood volume depend typically upon the dilution of a dye, radioactive tracer or other analyte which, following injection is mixed into the bloodstream. Blood volume then is calculated, inter alia, from the extent of dilution and such calculation assumes that the indicator-analyte is immisible in red blood cells.

In order to estimate total circulation blood volume (TCBV), i.e., the summation of plasma volume (PV) and red blood cell volume (RBCV), the large vessel hematocrit (LVH) also is measured so that total blood volume is obtained by the following relationships:

$$\text{Plasma Volume Measured: } TCBV = \frac{PV}{1.0 - LVH} \quad (1)$$

$$\text{Red Blood Cell Volume Measured: } TBBV = \frac{RBCV}{LVH} \quad (2)$$

The most accurate method for measuring total blood volume avoids the potential error of using the large vessel hematocrit value (which is not representative of the hematocrit throughout the circulatory system) by separately measuring the plasma volume and red blood cell volume. This method is known as the Summation Method. See generally:

Dagher et al, "Blood Volume Measurements: A Critical Study. Prediction of Normal Values: Controlled Measurement of Sequential Changes: Choice of a Bedside Method", Advances In Surgery 1969; 1:69–109.

As has been reported in the literature since 1941, of the various radionuclides employed, a technique utilizing $^{51}$Cr has been considered a "gold standard" for deriving circulating blood volume values. However, this approach, as well as dye-based dilution approaches are both costly and are limited to relatively infrequent measurement. As a consequence, a continuous monitoring of blood volume changes or trending-type monitoring has not been available to practitioners. A more recent approach, utilizing $^{131}$I as a radiolabel provides for the obtaining of a plurality of blood samples over 20–35 minutes following tracer injection. Tracer dilution is combined with hemocrit to calculate blood volume. See in this regard: U.S. Pat. Nos. 5,024,231 and 5,529,189. In general, this approach has been problematic in terms of cost, limitations on the number of measurements which can be made, and the inherent procedure and physiologic limitations associated with the radionuclide.

Practitioners involved in the management of more critical hemodynamic conditions, typically turn to commonly monitored and thus more immediately available parameters such as mean arterial pressure (MAP), pulmonary catheter wedge pressure (PCWP), central venous pressure (CVP), heart rate (HR) and hematocrit (HCT) to estimate or infer a value for total circulating blood volume. Studies have shown, however, that such inference-based determinations are prone to error.

BRIEF SUMMARY OF THE INVENTION

The present invention is addressed to a system and method for determining hemodynamic parameters of a cardiovascular system utilizing indicator-dilution based techniques. Such techniques are employed in conjunction with analyte-containing fluids which are biocompatible with and metabolizable within the body of a patient. The principal hemodynamic parameters derived are total circulating blood volume (TCBV) and cardiac output (CO). Derivation of both of these parameters may be achieved using a common analyte in conjunction with a dilution measurement procedure. Because the analyte employed with the system is metabolizable within the body, measurements deriving the parameters may be carried out at a relatively rapid measurement frequency. This desirable measurement activity is achieved without otherwise harmful analyte concentration buildups, i.e., without adverse consequences to body homeostasis or stability. Thus, the system may generate a substantial number of outputs of highly important value to the practitioner. For example, the system provides alarms or warnings when a parameter varies from an inputted threshold value. Such thresholds not only may be of a chosen hemodynamic parameter value, but also may be developed with respect to rates of changes of the parameters. The information generated may be employed in combination with real time data to publish parameter trends over time. In effect, an automatic charting of the progress of the patient with respect to these parameters is carried out. Heretofore, the cardiac output parameter has, for the most part, been measured utilizing heart invading catheters such as pulmonary artery catheters, portions which enter the heart itself. Total circulating blood volume generally has been inferred from a variety of other measurements carried out with such heart invading instrumentation. However, with the present system and procedure, safer, less invasive instrumentation may be used, for example, within the cardiovascular system, but at peripheral locations in the body spaced from the heart. With the instrumentation so peripherally located, both cardiac output and total circulating blood volume values may be directly measured, no inferences being called for to achieve values for the latter parameter. This capability for carrying out such measurements at peripheral regions of the cardiovascular system significantly expands the patient population upon which such measurements would be carried out, inasmuch as the procedure is much less hazardous. Such lessening of risk to the patient also permits an expansion of the number of medical personnel having qualifications permitting their carrying out these measurements.

The procedure for making these hemodynamic parameter measurements involves the utilization of a delivery assembly with a delivery channel extending to an output within the bloodstream. Analyte-containing fluid is introduced from a source into the delivery channel to be expressed from the channel output into the bloodstream. This fluid introduction is at a controlled mass flow rate occurring over an infusion interval, the system control being responsive to timing associated with such interval. Also located within the bloodstream is an analyte concentration sensor having a succession of sensor outputs corresponding with the varying analyte concentration witnessed by the sensor. A controller reacts to these activities to develop a sequence of time associated analyte concentration values which, in effect, represents the dynamic formation of a curve of analyte concentration values which rise from a baseline value toward an inflexion defining peak and then decline or decay to define a time-based descending curve slope. Microprocessor driven computation then correlates those concentration values occurring subsequent to the peak value with a time of delivery datum associated with the infusion interval to derive a value for total circulating blood volume.

The forward or ascending portion peak value of this curve reached by the time associated concentration values is used for one approach to computing cardiac output, while a second approach utilizes an integrated value for substantially the entire curve of concentration values. Extrapolation techniques may be employed to expedite the procedure of peak and slope identification. In general, measurement of the parameters of cardiac output and total circulating blood volume are evolved about every one to eight minutes in conjunction with sensor outputs occurring about each second. The infusion interval generally is selected from within a range of about 2 to 30 seconds.

The instrumentation involved in this procedure can assume a number of different configurations. For example, relatively smaller arterial line catheters with analyte sensing and fluid delivery channels are described. Separate delivery and sensing instruments of quite diminutive size may be employed where blood flow diversion might be occasioned by the blood hydraulic effects of the instruments. Where heart indwelling catheters such as pulmonary artery catheters are necessitated for other purposes, the system and method of the invention may be utilized with adaptations of them. Such adaptations, for example, provide for the positioning of the analyte sensor region of the catheters at the pulmonary valve when the catheters are inserted in order to substantially "center" the sensors within the bloodstream.

Biocompatible and metabolizable analytes which are employed with the systems include: ammoniacal fluid, heparin, ethanol, glucose and anesthesia agent. Because a somewhat thorough mixing of the analyte in blood is called for to achieve total circulating blood volume measurement, candidate analytes which would be treated at the lungs such as oxygen or carbon dioxide are not utilized, inasmuch as the signal which they represent would be lost as the blood circulates and is so treated. The preferred analyte-containing fluid is ammoniacal fluid and the preferred component selected for sensing is ammonia gas ($NH_3$). Where the concentration of that component is sensed, the value of blood pH is required for a resultant computation of total ammoniacal content. A pH sensor may be incorporated with the analyte sensor in a catheter structure. Where very diminutive size sensor assemblies are utilized, a pH sensor assembly may be provided as a separate instrument.

Utilization of ammoniacal fluid as the analyte containing fluid also permits the system to monitor total ammoniacal content in the blood. Preferably these measurements are filtered with a moving average filter and the resultant filter data is charted with time for trend analysis and further is subjected to automated thresholding procedures.

A preferred analyte sensing structure is described which utilizes fiberoptic technology in combination with a porous polymeric membrane into which a dye the color of which is sensitive to the analyte component measured is immobilized. This matrix or membrane supporting the dye is attached to the face or tip of a fiberoptic strand or assembly utilizing an intermediate nonporous optically transparent polymeric layer which, in turn, is adhesively attached to the fiberoptic face.

As another aspect of the invention, a method is provided for determining hemodynamic parameters of a cardiovascular system wherein blood within a bloodstream is circulated to peripheral regions of the body and exhibits a pH value, comprising the steps of:

(a) providing a source of analyte-containing fluid biocompatible with and metabolizable within the body and having a predetermined analyte concentration;

(b) providing an analyte concentration sensor having a distal analyte responsive portion configured for positioning within the bloodstream and which is responsive to the presence of analyte to provide sensor outputs corresponding with the sensed concentration of analyte;

(c) providing a delivery assembly having a delivery channel with an input coupled in fluid flow communication with the source of analyte-containing fluid and an output configured for positioning within the bloodstream;

(d) positioning the analyte concentration sensor distal analyte responsive portion and the delivery assembly output within the bloodstream;

(e) delivering the analyte-containing fluid from the source into the delivery channel at a time of delivery, a mass flow rate and over an infusion interval;

(f) deriving a sequence of time associated analyte concentration values from the sensor output;

(g) monitoring the sequence of time associated analyte concentration values and identifying a sequence thereof rising in value to a peak defining inflection value and descending in value therefrom; and (h) deriving a value for a select one of the hemodynamic parameters by correlating the sequence of time associated concentration values, the mass flow rate, the infusion interval and the predetermined analyte concentration.

The provision of the analyte concentration sensor within the bloodstream, (step (d) above) may be carried out in conjunction with a blood flow by-pass system wherein the sampling location or chamber is remote from the body of the patient.

Other objects of the invention will, in part, be obvious and will, in part, appear here and after. The invention, accordingly, comprises the method and system possessing the construction, combination of elements, arrangement of parts and steps which are exemplified in the following detailed description. For a fuller understanding of the nature and objects of the invention, reference should be made to the following detailed description taken in connection with the accompanying drawings.

BRIEF DESCRIPTION OF THE DRAWINGS

FIG. 11 is a partial sectional view of the forward end region of the catheter of FIG. 10;

FIG. 12 is a sectional view taken through the plane 12—12 in FIG. 11;

FIG. 21 is a schematic representation of optical components performing with a sensor according to the invention;

FIG. 22 is a sectional view taken through the plane 22—22 shown in FIG. 21;

FIG. 24 is a partial sectional view of the catheter of FIG. 23 taken through the plane 24—24 in FIG. 25;

FIG. 25 is a sectional view taken through the plane 25—25 in FIG. 24;

FIG. 26 is a partial sectional view of the catheter of FIG. 23 taken through the plane 26—26 in FIG. 27;

FIG. 27 is a sectional view taken through the plane 27—27 in FIG. 26;

FIG. 39 is a partial sectional view of a portion of the catheter shown in FIG. 36 and taken through the plane 39—39 shown if FIG. 40;

FIG. 40 is sectional view taken through the plane 40—40 shown in FIG. 39;

DETAILED DESCRIPTION OF THE INVENTION

Figure 1:
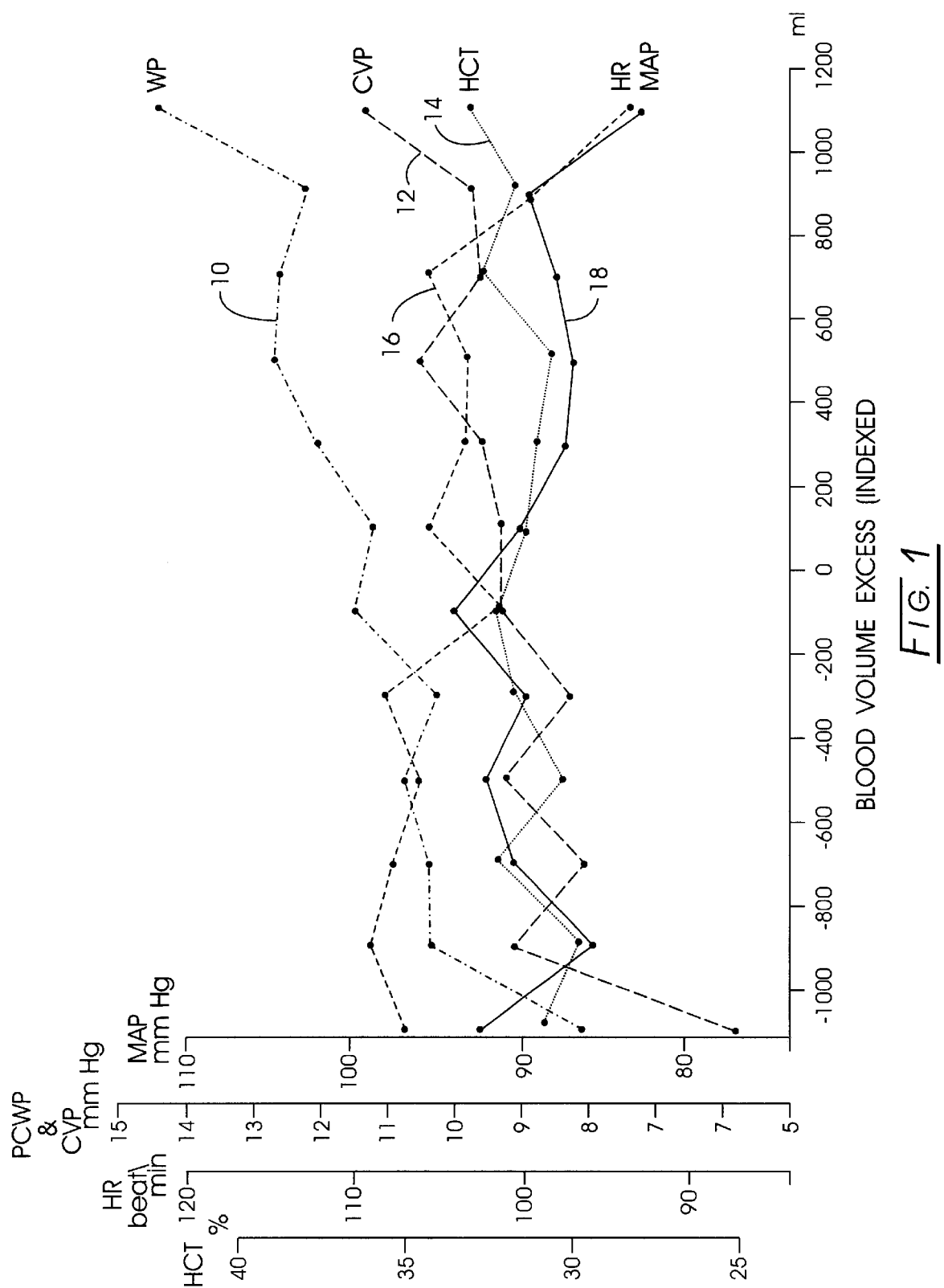
FIG. 1 is a graph showing values of blood volume index which are plotted against values of hemodynamic variables.

Gaining information as to total circulating blood volume from other hemodynamic parameters generally has become an accepted procedure in connection with the management of critically ill patients. For example, mean arterial pressure (MAP), heart rate (HR), hematocrit (HCT) and urine output are used conventionally as the diagnostic parameters for fluid management of patients with suspected hypovolemia or hypervolemia. Invasively monitored parameters employing catheters which dwell within the heart also are utilized and will include, for example, central venous pressure (CVP) and pulmonary catheter wedge pressure (PCWP). While these techniques of inference have the advantage of providing more immediate data, that data tends to be inaccurate except upon the occurrence of very serious excursions in the values of hypervolemia and hypovolemia. This is demonstrated in FIG. 1 where values of commonly monitored hemodynamic variables are identified along the ordinate of a curve sequence. Then variables are plotted against corresponding indexed blood volume excess and deficit. In the figure, wedge pressure (WP) is shown at curve 10; central venous pressure (CVP) is shown at curve 12; hematocrit (HCT) is shown at curve 14; heart rate (HR) is shown at curve 16; and mean arterial pressure (MAP) is represented at curve 18. It may be noted that a poor interrelationship exists between these parameters and accurately measured blood volume except at extreme blood volume deficiencies or excesses. See generally:

Shippy, et al, "Reliability of Clinical Monitoring to Assess Blood Volume in Critically Ill Patients", *Critical Care Medicine,* 1984;12:107–112.

The present monitoring system and method provides for ideally frequent and direct measurement of the hemodynamic parameters of total circulating blood volume (TCBV) and cardiac output (CO) utilizing dilution-based techniques. With these techniques administration of an analyte injectate under a pre-established infusion interval permits a rapid generation of each of these hemodynamic parameters. The frequency of measurement may, for example, be every two to three minutes and the administration of the analyte-containing fluid, as well as the sensing of the analyte concentration may be carried out with less invasive instrumentation positioned within the bloodstream of the cardiovascular system at locations which may be considered peripheral or spaced from the heart. This injectate employed with the dilution or mixing approach is an analyte-containing fluid which, of importance, is both biocompatible with and metabolizable within the body of the patient. The term "analyte" as employed herein is considered to be such a metabolizable substance which is undergoing analysis. The analyte-containing fluid may be essentially all analyte or a combination of a species of analyte or specific analyte with other components which are metabolized. With the noted frequent measurement intervals, the concentration of analyte within the body will build, at least initially. However, somewhat simultaneously, the body metabolizes this analyte injectate and after a sequence of measurements, will reach a state of metabolic homeostasis or equilibrium wherein the analyte concentration remains constant and below a homeostasis threshold value. That threshold value corresponds with analyte concentration for iatrogenesis. The latter is a level which would adversely affect the patient. The analyte-containing fluids which are employed with the invention are selected such that they are not significantly affected by oxygenation of the bloodstream as it is treated during passage through the lungs. In this regard, the analyte-containing fluids are selected from the group consisting of ammoniacal fluid, heparin, ethanol, glucose and anesthesia agents. Of that group, the preferred analyte-containing fluid is an ammoniacal fluid. A variety of analyte concentration sensors employable with the system and technique are described. Because of the complimenting analyte and analyte concentration sensor approach utilized in conjunction with a metabolic process of the body, the system may be automated to perform under controller-based technology. Such technology permits, in turn, the generation of substantial additional data, for example, involving operator inserted threshold values, threshold rates of change of measured values and associated warnings and alarms and, additionally the outputting of trending data providing the practitioner with a graphical or least numerical view of patient progress or lack thereof.

The preferred embodiment of the system and method employs the noted ammoniacal fluid as the analyte-containing fluid, for example, ammonium chloride. The analyte concentration derived for this selection will be the combined content of ammonia gas and ammonium ion. In this regard, ammonia gas ($NH_3$) and ammonium ion ($NH_4^+$) are in the equilibrium ($NH_3 + H > NH_4^+$). The pKa of this reaction is 9.3, thus at the physiological pH, the ammonium ion, $NH_4^+$ is mostly present. However, the preferred analyte component for concentration sensing in blood is ammonia gas ($NH_3$). A particular advantage accruing with the use of ammoniacal fluid as the analyte-conveying fluid or injectate of the procedure is a discovery that, when utilizing this analyte-containing fluid, derivation of TCBV does not depend upon an evaluation of hematocrit (HCT). In this regard, the components of the analyte-conveying fluid enter the red blood cells as well as plasma in a uniform way such that by sensing the amount of ammonia ($NH_3$), the system will obtain a dilution-based measurement which is independent of the hematocrit component of blood.

In general, the analyte which is utilized under the precepts of the invention may be an anabolite or product of a constructive metabolic process, or a catabolite, or product which, by a destructive metabolic process, is converted into an excreted compound. In the latter metabolic category, the transformation which occurs represents a utility making energy available for organs in use. Desirably, enhanced measurement freqencies are made available with the procedure since there is no substantial hemodilution nor evoked body system instability. While relatively minor baseline analyte concentration value shifting is encountered, the metabolic reaction to the introduced biocompatible analyte-containing fluid functions to maintain the patient in a stable condition.

Ammoniacal fluid-based indicators may be the subject of uptake by certain organs of the body for further catabolism and excretion, or they may remain in the body by anabolism or incorporation into other nitrogenous products. The amount of analyte infused for each hemodynamic parameter measurement is based on the measurement precision of the sensor, the frequency of measurements required per day and the rate of metabolism. For the case of an ammoniacal fluid, the rate of metabolism or clearance of ammoniacal products from the blood has been reported to increase with concentration. See in this regard:

Lockwood, A. H., et al., "The Dynamics of Ammonia Metabolism in Man-Effects of Liver Disease and Hyperammonemia", *J. Clin. Invest.*, Vol. 63, pp 449–460, 1979.

Figure 2:
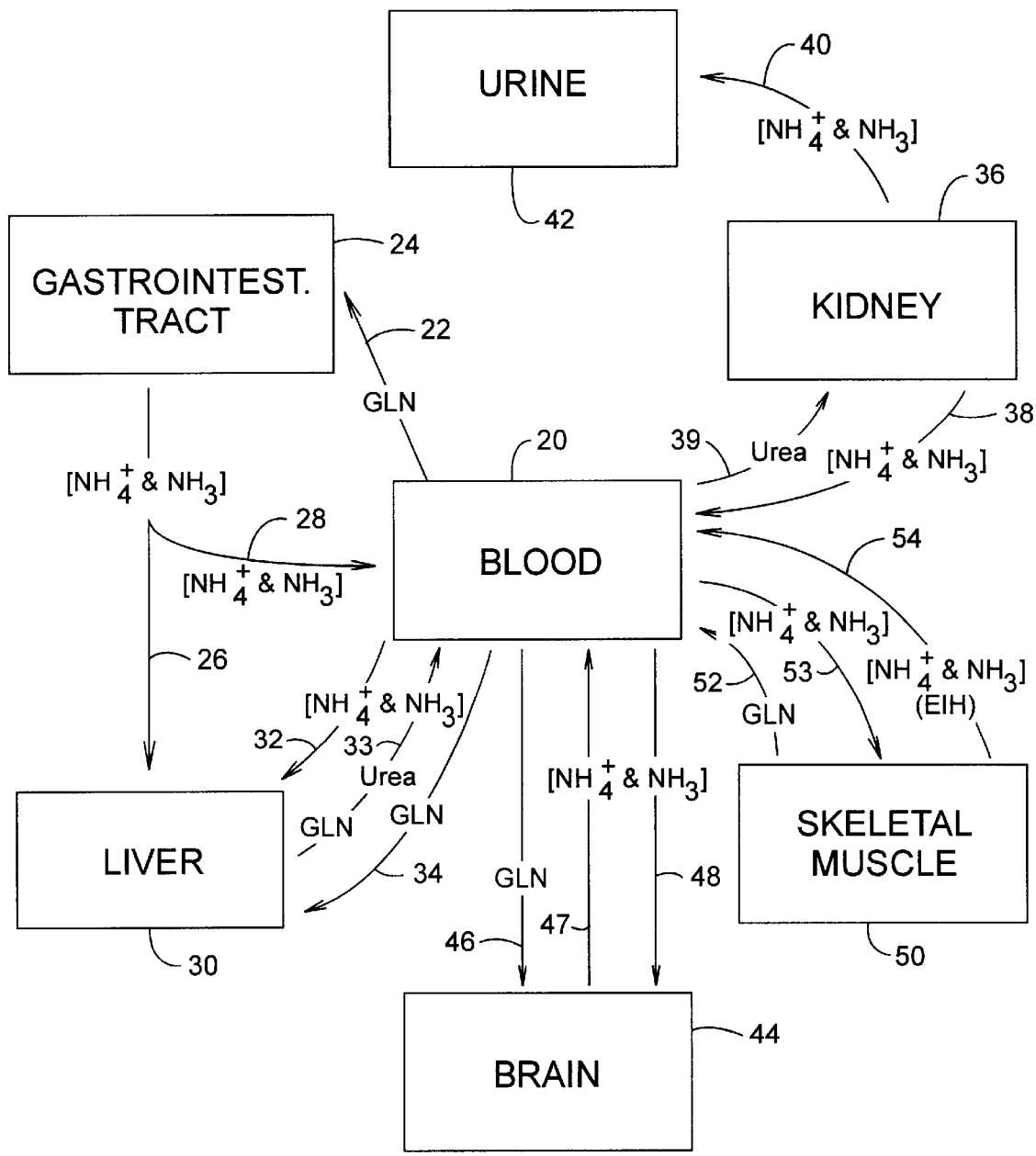
FIG. 2 is a block diagram illustrating various sources, metabolism sites, and clearance pathways for ammoniacal products in the human body.

Under resting conditions, most blood ammonia/ammonium is of dietary origin. Normal digestive processes generate ammoniacal concentration from ingested protein, while bacteria in the gastrointestinal tract generate ammoniacal concentration by metabolizing protein products of dietary protein digestion and urea. An illustration of the major organs of ammonia/ammonium formation, utilization and circulation is presented in FIG. 2. The figure includes representations of the various forms of nitrogenous compounds, e.g., ammonia gas ($NH_3$), ammonium ion ($NH_4^+$) or related nitrogenous bi-products. Ammonia/ammonium metabolically formed in a given organ of the body generally is widely distributed. In FIG. 2, the blood pool or blood system is represented at block 20. Blood pool 20 is depicted supplying glutamine (GLN) to the gut or gastrointestinal tract as represented at arrow 22 and block 24. Ammonia/ammonium generated in the gut 24 from protein digestion and deamination of glutamine (GLN) enters the portal venous circulation as represented at arrows 26 and 28 and is involved in the liver function as represented at block 30. The metabolic relationship of the blood pool or blood system 20 with the liver is represented by arrows 32–34. Metabolic interaction with the kidney as at block 36 is represented at arrows 38 and 39, while catabolic ammonium is excreted as represented at arrow 40 and block 42. Transport to and from the brain with respect to the blood pool is represented at block 44 and arrows 46–48. A similar metabolic interrelationship with respect to skeletal muscle is represented at block 50 and arrows 52 and 53. Exercise induced hyperammonemia (EIH) will witness a transfer of ammonium ion into the blood supply as represented at arrow 54. It may be observed that such relatively short excursions thus are readily tolerated by the body. See generally:

"Exercise-Induced Hyperammonemia: Peripheral and Central Effects", Bannister, et al., *Int J. of Sports Medicine*, Vol. 11, pp 5129–5142 (1990).

Under conditions typical of patients in an intensive care unit, resting muscles take up ammonia/ammonium from the circulating blood wherein the substance enters into protein synthesis via ketoglutaric and glutamic acid. When the muscle begins working again, ammonia/ammonium is once again released from the muscle into the bloodstream. If additional ammonia/ammonium (in the form of ammonium salt solution) is injected into a peripheral vein, the added ammoniacal content is brought directly to tissue via the blood where it may be retained and eventually used for amino acid protein synthesis. See:

Furst, P., et al., "Nitrogen Balance After Intravenous and Oral Administration of Ammonia Salts in Man", *Journal of Applied Physiology*, Vol. 26, No. 1 pp 13–22 (1969).

While the hemodynamic parameters of cardiac output and total circulating blood volume may be measured in accordance with the invention employing invasive instrumentation, for example, using heart indwelling catheters such as a pulmonary artery catheter, the measurements also may be made with less invasive instrumentation and concomitant lowered risk to the patient. With the procedure, a controlled infusion of analyte-containing fluid is made into the bloodstream and the extent of dilution of the analyte is evaluated to determine the parameter, cardiac output (CO). A sensed diluted mixture of the analyte within the bloodstream also is used to calculate total circulating blood volume (TCBV). The frequency of measurement can be advantageously high, for example, between two and three minutes per measurement for CO and about every four minutes for TCBV. When both hemodynamic parameters are measured, the measurements are alternated, the measurement frequency for TCBV being advanced to about eight minutes. Advantageously, total ammoniacal content in the blood (TAC) also may be monitored in a preferred approach Referring to FIG. 3, a partial anterior view (palm up) of the body of the patient shown generally at 60 is presented. Within the outline of the body 60 there is shown a heart represented generally at 62. In general, heart 62 performs in two stages or sides, having a right side which receives venous-based blood returning from various tissues and vessels of the body. This right side of the heart is shown at 64 and functions to pump the oxygen depleted blood arriving from the venous system to the lungs to be oxygenated. Components of the venous system shown in the drawing include the internal jugular vein, the external jugular vein 68, the superior vena cava 70, the subclavian vein 72, the brachiocephalic vein 74 and the axillary vein 76. Arrows shown in these components representing blood flow direction are seen directed toward the right side of the heart 64. The blood In the bloodstream thus depicted, upon being oxygenated by the lungs and cleared of excess carbon dioxide, is returned from the lungs and pumped arterially against vascular resistance of the entire body by the left side of the heart which is represented at 78. Shown in the figure is the aorta 80 extending to the aortic arch 82 upwardly from which extends the brachiocephalic artery 84, the common carotid artery 86 and the left subclavian artery 88. Extending into the arm 90 is the brachial artery 92 which, in turn, branches to the radial artery 94 and the ulnar artery 96.

Shown percutaneously introduced into the subclavian vein 72 is an analyte-containing fluid delivery assembly represented generally at 100. The assembly 100 may be quite simple in structure, comprising a thin flexible tube 102 which is guided into the vein 72 with an insertion instrument 104. Tube 102 is formed with a delivery channel extending to a tip 106 through which analyte-containing fluid is expressed. This fluid is delivered at a predetermined mass flow rate and for a controlled infusion interval, the mass flow rate and the interval being combined to define a dose, for example in micro-moles of analyte. Particularly for the measurement of total circulating blood volume, it is desirable that the infusion interval be as short as possible, for example, less than about 20 seconds and typically five seconds. This short interval serves to avoid a re-circulation phenomena wherein the earlier injected analyte is combined with currently injected analyte. Where such re-circulation occurs, then the computation of total analyte concentration must account for the re-circulation effect. Note that the tip 106 of the delivery assembly 100 is well spaced from the right side entrance of the heart 62 and thus, introduction of the analyte-containing fluid at this location represents a much less invasive procedure. In effect, the tip 106 is located at a peripheral region of the cardiovascular system of the body 60. Assembly 100 further includes a delivery conduit or tube 108 which extends to the source of analyte-containing fluid and an associated fluid flow control apparatus.

Positioned within the bloodstream, here shown as at the radial artery 94, is an analyte concentration sensor represented generally at 114. Shown implemented as a relatively small inline arterial catheter 116, the sensor 114 is configured having two, fiberoptic based sensor channels as well as two auxiliary channels which are formed within a polymeric body. That polymeric body extends through an introducer instrument 118. The catheter tip 120 protrudes from the end of the introducer instrument 118. In the preferred embodiment, one of the fiberoptic channels includes a fiberoptic strand which extends to a channel tip incorporating a membrane and dye material responsive to the concentration of analyte at the radial artery 94. The second fiberoptic channel is one measuring pH and extends to a membrane defined equilibration chamber located at the tip 120. Preferably, the forward faces of the sensor components confront flowing blood, as opposed to being inserted within the bloodstream such that the blood flows around the sensor tip from a rearward location. For a latter positioning, the sensing speed may be slowed. In this regard, it is desirable that the sensing speed be as swift as possible. The fiberoptic based sensors are interrogated from a control assembly communicating with the fiberoptic based channel via a control cable shown at 122 extending to an optic coupler 124. Two auxiliary channels within the catheter 116 may be employed for obtaining blood samples or introducing medicants. Access to those auxiliary channels is provided from tubes 126 and 128 shown extending, in turn, to respective valve-coupler assemblies 130 and 132.

The fluid flow metering associated with delivery assembly 100 and the analyte concentration sensor 114 along with its associated pH sensor are controlled from a microprocessor driven controller such that the noted infusion interval and mass flow rate are accurately established. Additionally, the analyte concentration sensor 114 is interrogated to evolve an output reading at a pre-selected frequency, for example, within a range of about 0.1 to 10 seconds. In general, the frequency of this selection is determined so that a peak value of analyte concentration can be identified.

The control function of the system generally will compute total analyte concentration from the outputs of the concentration sensor 114. These values, for example, arriving at a one second measurement frequency interval, for hemodynamic parameter measurement purposes, will arrive, in concert with a time datum associated with the infusion interval, as time associated analyte concentration values. These values, in effect, define a curve having a rising commencement portion extending to an inflection defining peak and then a decaying tail portion. Two techniques are carried out by the control function to determine cardiac output, one deemed an equilibrium method, being concerned with the noted peak value for time associated analyte concentration value as it extends above a baseline concentration value and the other deemed a non-equilibrium method, being derived as the integration of the curve above the baseline values defined by the time associated analyte concentration values. That curve is referred to herein as a "concentration curve".

The infusion interval, mass flow rate of analyte-containing fluid delivery and the concentration of the analyte are selected by the manufacturer based upon a number of criteria. For example, the infusion interval generally is expanded where the measured hemodynamic parameter is cardiac output, which is computed according to the above-discussed "equilibrium" method. Where the parameter total circulating blood volume only is to be measured, then the infusion interval is reduced. Such reduction also may be considered where the only measurement for cardiac output to be carried out is based upon the second, area under the concentration curve approach is used. The extent of the infusion interval also is influenced by the reaction time or speed of the analyte concentration sensor. As that speed is improved or increased, then the infusion interval may be lessened.

Figure 4:
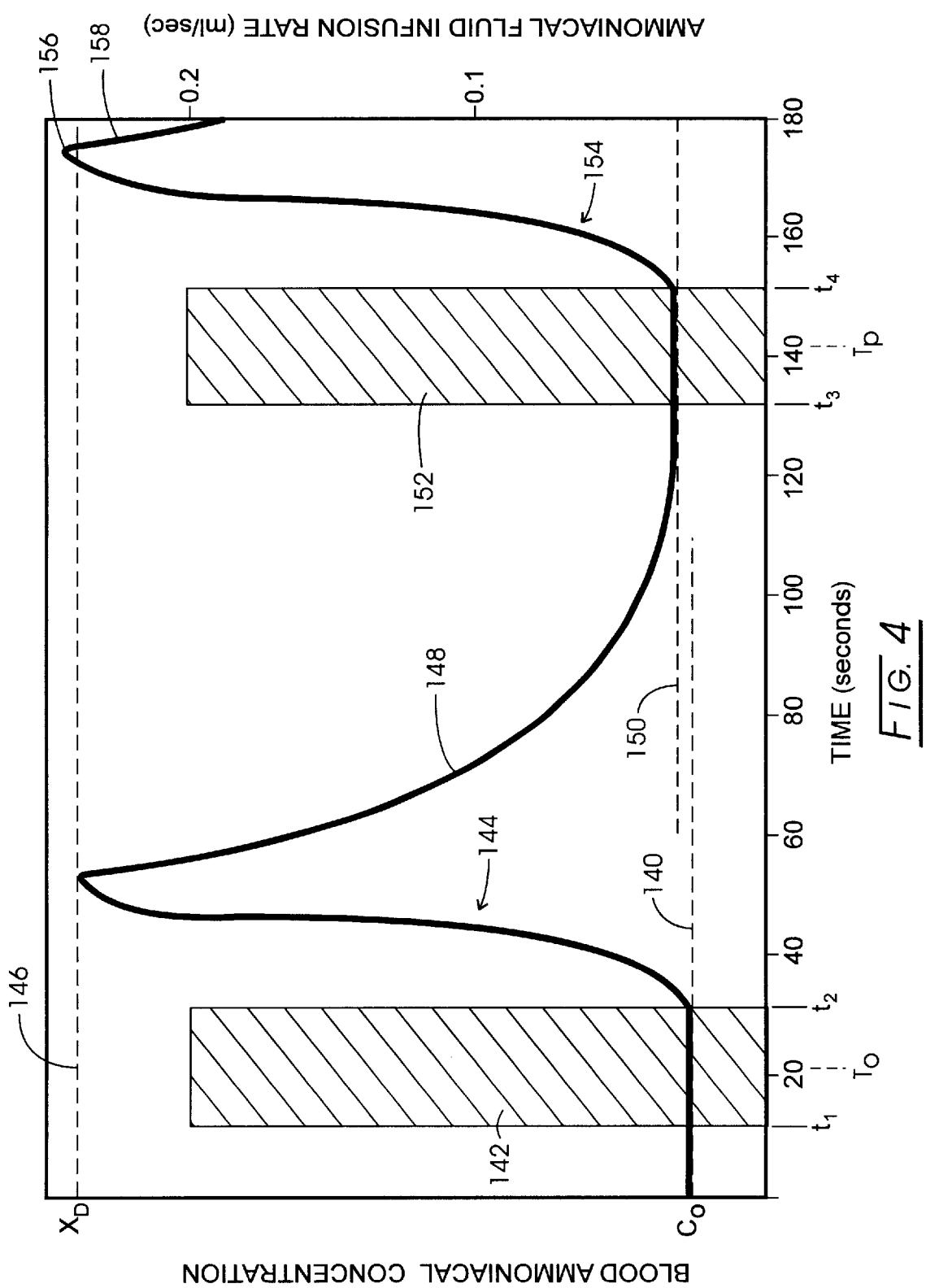
FIG. 4 is a graph schematically plotting blood ammoniacal concentration with respect to a sequence of two hemodynamic parameter measurements carried out in accordance with the invention.

Using, as an example, ammoniacal fluid as the analyte-containing fluid, and referring to FIG. 4, the multiple measurement procedure of the invention may be illustrated. In the figure, an infusion interval is depicted which is suited for the equilibrium for measuring cardiac output and is thus suited for the approach wherein the area under the equilibrium curve is determined or measurement is made of total circulating blood volume. The equilibrium method may be described in conjunction with the following generalized expression:

$$CO = \frac{(\text{Rate of Infusion})(\text{Concentration of Analyte})}{(\text{Maximum Change in Concentration})} \quad (3)$$

The non-equilibrium method employing the area under the concentration curve may be described with the following generalized expression:

$$CO = \frac{(\text{Rate of Infusion})(\text{Concentration of Analyte})(\text{Duration of Infusion})}{(\text{Area Under Concentration Curve})} \quad (4)$$

The method for calculating total circulating blood volume (TCBV) may be generally expressed as follows:

$$TCBV = \frac{(\text{Dose of Analyte Infusion})}{\text{Extrapolated Maximum Concentration Increase at Infusion}} \quad (5)$$

In FIG. 4, two of a sequence of analyte-containing fluid infusion intervals are represented in conjunction with a time-related abscissa, a left-side ordinate representing blood ammoniacal concentration and a right ordinate representing ammoniacal fluid or analyte-containing fluid infusion rate. With the procedure, following the positioning of delivery assembly 100 and analyte concentration sensor 114 as described in conjunction with FIG. 3, a baseline analyte concentration value in the bloodstream is measured with the analyte sensor. This value is converted to blood ammoniacal concentration and represents a baseline value thereof shown as $C_0$ at dashed concentration level line 140. An initial infusion of analyte-containing fluid, or ammoniacal fluid for the instant demonstration, then is carried out for an infusion interval represented at cross-hatched rectangle 142. The commencement of this infusion interval is represented at $t_1$. Ammoniacal concentration sensor 114 will commence to be controlled for carrying out a relatively rapid sequence of concentration measurement. In a preferred embodiment, these measurements will be made of the ammonia $NH_3$ gas component of the analyte. That value then is combined with the pH value of the blood to derive total ammoniacal concentration (TAC). The measurement and computation will be carried out, for example, at about one second intervals to derive the sequence of time associated concentration values. At the commencement of the infusion interval 142, analyte concentration values will be static or level, inasmuch as a delay will ensue before the analyte reaches the location of the sensor in the bloodstream at a peripheral region of the patient's body. However, as the analyte reaches the sensor, here illustrated as occurring at about the time of termination of the infusion interval 142 or at $t_2$, the time associated concentration values commence to rapidly rise as represented in general by concentration curve 144. Note that curve 144 rises from the baseline level 140 to a peak concentration represented at dashed line 146. From this peak value represented at line 146, cardiac output may be computed by the above-noted equilibrium method. Note that concentration curve 144 subsequently decays or descends in value as represented at curve portion 148 as the time associated concentration values continue to be sequentially derived. It is this descending curve portion 148 that is employed for the derivation of total circulating blood volume (TCBV) while the area under curve 144 excluding baseline values may be employed for the second or non-equilibrium technique for deriving cardiac output. In general, the analyte will course through the vascular system about every twenty seconds and thus, as curve 144 descends, as represented at portion 148, there is evolved a mixing of the analyte with the blood which is important for derivation of TCBV. Ultimately, the descending portion 148 drops to a level close to or approaching the baseline value as the infused ammoniacal fluid is metabolized by the body. Typically, a new equilibrium level will be established slightly higher than the earlier baseline, as represented by dashed baseline concentration level line 150.

For the present demonstration, about two minutes following the commencement of the infusion interval 142 at time $t_1$, a baseline measurement is carried out and a next infusion, interval represented at cross-hatched rectangle 152 commences as represented at time $t_3$. This second infusion interval 152 continues until time $t_4$, whereupon following a delay, as before, the sensor 114 commences to identify analyte and the sequence of time associated concentration values to define a concentration curve represented generally at 154. As before, concentration curve 154 reaches a peak value 156, whereupon the sequence of time associated concentration values descend in value as represented at curve portion 158. Note that for each of the infusion intervals 142 and 152, a mean time based position, $T_0$, is identified in the figure. The measurement procedure will reiterate over an extensive sequence of hemodynamic parameter measurements. At the end of each infusion interval, the body again reaches a metabolic equilibrium level with respect to the analyte concentration at the newly established baseline concentration level.

Figure 5:
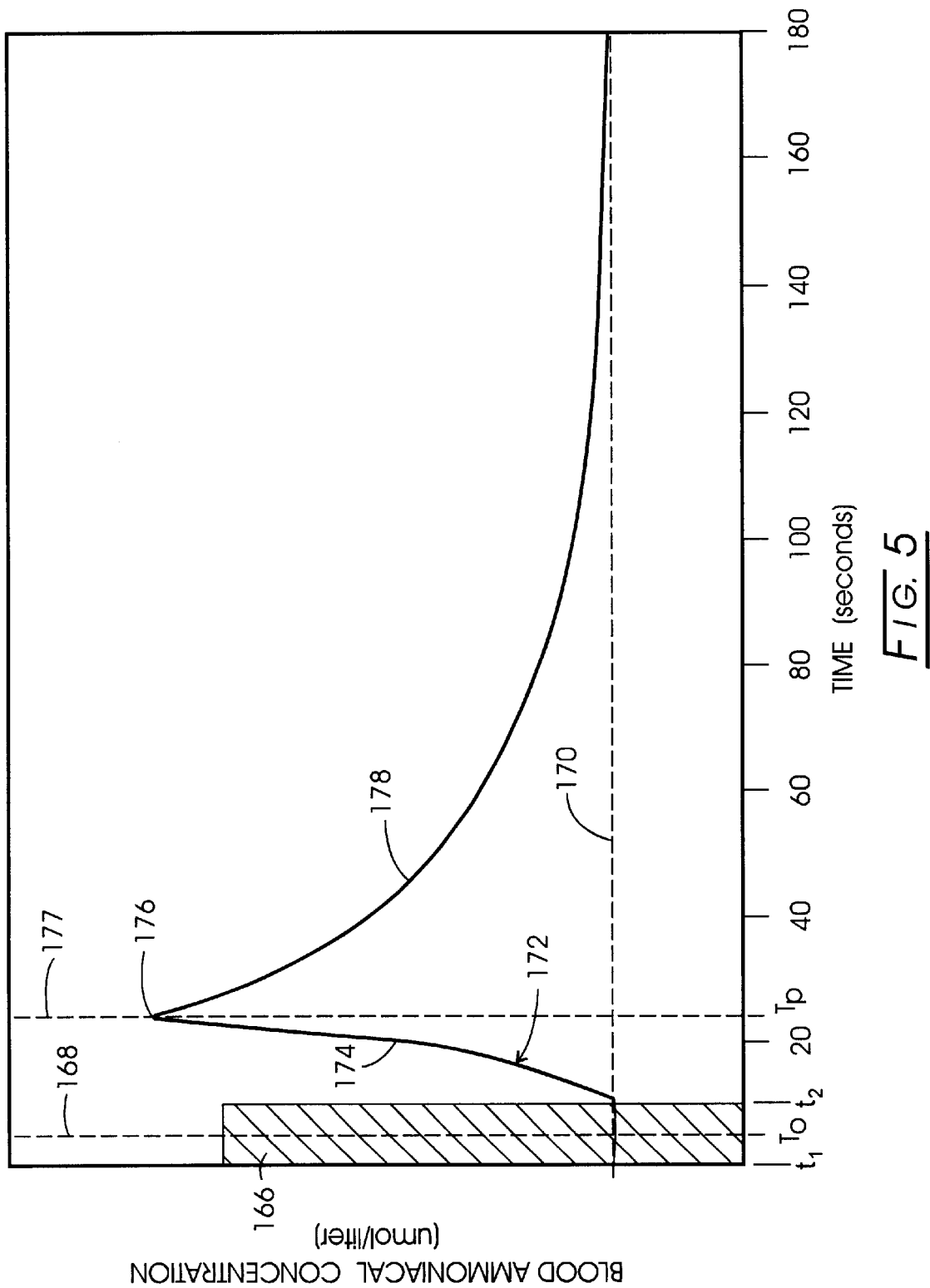
FIG. 5 is a concentration curve developed from the infusion of ammoniacal fluid into an animal, blood ammoniacal concentration being plotted against time.

Referring to FIG. 5, the technique for TCBV measurement is illustrated. As before, the infusion arrangement of FIG. 3 may be employed with a peripheral sensor and, in a preferred embodiment, an ammoniacal fluid may be employed as the infusion injectate. As noted above, the measurement of TCBV is one based upon dosage and a correlative complete mixing of the analyte within the bloodstream. This circulation is somewhat variational, depending upon that portion of the body into which the blood is being pumped and by virtue, for example, of complex neurohumoral mechanisms which affect blood circulation.

FIG. 5 shows an infusion interval represented by cross-hatched rectangle 166. Infusion interval 166 is seen to extend from time $t_1$ to time $t_2$, an interval of about ten seconds. In general, infusion intervals ranging from about two to ten seconds are employed for TCBV measurements. Note, additionally, that the mean time value for the infusion interval is represented at $T_0$ and vertical dashed line 168. Additionally, the baseline analyte or ammoniacal concentration is represented by dashed line level 170. As before, following the infusion interval, the control arrangement associated with sensor 114 commences to compute a sequence of time associated analyte concentration values to define a concentration curve represented in general at 172. As in the earlier demonstration, curve 172 initially will rapidly rise as represented at curve portion 174, reaching a peak 176 at a time $T_p$. That time, $T_p$, is represented in the figure by vertical dashed line 177. As mixing of the analyte with blood continues, the decaying or descending sequence of time associated concentration values defines a curve portion 178. In general, at about forty seconds, an adequate mixing of the analyte in blood is developed by the measurement points defining curve portion 178. Typically, an anomaly will be present in the region of peak 176 as this mixing commences. However, curve portion 178 will be seen to be dominated by the measurement data points or time associated values from the noted elapsed time, for the instant demonstration of about forty seconds. In general, measurements developing the time associated data points are taken in a range of about every one tenth to ten seconds, a typical measurement being each second. Where the infusion interval 166 becomes more extensive in time, a re-circulation effect may be encountered. In this regard, the infused analyte mixes with previously mixed analyte. Thus, the baseline analyte concentration value becomes unstable. Mathematical correction can be made for this effect. It further may be observed that the provision of a predetermined mass flow rate in conjunction with an infusion interval as at 166 develops an analyte concentration dose, which is employed as set forth above in the expression in equation 5.

The derivation of the concentration of the mixed analyte in blood for measuring TCBV is carried out by a regression analysis wherein a least square curve fit is made. Looking to FIG. 6, the time associated concentration data points defining concentration curve 172 are reproduced in conjunction with a semi-log plotting procedure. Note that mean infusion line 168 at time $T_0$ is reproduced, and the time based position of peak, $T_p$ as represented at line 177 reappears. A curve fit for the descending concentration values is represented by line 180 which extends to the mean infusion interval time at dashed line 168. At this elected position, the concentration difference or concentration change, now represented as $\log_e(\Delta C_0)$. occurs as represented at point 182. Note that the earlier-described data point anomaly in the region of the at dashed line 178 is observed as a region represented generally at 184. These data points are ignored with the regression analysis represented at line 180. Note that the sequence of measured and derived time associated concentration values extend to time $T_f$ as represented at dashed line 186. As before, the frequency of infusion intervals, i.e., measurements will be elected by the practitioner and, for example, may be elected from a range of about two to thirty minutes. However, at the end of each infusion interval, the body will reach a metabolic equilibrium level with respect to the analyte concentration. During an initial period of the procedure, those concentrations will be at slightly elevating baseline concentration levels. This occurs until a long-term equilibrium concentration level is reached with essentially no elevation as a final equilibrium of the metabolic activity and the analyte concentration is reached. Where the procedure employs ammoniacal components as the analyte, the peaks in concentration following the infusion intervals will not have a detrimental effect on the body of the patient. In this regard, it may be recalled that the human body will experience ammonia/ammonium ion excursions in the course of exercise as discussed in connection with arrow 54 in FIG. 2. Infusion intervals may be selected from within a broad range of about two to thirty seconds. However, where TCBV is being measured, a shorter interval is desirable to promote more rapid mixing and to avoid the re-circulation effect.

Figure 7:
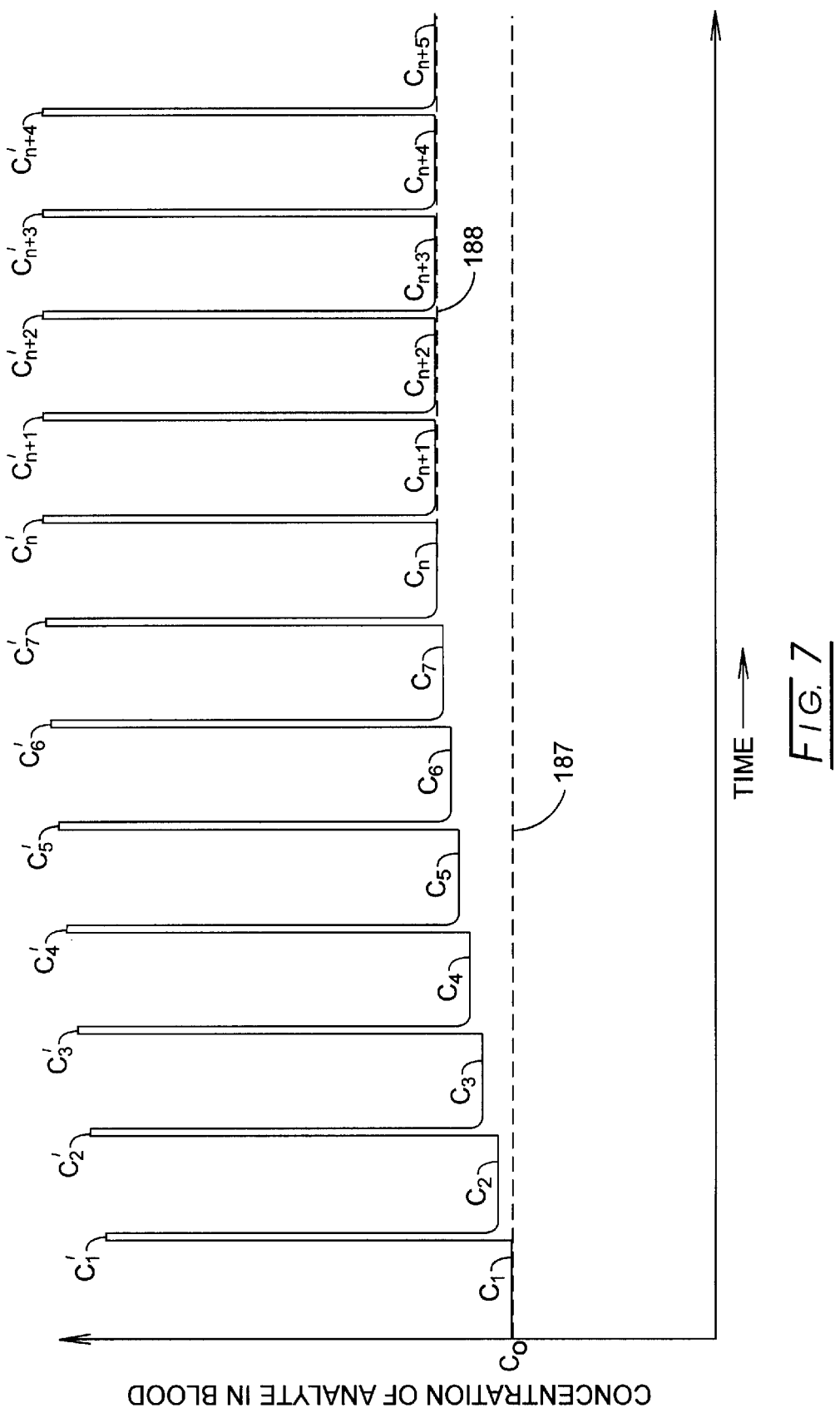
FIG. 7 is a graph schematically relating the concentration of analyte in blood with time and showing the development of a hemostatic level of analyte concentration in blood.

Turning to FIG. 7, a graphical representation of the equilibrium of the analyte concentration in blood with metabolic homeostasis of the body of the patient is provided. In the figure, the concentration of analyte in the blood is represented along the ordinate, while time is represented along the abscissa, such time being associated with a sequence of measurements of the CO or TCBV parameters. The figure shows a sequence of blood analyte concentration spikes $C'_1$ to $C'_7$ and $C'_n$ n to $C'_{n+4}$ which extend upwardly from respective baseline concentration levels $C_1$ to $C_7$ and $C_{n+5}$. In general, the width of each of the spikes corresponds schematically with an infusion interval with an introduction of analyte-containing fluid into the bloodstream of the patient. Note that the baseline blood-analyte concentrations increase with each measurement as represented at baseline values $C_1$ to about $C_7$. During that period of the procedure, a metabolic equilibrium with the analyte concentrations occurs and the concentration values elevate above the initial or initial baseline level $C_0$. That initial level is represented by the horizontal dashed line 187. However, as represented by the horizontal dashed concentration level line 188, a homeostatic level of blood-analyte concentration will be reached following a sequence of infusion based measurements. At this point in the procedure, the average rate of infusion will be equal to the metabolic rate of the patient. This is the analyte concentration level corresponding with metabolic homeostasis of the body of the patient. As part of the instant system, the practitioner may provide as an input to the controls thereof a homeostasis threshold value corresponding with an analyte concentration level which represents a level below iatrogenesis (i.e., a safe concentration level). Where that threshold is exceeded, then the procedure is terminated, and/or a perceptible output, for example, an alarm, is generated to alert the clinician.

Figure 8:
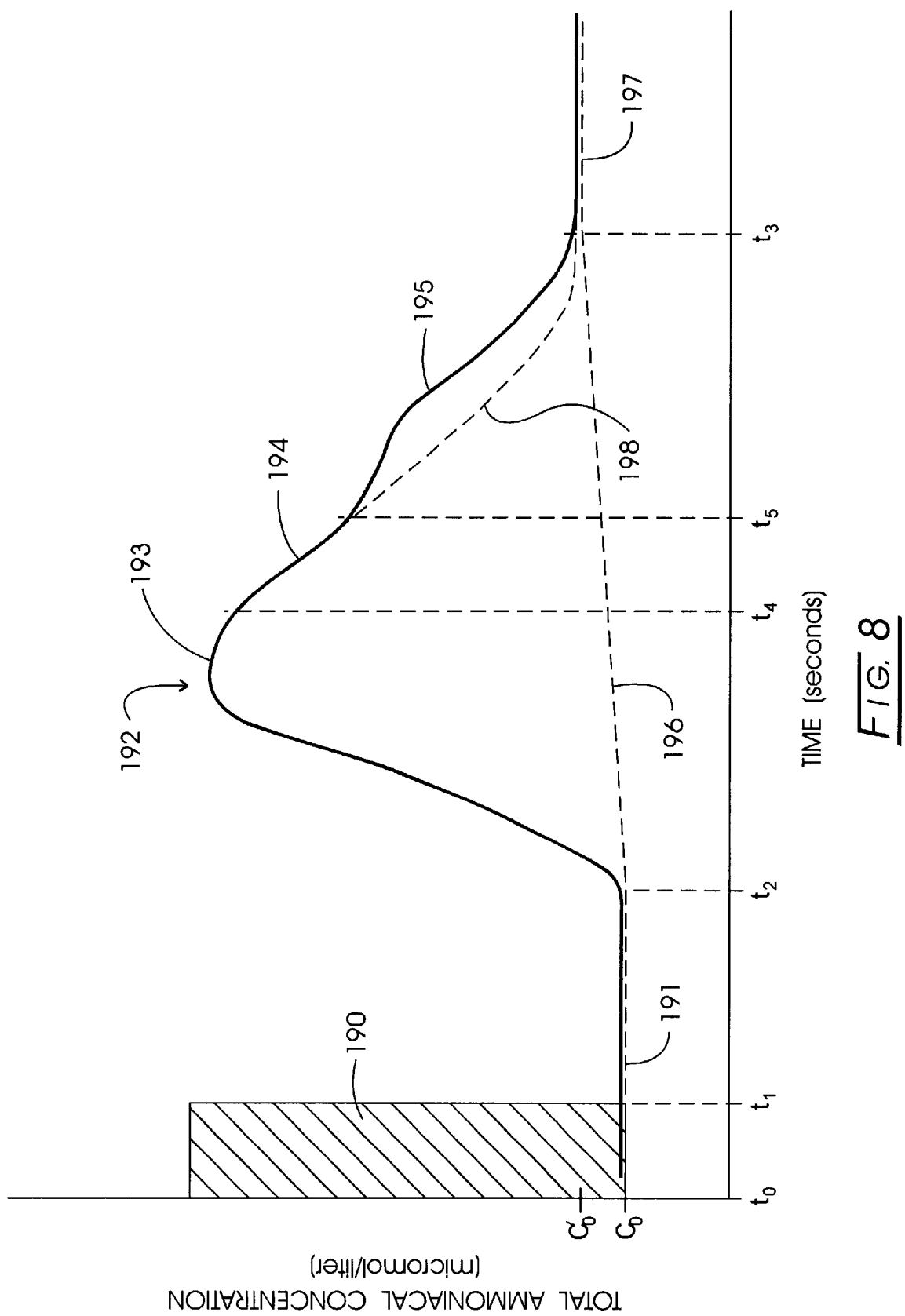
FIG. 8 is a concentration curve plotting total ammoniacal concentration against tine and showing a re-circulation effect.

Referring to FIG. 8, an illustration is provided representing the derivation of cardiac output using the area under the curve or non-equilibrium approach. Re-circulation of the analyte such as ammoniacal concentration is manifested in a variation in baseline level during the development of the concentration curve. Further, an anomaly occurs during the later stages of the decaying component of the curve. In FIG. 8, the infusion interval is represented by a cross-hatched rectangle 190 as occurring between times $t_0$ and $t_1$. The baseline analyte concentration at the commencement of measurement, $C_0$ is represented at dashed line 191. A concentration curve is represented generally at 192. The sharply rising leading edge of curve 192 is seen to commence at time, $t_2$, and reaches a peak 193, whereupon the curve 192 commences to descend in value or decay as represented at curve portion 194. Note, however, that an anomaly defining protuberance 195 commences to occur at time, $t_5$, which continues to the end of the sequence of measurements represented at time, $t_3$. Note, additionally, that the baseline initially represented at dashed line 191 slopes upwardly at line portion 196 between times $t_2$ and $t_3$. A new baseline concentration then exists as represented at the dashed line 197. The area under concentration curve 192 desired for computing cardiac output is that shown utilizing a curve fit represented by dashed line 198 and taking account of the sloping baseline portion 196. Dashed adjusting curve portion 198 is developed by curve fitting at portion 194 above the anomaly 195. Accommodation is made for the varying baseline portion 196 by noting the elevational difference between dashed line 191 and dashed line 197 and either interpolating between those values or by subtracting the triangular-shape defined by extending line 191 to time $t_3$ and treating line portion 196 as a hypotenuse.

In general, re-circulation phenomena depends on parameters such as the infusion interval; the cardiac output rate; the location of the analyte concentration sensor with respect to the point of infusion into the bloodstream and the reaction time or speed of the sensor.

For the preferred CO measurement embodiment employing an ammoniacal fluid as the analyte-containing fluid, for example, employing an infusion based measurement frequency of thirty measurements per hour, or one measurement each two minutes, a preferred ammoniacal salt solution infusion is 0.5 ml per measurement, while a more preferred infusion volume is 1.0 to 2.0 ml per measurement. The ammoniacal concentration of the analyte-containing fluid preferably is 10 mmol/liter to 250 mmol/liter and more preferably is 30 mmol/liter to 120 mmol/liter. For measurement of cardiac output, for higher cardiac output levels, where the amount of dilution of the analyte-containing fluid is greater, the volume of infusion can be greater in order to assure a more accurate measurement. Conversely, at lower cardiac output levels, where the amount of dilution of the analyte-containing fluid is smaller, the volume of infusion can be smaller while still assuring an accurate output measurement.

Table 1 below compares injection rates or infusion rates corresponding to an infusion period of 15 seconds and an analyte concentration of 30 mmol/liter with a variety of ranges of cardiac output, CO, and with respect to a measurement interval which might be elected by the practitioner

TABLE 1

| Previous Cardiac Output Measured Value (liter/minute) | Analyte-Containing Fluid Injection Rate (milliliter/second) | Measurement Interval (minute) |
| --- | --- | --- |
| CO < 3.0 | 0.10 | 2.0 |
| 3.0 ≦ CO < 5.0 | 0.15 | 2.0 |
| 5.0 ≦ CO < 7.0 | 0.20 | 2.0 |
| 7.0 ≦ CO < 9.0 | 0.25 | 2.5 |
| CO ≧ 9.0 | 0.30 | 3.0 |

Using this cardiac output level dependent infusion rate, the amount of analyte-containing fluid infused per measurement can be selected to assure relatively uniform measurement accuracy over the entire range of physiologic cardiac output values, while minimizing the total amount of analyte-containing fluid infused into the body. The measurement interval can be adjusted according to the infusion rate such that during periods of high cardiac output, measurements are performed less frequently to assure that the total amount of analyte-containing fluid being infused over a period of time does not exceed predetermined limits. For instance, while the measured cardiac output level is above 9.0 liters/minute, the measurement interval is 3.0 minutes. At cardiac output levels of 7.0 and lower, the measurement level is 2.0 minutes. This adjustment in the measurement interval assures that the infusion rate does not exceed the ability of the patient's body to metabolize the infused analyte. As is apparent, the continuing and frequent measurement of the analyte concentration level in blood and the selection of the noted threshold homeostasis will assure that such elected safe limits are not exceeded.

During the monitoring of a given patent, the number of measurements carried out by the system may range from less than 50 to greater than 2000. After some number of measurements, the noted homeostatic level represented at dashed line 188 (FIG. 7) is reached when the time-averaged rate of analyte infusion matches the rate of metabolism and the clearance of the injectate from the bloodstream. The body's natural homeostatic process within various organs and tissues serves to increase the rate of metabolism or clearance of the elevated analyte concentration which results from the infusions.

The selection of analyte-containing fluid for CO and TCBV measurements includes balancing the following parameters:

(a) analyte measurement precision—increasing this parameter allows a smaller amount of analyte-containing fluid to be infused to achieve a target measurement accuracy for each measurement.

(b) background or baseline level of analyte-containing fluid—selecting an analyte-containing fluid whose baseline or background is low allows a greater fractional change in the analyte level for a given rate of analyte infusion.

(c) metabolism/clearance rate—selecting an analyte-containing fluid in which the body's rate of metabolism clearance is higher, allows more frequent measurements without significant increase to the baseline concentration and, importantly, without exceeding safe concentration levels within the body.

(d) temporal stability of baseline level of analyte—the greater the short term stability of the baseline concentration of analyte in blood (i.e., during the period between measuring baseline analyte concentration and subsequent analyte concentration during or following the infusion interval which typically may range from several to tens of seconds), the greater the measurement accuracy for a given rate of analyte-containing solution injection (i.e., greater the ratio of signal to noise). This short term stability of the baseline analyte concentration in blood refers to the absence of significant baseline concentration changes due to such transients as: routine infusion of intravenous solutions and medicants; movements of the patient in bed; irregular breathing; and coughing.

(e) response time of sensor—the faster the response time of the sensor, the shorter the duration of infusion of the analyte-containing fluid. The shorter the duration of the infusion, the smaller the amount of analyte-containing fluid infused for each measurement (for target level of measurement accuracy) and the smaller amount of analyte-containing solution that must be metabolized or cleared by the body.

(f) where CO is measured utilizing a peripherally located analyte concentration sensor or TCBV is to be measured requiring a substantial full mixing of the infused analyte throughout the blood volume, then the analyte elected for the procedure should be one which is both biocompatible with and metabolizable by the body but, additionally, should be one whose dilution based signal is not lost by treatment through the lungs. Two such analyte candidates meeting the former category but not the latter, for example, are carbon dioxide and oxygen.

Figure 3:
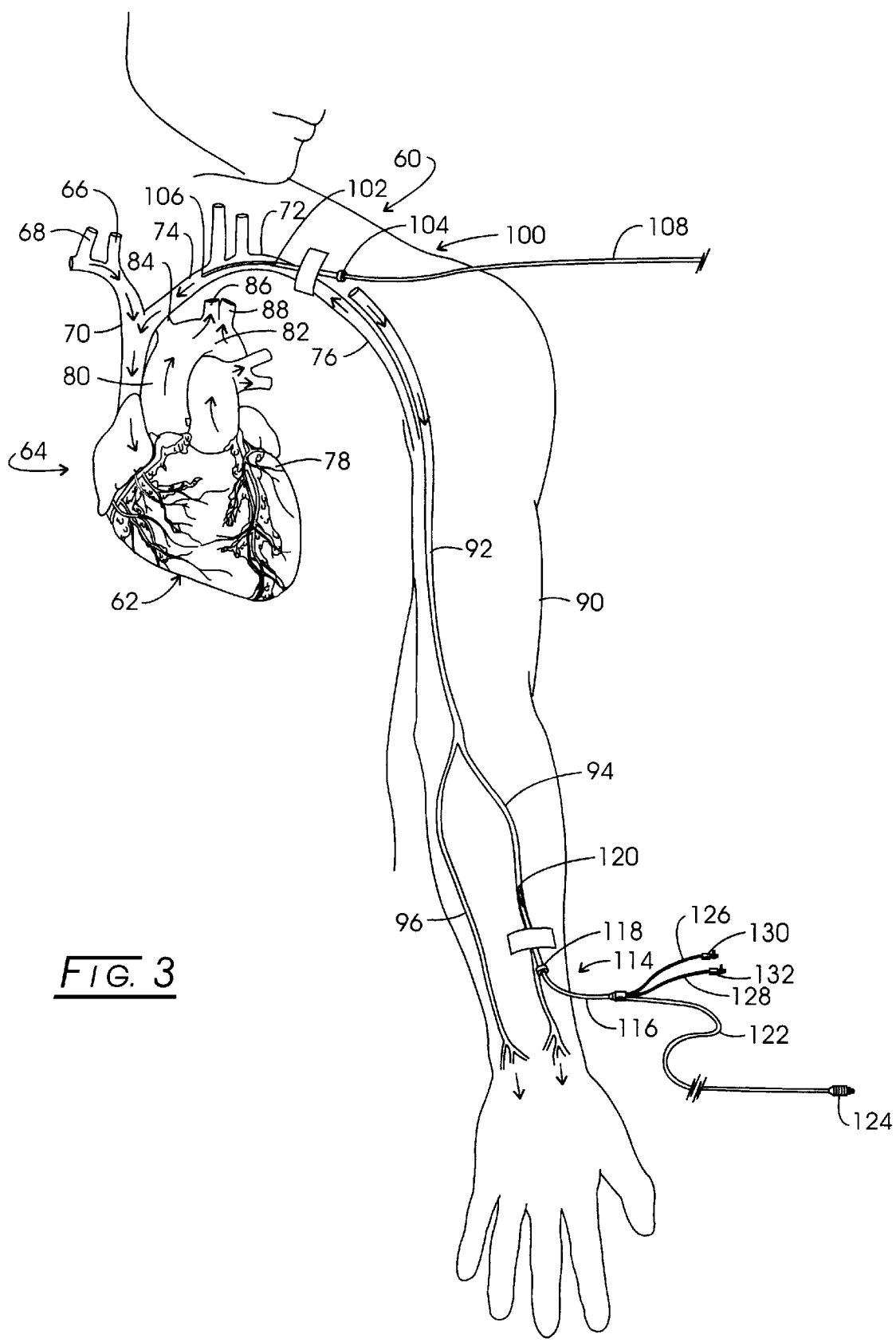
FIG. 3 is a pictorial representation of the upper torso of a patient undergoing hemodynamic parameter measurement according to the invention.
Figure 9:
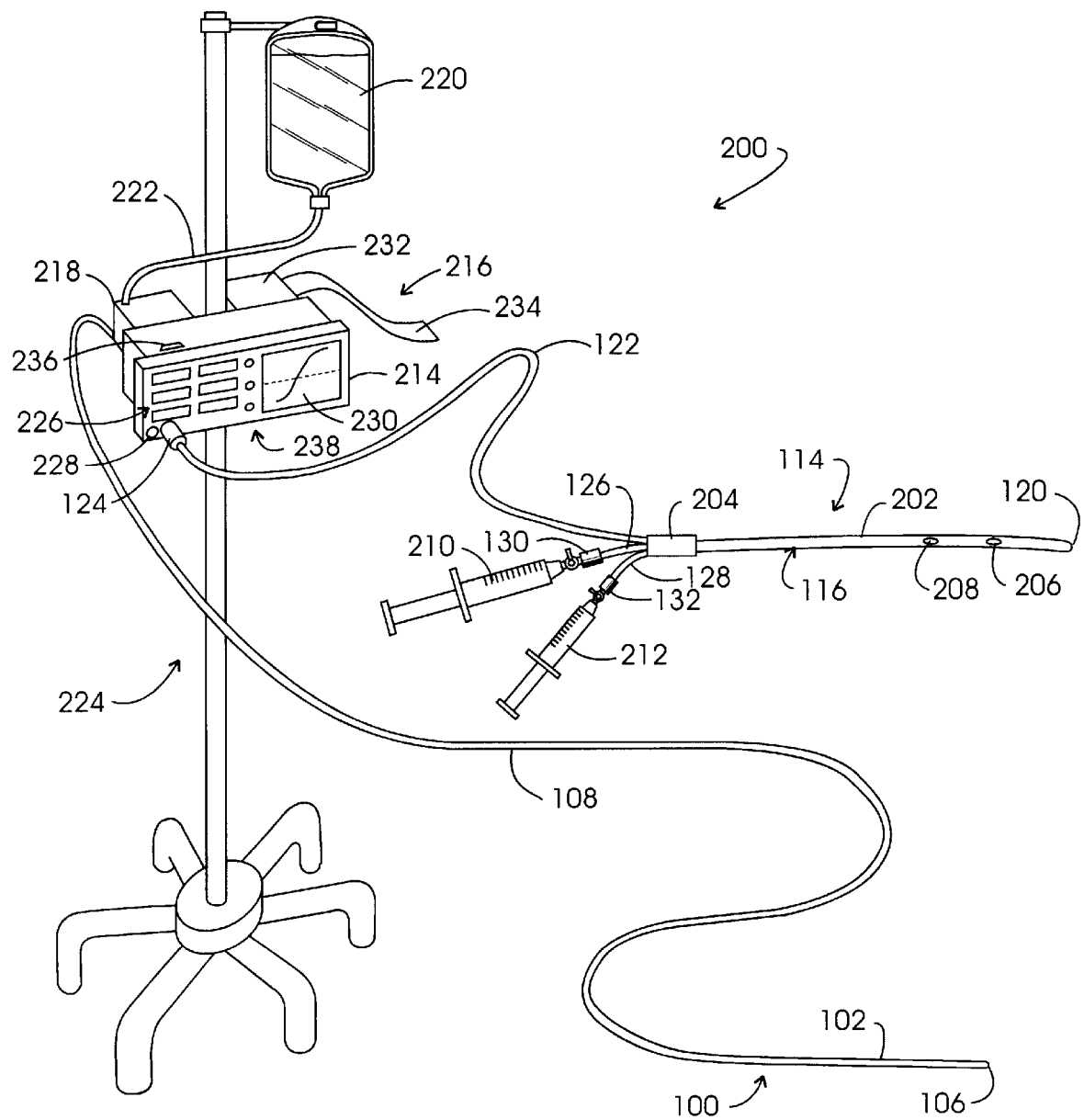
FIG. 9 is a pictorial representation of a system according to the invention.

The delivery assembly 100 and analyte concentration sensor 114 discussed in connection with FIG. 3 are associated in a system, the components of which are represented generally at 200 in FIG. 9. In the figure, analyte concentration sensor 114 reappears with the same numeration, herein implemented within arterial line catheter 116 which includes a flexible polymeric body portion 202 extending from a polymeric base 204. A fiberoptic based analyte concentration sensor as well as a pH sensor are located at the tip 120 of body portion 202. That same body portion includes distal and proximal ports shown respectively at 206 and 208 which are in fluid transfer communication with auxiliary channels within body portion 202 and thence, respectively, to valve/connectors 130 and 132. Connectors 130 and 132 are shown coupled to respective syringes 210 and 212 which function, for example, for withdrawing blood samples, introducing medicants into the bloodstream, and measuring arterial blood pressure (through a fluid column in a lumen or using indwelling pressure sensor). Fiberoptic control cable 122 is seen extending to the optic coupler 124, which, in turn, is coupled at the instrumentation panel 214 of a controller 216. Delivery assembly 100 also is implemented as a simple, single channel catheter, the delivery conduit 108 from which extends to the fluid transfer output of an infusion pump 218 mounted upon and controlled by controller 216. Delivery assembly 100 may optionally include additional lumina and connectors as illustrated in analyte concentration sensor 114 for introducing fluids or medicants into the bloodstream. Analyte-containing fluid is supplied to the pump 218 from a disposable hanging bag source 220 and conduit 222. The controller 216 as well as source 220 are mounted upon a conventional IV pole or stand represented generally at 224. The controller 216 includes an array of keys represented generally at 226 which are utilized for entering or inputting control parameters such as the type of sensor utilized; total ammoniacal concentration threshold levels and rate of rise thresholds as well as a pH value where no sensor is employed for that measurement. Additional connectors, one of which is represented, for example, at 228 may be provided below the key array 226 to accommodate for different forms of analyte concentration sensors. A display is shown at 230 having a graphical readout with respect to time, as well as numerical readouts. A permanent record or data log may be printed with the system via a printing assembly 232 providing a strip-type paper readout 234. A serial input/output port 236 is mounted on upon the upper surface of the controller 216. The controller 216 also may supply aural cues to the practitioner indicating an alarm or warning condition. Visual cueing is provided, for example, by light emitting diodes (LEDs), three of which are shown in general at 238.

Figure 10:
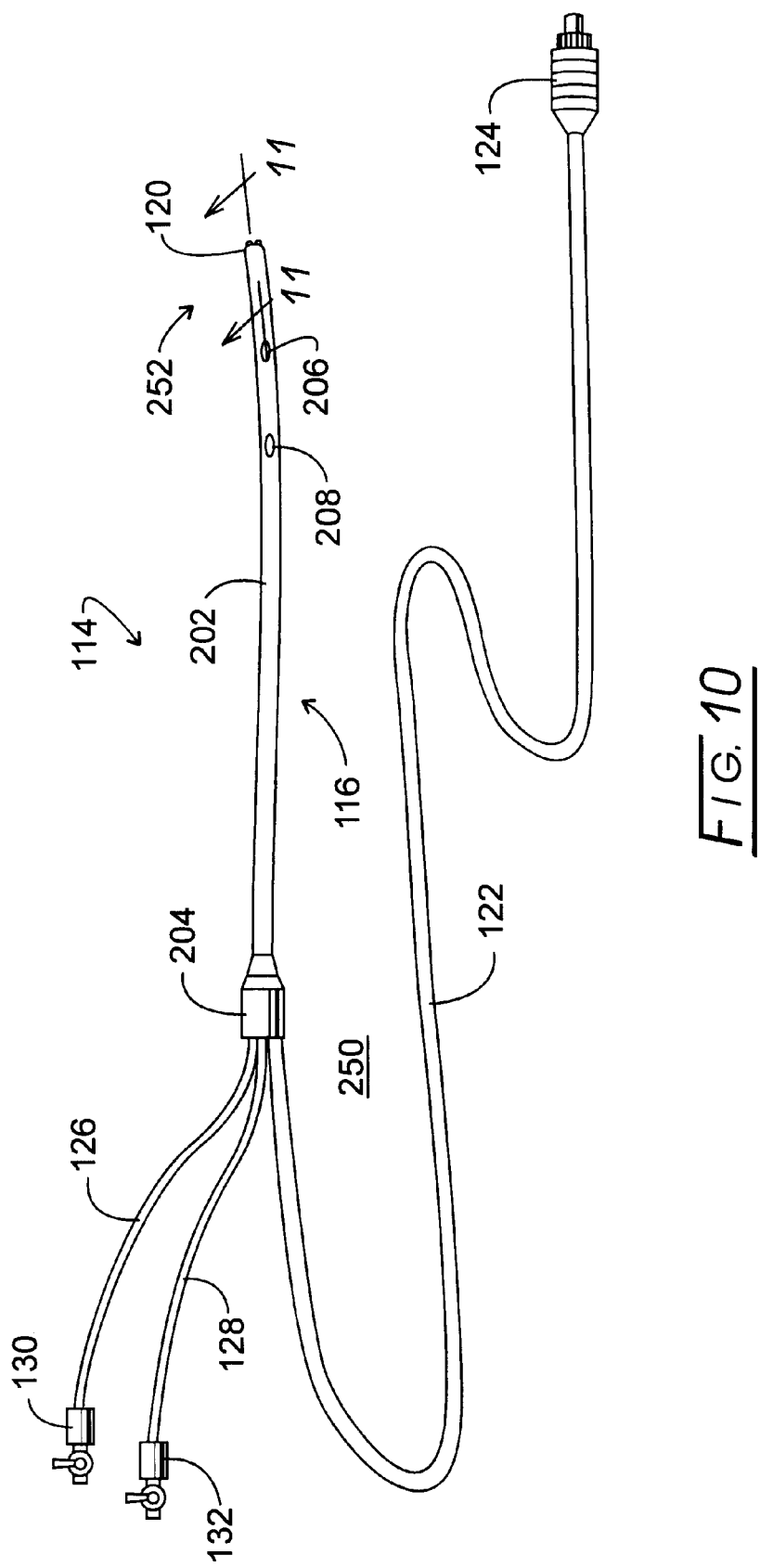
FIG. 10 is a pictorial view of a catheter assembly employed with the system and method of the invention.

Referring to FIG. 10, the analyte concentration sensor 114 as it is implemented with line arterial catheter 116, is revealed at a higher level of detail. The catheter 116 is configured for insertion within the bloodstream of the vascular system located in a peripheral region of the body, as discussed in connection with FIG. 3. Where excessive blood hydraulic impedance is encountered, the sensing components carried by the catheter 116 may be extended into the brachial artery. Body portion 202 of the catheter 116 extends from base 204 within a relatively extended proximal region represented generally at 250 to a measurement region represented generally at 252 extending, in turn, to tip 120. Located within the measurement region 252 and, preferably, extending slightly forwardly from tip 120 are two fiberoptic based sensors formed within fiberoptic channels which extend to base 204 for continuous communication with fiberoptic cable 122 terminating in fiberoptic connector 124.

Referring to FIGS. 11 and 12, the structure of catheter 116 at its measurement region 252 is revealed in sectional fashion. Additionally, in the former figure, signal treating aspects of a controller as at 216 (FIG. 9) are represented in general at 254. In general, the body portion 202 of the catheter assembly 116 is formed of a medical grade polymeric material which is slightly flexible, permitting sufficient flexure for facile insertion through an introducer as at 118 (FIG. 3) into a vascular vessel for contact of a measurement region 252 with the bloodstream. The polymeric body portion 202 is shown having an outer cylindrical surface 256. Formed typically by extrusion, extending through the body portion 202 is a first sensor channel 258 which extends from the base 204 (FIG. 10) to tip 120 and which serves to support an ammoniacal component sensor assembly represented in general at 260 and seen to be comprised of a fiberoptic strand 262 extending to an ammoniacal component responsive forward assembly represented generally at 264. Assembly 264 includes the confronting face or tip surface 266 of the fiberoptic strand 262 which is seen to be extending slightly forwardly of the forward surface 268 of the body portion 202 of catheter 116. Forward assembly 264 further includes a membrane 270 which, inter alia, forms a blood confronting surface of an ammoniacal component concentration reactor which may take a variety of configurations. For example, the elective ammoniacal component may be ammonia ($NH_3$) and the reactor may be selected to be a gaseous ammonia sensitive dye which may be captured by the membrane either by admixture therewith or by encapsulating the dye intermediate the membrane 270 rear face and the forward face 266 of the fiberoptic strand 262. For the former approach, the dye is deposited upon the membrane surface for migrating into its pore structure. This approach has been observed to improve response time. With the above arrangement, the fiberoptic strand 262 functions as a transmission assembly for conveying a signal corresponding with the output condition of the reactor along the body portion 202 to connector 124 (FIG. 10).

Positioned diametrically opposite the first sensor channel 258 is a second sensor channel 272, again extending from the forward surface 268 of body portion 202 to the base 204 (FIG. 10). Sensor channel 272 functions to support a pH sensor structure represented generally at 274. Structure 274 includes a pH responsive forward assembly represented generally at 276 which is formed including the forward portion of a fiberoptic strand 278, the forward face 280 of which is seen to protrude slightly from forward surface 268 of catheter body portion 202 at tip 120. Forward assembly 276 of the sensor structure 274 may assume a variety of configurations for carrying out in vivo measurement of pH. In this regard, typically, a pH-sensitive indicator is immobilized on the face 280. Light energy of selected wavelength is guided along fiberoptic strand 278 to excite the indicator which then fluoresces and a resultant emission intensity is a function of the pH of blood within the bloodstream. To provide the forward assembly structure 274, the face 280 supporting the indicator is covered with a hydrogen ion permeable membrane represented at 282 which is impermeable to the other constituents of blood.

Looking to sectional FIG. 12, the distal auxiliary port 206 is revealed in fluid transfer communication with an auxiliary channel 284. Channel 284 ultimately resides in fluid transfer communication with tube 126 extending from base 204 (FIG. 9). In similar fashion, an auxiliary channel 286 extends from base 204 to the proximal port 208 (FIG. 9). The channel is blocked intermediate ports 208 and 206 and extends to base 204 and thence to tube 128 (FIG. 9).

Returning to FIG. 11, the fiberoptic component of ammoniacal sensor assembly 260 and pH sensor assembly 274 extend to signal treatment components 254 as represented at blocks 286 and 288. Cable 122 (FIG. 9) is symbolically represented by dual arrows 290 and 292, the former extending from the ammoniacal sensor assembly 260 and the former from the pH sensor assembly 274. The signal treatment function represented at block 286 includes a light source (LS) and a transducing (T) network 294, the interactive operational association with arrow 292 being represented by arrows 296 and 297. In similar fashion, arrow 290 is seen to be operationally associated with a light source (LS) and transducing M network 300, the interactive operational association with arrow 290 being shown by arrows 301 and 302. For the fiberoptic embodiment shown, networks 294 and 300 function to interrogate the reactor component of forward assemblies 276 and 264 to provide an analog signal at outputs represented at respective lines 304 and 306. These analog signals then are converted to digital form as represented at the analog-to-digital conversion function represented at block 288. The resultant digital data then is submitted for processing as represented by arrow 308.

While the auxiliary channels 284 and 286 of the catheter 116 are structured for the transmission of fluid substances or measurement of intravascular pressure, they also can be configured to support an additional sensing arrangement. For example, such a channel may carry a third fiberoptic assembly which is coextensive with sensor assemblies 260 and 274. This third channel, for example, may be employed to measure oxygen saturation level of the blood. Such measurements may be performed using reflectance oximetry methods as are described in the following publication:

Schweiss, J. F., "Continuous Measurement of Blood Oxygen Saturation in he High Risk Patient", Vol. 1, *Beach International, Inc.*, San Diego, Calif., pp 1–12 (1983).

The type of sensor technology employed with the instant system and method is selected in compliment with the analyte-containing fluid utilized. Where optically-based techniques are employed, a variety of categories for the sensors are available. In all cases, however, the forward assemblies of the sensor systems must be within flowing blood as opposed to being located in cavities or the like where the blood may be captured and held quiescent. Forward facing optical sensors preferably are situated in the bloodstream such that the flowing blood confronts them, as opposed passing over the tips from a rearward location. Additionally, for positioning in the bloodstream at the peripheral regions of the body, it is desirable that the sensor structures be of small widthwise extent so as not to evoke blood hydraulic conditions wherein the blood flow will branch to an unobstructed blood carrying vessel. Such small, minimally obstructive-sizes for the sensors have particular application, for example, in the monitoring of the cardiovascular systems of infants or children. In general, the optical sensors include: direct spectrometric sensors; indirect spectrometric sensors; transmission spectrometric sensors; transmission/reflectance spectrometric sensors; colorimetric sensors; and fluorometric sensors. These sensors are described in conjunction with schematic representations of them in the figures to follow.

Figure 13:
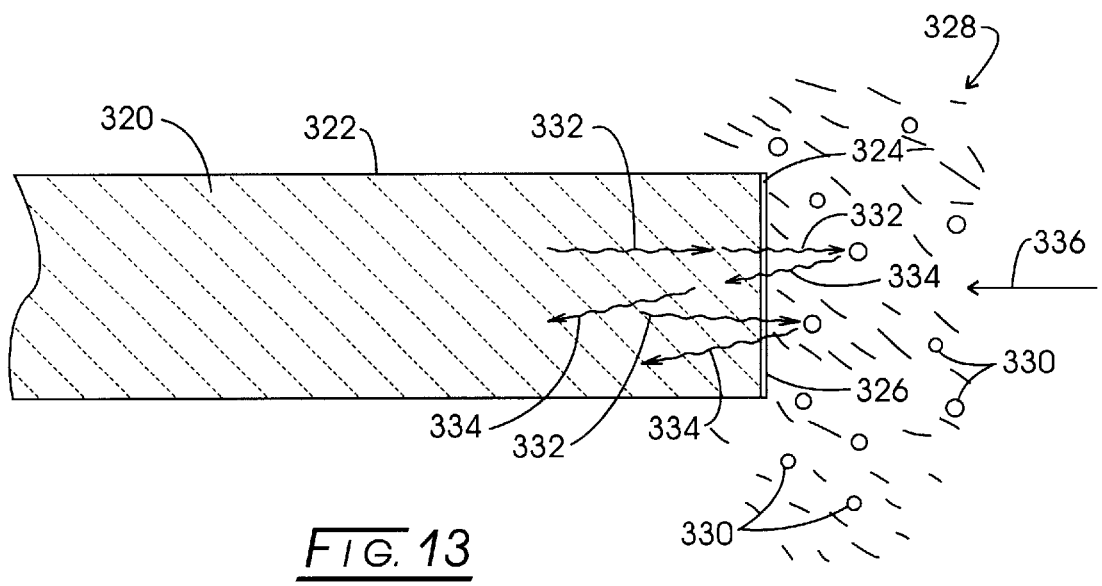
FIG. 13 is a schematic representation of a front end assembly of a concentration sensor employed with the invention.
Figure 14:
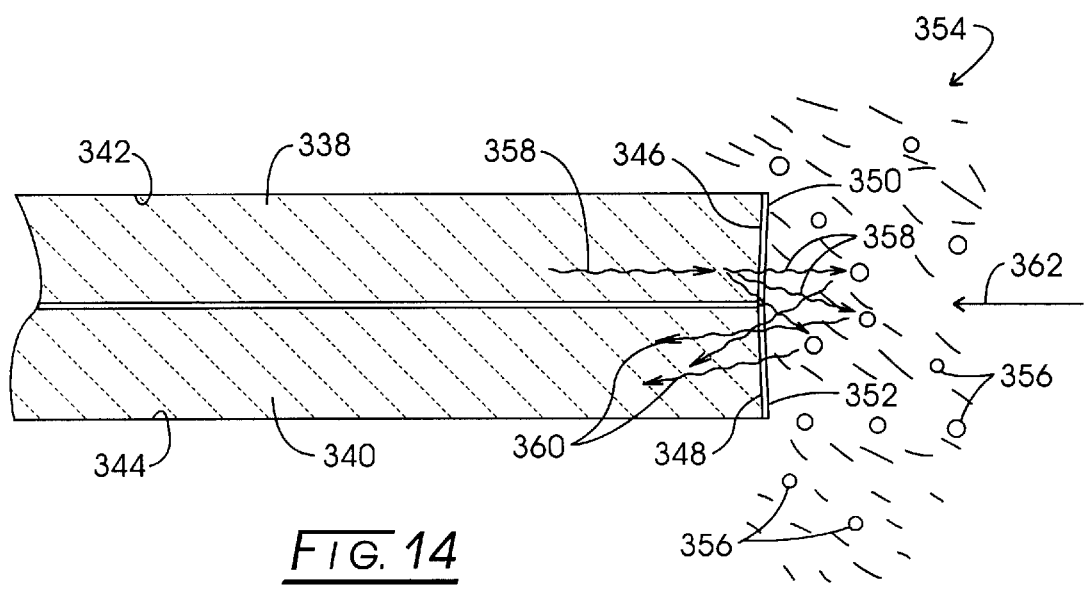
FIG. 14 is a schematic representation of the front end assembly of a concentration sensor which may be employed with the invention.
Figure 15:
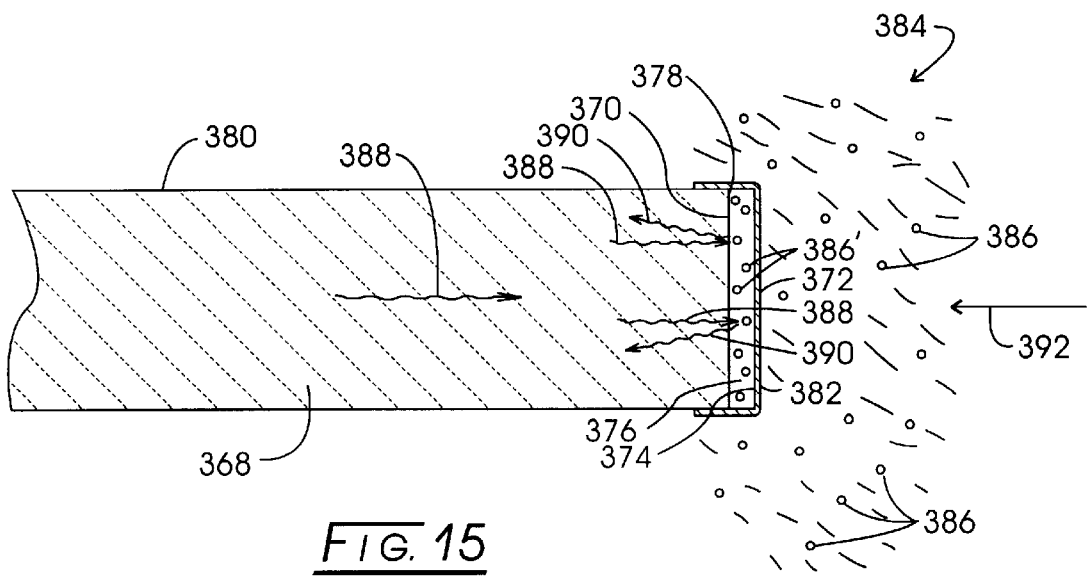
FIG. 15 is a schematic representation of a membrane containing front end assembly of a concentration sensor which may be employed with the invention.

Considering initially the direct spectrometric sensors, reference is made to FIGS. 13 and 14. In FIG. 13, the forward assembly of an analyte concentration sensor is revealed. This sensor may, for example, directly measure ammonia gas as the analyte component of interest. With this arrangement, an optical fiber or strand 320 is employed. This optical fiber 320 is supported within some form of sensor channel, for example, that described in 258 in connection with FIGS. 11 and 12. The fiber 320 is surrounded along its lengthwise extent by a sheath 322 while its tip or forward face 324 is coated with a very thin, optically transparent coating 326. Coating 326 is an anti-coagulant such as heparin which functions to reduce the possibility of deposits such as fibrin or blood coatings over the tip 324. The embodiment of FIG. 13 is one wherein there is a simultaneous transmission of light at one or more predetermined wavelengths and reflectance reception of that light. In this regard, the bloodstream is schematically represented in general at 328. For the preferred embodiment the ammonia gas ($NH_3$) component of the analyte is sensed. Molecules of that gas are represented at 330. Analysis of the concentration of this gas is made by light transmission to and reflectance from the ammonia gas particles 330. Light transmission is schematically represented in the figure as wave arrows 332, while reacting reflectance or reflections are represented by wave arrows 334. This latter reflective illumination as represented by the arrows 334 will exhibit a spectrum which is characteristic of the ammonia component and the intensity of the spectral portions thereof will be related to the concentration of ammonia within the blood 328. As noted above, it is preferred that the face 324 of the forward assembly confront the direction of blood flow as represented by arrow 336. In general, the diameter of the fiberoptic component 320 will be in the range from about 50 to 1000 microns and preferably falls at a range of about 100 to 500 microns. A typical diameter for catheter applications will be about 250 microns.

Transmission and reception of investigatory light at one or more predetermined wavelengths also may be carried out using two or more fiber components. In one approach, two fiber components are positioned in immediate adjacency. Alternately, one fiberoptic component may provide a transmission aspect while a group of such fiber components surmounting a central transmission fiber component carries out the opposite or reception function. In such an arrangement, the transmitted light and reflected or emitted light are advantageously separated during their transmission to and from the blood. In FIG. 14 a forward assembly of an analyte concentration sensor is depicted. The fiberoptic assemblies employed with the optical sensor may be singular fibers or strands which are typically formed of plastic or when formed of glass, typically are provided as bundles or multiple strands of glass. In the instant figure, two optical fibers are schematically represented at 338 and 340. The lengthwise extent of each of these fibers is enclosed within a sheath as represented, respectively, at 342 and 344. Tip surfaces or faces of respective fibers 338 and 340 are configured such that the tip surface 346 is slightly canted axially inwardly as is the opposite surface 348. Tip surfaces 346 and 348 additionally may be coated, as represented respectively at 350 and 352, with an optically transparent anti-coagulant such as heparin. The overall diameter of the transmission/reflection separated assembly will be selected as the same as the overall diameter of the single fiber arrangement of FIG. 13. In the instant figure, the bloodstream is represented in general at 354 and the ammoniacal component, ammonia gas ($NH_3$), is represented for instance, at 356. With the arrangement shown, light of one or more wavelengths is transmitted through fiber assembly 338 as represented by the transmission wave arrows 358. Resultant reflection, as represented by the transmission wave arrows 360 is collected and transmitted by fiberoptic assembly 340 for analysis. With this sensing forward structure, the transmitted light and reflected light are advantageously separated during their transmission to and from the bloodstream or blood 354. In general, this enables a more accurate quantitative measurement of spectral intensity and, in turn, a more accurate measurement of the concentration of ammonia ($NH_3$) as represented at 356. It may be noted, by way of example, that the direct measurement arrangement of FIGS. 13 and 14 may be used to measure both ammonia ($NH_3$) concentration as well as the oxygen saturation level of the blood. Particularly for the catheter borne sensors, the tip surfaces of the forward assemblies and their associated coatings preferably are oriented to directly confront the direction of flowing blood in the bloodstream as represented by arrow 362. This generally reduces the interval required to evoke a valid measurement and assures an appropriate contact of the blood flow against the forward faces of the sensors forward assemblies.

Figure 16:
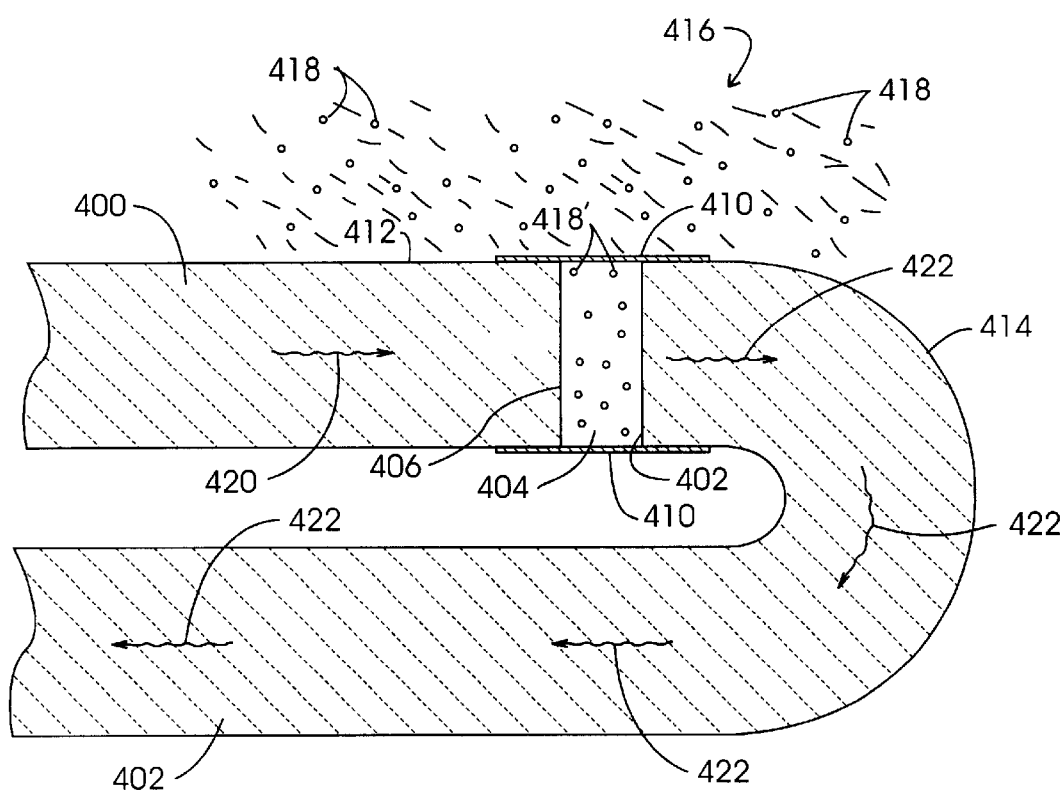
FIG. 16 is a schematic representation of a membrane containing front end assembly of a transmission-type concentration sensor which may be employed with the invention.

Now considering indirect spectrometric sensor technology, reference is made to FIGS. 15, 16, 17A and 17B. In FIG. 16, the forward assembly of a sensor is seen to include a fiberoptic transmission/reception assembly 368 which extends to a tip surface or face 370. Positioned over the tip surface 370 is a cap-shaped membrane 372 having a forward inner surface portion 374 which is spaced from tip surface or face 370 to define a gap 376. A peripheral inner surface 378 of membrane 372 is sealed to the outer surface 380 of fiberoptic assembly 368 to assure the integrity of the gap 376. The outer surface 382 of the membrane 372 is in contact with blood or flowing blood of the bloodstream represented generally at 384. As before, mixed with blood of the bloodstream 384 is an analyte component, for example, ammonia gas, molecules of which are represented at 386. Membrane 372 is structured to contain microscopic pores and functions to minimize or block the ingress of water and other components within the blood 384 while permitting the analyte component of interest, i.e., ammonia gas, to rapidly diffuse across it due to a developed concentration gradient. In effect, a fluid space is developed at the gap 376 containing the measured analyte component as represented at 386'. With the arrangement, an equilibrium develops between the analyte component 386' and analyte component 386, here shown as ammonia gas ($NH_3$). One or more wavelengths of light as represented by the transmission wave arrows 388 are transmitted into gap 376 and reflections from the analyte component 386', as are represented by transmission arrows 390, may then be analyzed. The concentration of the analyte component is correlatable with the intensity of light represented by arrows 390 at one or more wavelengths. Light transmitted, as represented by arrows 388 may be of specific wavelength or a spectrum of wavelengths may be employed. The advantage of this sensor structuring resides in the simplification of spectral analysis, inasmuch as the species of interest has been separated from other blood-carrying species. Membrane 372 as well as the membrane employed with other embodiments of sensors according to the invention may be provided as a Teflon® barrier, for example, manufactured by W. L. Gore & Associates, Inc. of Elkton, Md. These membranes contain microscopic pores whose size, for the ammonia analyte component, preferably is in the range from 0.02 to 3 microns. The overall thickness of the membrane 372 will be in the range of from about 1 to 200 microns and, preferably, in the range of about 10 to 75 microns. The hydrophobic nature of the Teflon® material serves to minimize ingress of water and other liquid components within surrounding blood. As before, it is preferred that the forward face or outer sensing surface of the sensor forward assembly confront the direction of flow of the bloodstream 384, such direction of flow being represented in the figure by arrow 392. For a number of applications of the system, this calls for positioning of measurement region of the sensor assembly at the tip of the supporting device such as a catheter.

The forward assembly of a transmission spectrometric sensor is schematically illustrated in FIG. 16. In the figure, the fiberoptic assembly is seen to have a generally U-shaped configuration with a light transmission leg 400 and a return leg 402. Within the assemblage there is, as in the case of the device of FIG. 15, a gap 404 defined between the end face 406 of transmission leg 400 and the end face 408 of return leg 402. A surmounting membrane 410, which may be of cylindrical shape, is positioned across the gap 404 and sealed against the outer surfaces 412 and 414 of respective legs 400 and 402. As before, the membrane 410 is configured having microscopic pores which permit the ingress of analyte components from the blood or bloodstream. In this regard, such blood or bloodstream is represented in general at 416 and the analyte components, for example, ammonia gas ($NH_3$) are represented at 418. With the arrangement, when the sensor forward assembly is immersed within the flowing bloodstream, a concentration gradient builds between blood 416 and the gap 404 to provide for the migration of analyte component into the latter, such analyte component being represented at 418'.Light having one or more wavelengths is transmitted toward the gap 404, as represented by transmission wave arrow 420 to be attenuated by the analyte component 418'. The thus attenuated light then is returned for analysis as represented by wave arrows 422. Such analysis quantifies the concentration of analyte component (ammonia gas) in the gap 404 and, hence, in the bloodstream 416. As in the case of FIG. 15, this arrangement has the advantage of isolating the analyte species of interest to simplify analysis. No blood directional arrows are shown in the instant figure, inasmuch as this forward assembly may additionally be utilized at locations spaced rearwardly from the tip of a supporting catheter or the like.

Figure 17A:
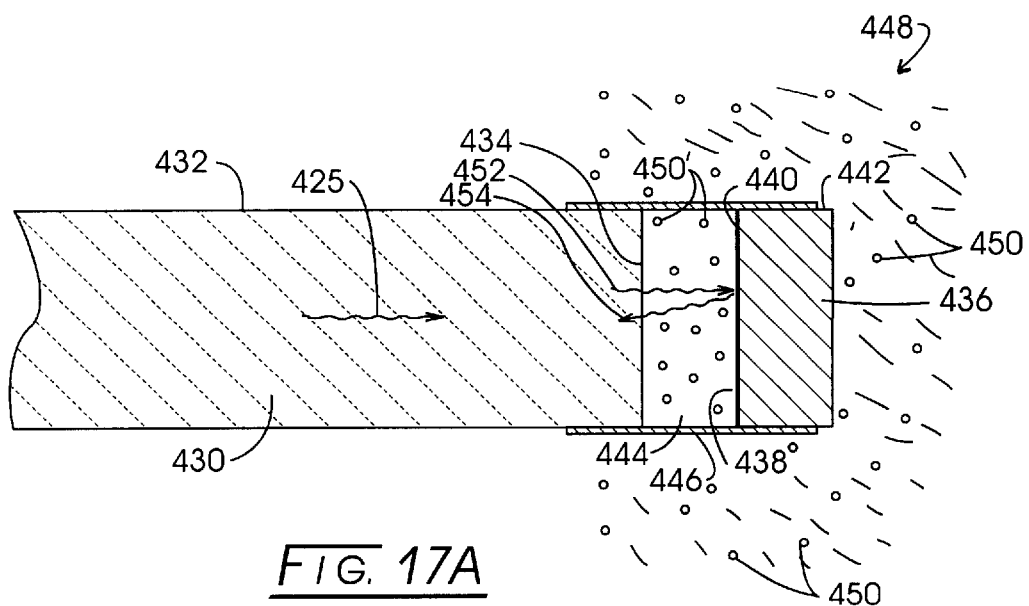
FIG. 17A is a schematic representation of a front end assembly of a concentration sensor which may be employed with the invention.
Figure 17B:
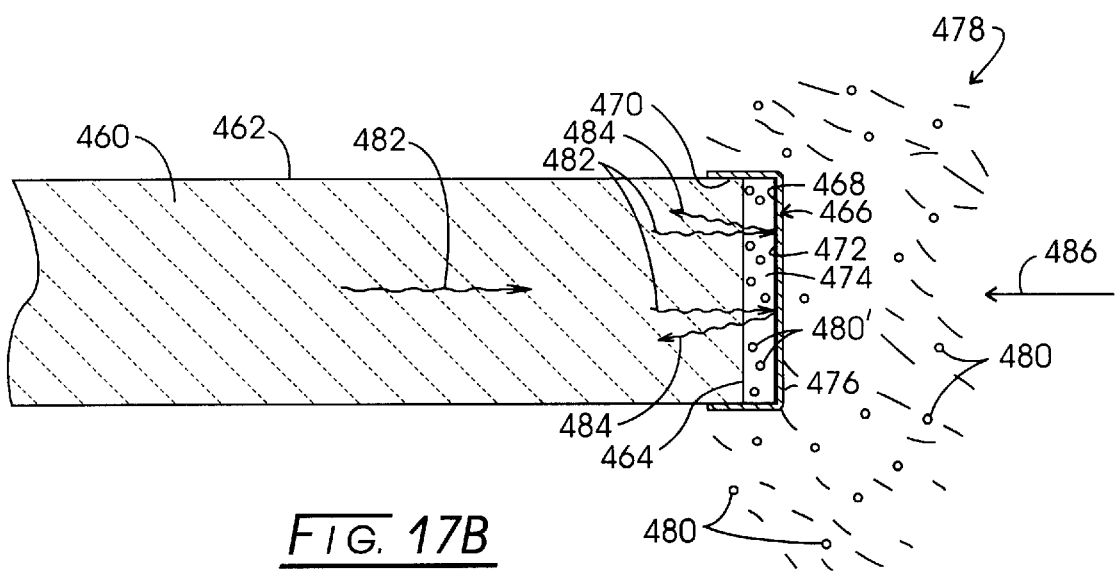
FIG. 17B is a schematic representation of a front end assembly of a concentration sensor which may be employed with the invention.

Schematic representations of transmission/reflectance spectrometric sensors are provided in FIGS. 17A and 17B. Looking to FIG. 17A, a sensor forward assembly is seen to comprise an optical fiber assembly 430, here shown as a single strand, which has a surface 432 and which extends to a tip surface or face 434. Spaced from the face 434 is a polymeric end piece 436 having an inwardly disposed surface 438 which supports a light reflector provided as a coating or the like seen at 440. The edge surface 442 of end piece 436 is dimensioned in correspondence with the diametric extent of surface 432 of the assembly 430.

The light reflecting surface provided by coating 440 is spaced from tip face or surface 434 a distance defining a gap 444 and a cylindrical membrane 446 is seen to surround and further define gap 444. In this regard, membrane 446 is sealed to the surfaces 432 and 442. The sensor forward assembly is immersed in the blood or bloodstream represented in general at 448. Mixed with the bloodstream 448 is an analyte component, for example, ammonia gas ($NH_3$) as is represented at 450. With the arrangement, a concentration gradient is developed between the bloodstream or blood 448 and the gap 444 and the microstructure of the membrane 446 permits a migration of that analyte component into the gap 444 as represented at 450'. Light is transmitted along the assembly as represented by the wave transmission arrows as at 452, whereupon it is reflected from the light reflecting surface provided by coating 440 and returned as represented by wave transmission arrow 454. The interaction of this light with analyte component 450' in crossing the gap 444 then is analyzed to develop values for the concentration of the analyte component The sensor configuration of this embodiment is, for example, suited for employment within catheter-type structures wherein the sensor is located rearwardly from the tip of the placement instrument.

Referring to 17B, an alternative structuring for the transmission/reflectance spectrometric sensor is revealed. The forward assembly of this sensor is seen to be structured incorporating a fiberoptic assembly, here represented as a fiberoptic strand 460. Assembly 460 is formed having an outer surface 462 and extends to a tip surface or face 464. Positioned over the forward end of the fiberoptic assembly 460 is a cap-configured membrane represented generally at 466 having an inwardly disposed surface 468 and a peripheral, cylindrically-shaped inward surface 470. Supported by the inwardly-disposed surface 468 is a light-reflecting component present as a coating and shown at 472. The peripheral inward surface 470 of the membrane 466 is sealed to the surface 462 of fiberoptic assembly 470 to define a gap 474. Outwardly disposed surface 476 of membrane 466 is immersed in blood or bloodstream as represented in general at 478. As before, the membrane 466 is configured having microscopic pores permitting the migration of the analyte component such as ammonia gas 480 into the gap 474 by virtue of the evolution of a concentration gradient between the gap 474 and blood 478. Other components of the blood essentially are blocked from movement into the gap 474. Analyte component which has migrated into the gap 474 are represented at 480'. Analysis of the concentration of this analyte component 480', which is equilibrated with the corresponding concentration of analyte component 480, is made by directing light at one or more wavelengths across the gap 474 is represented by transmission wave arrows 482. This light interacts with the analyte component 480' and is reflected from the reflector formed by coating 472 to return for analysis as represented by reflection wave arrows 484.

With the sensor geometry shown and where the sensor is positioned within a peripheral region of the vascular system, it is desirable that the forward surface 476 of membrane 466 be positioned to confront the direction of flow of the bloodstream as represented at arrow 486.

Figure 18:
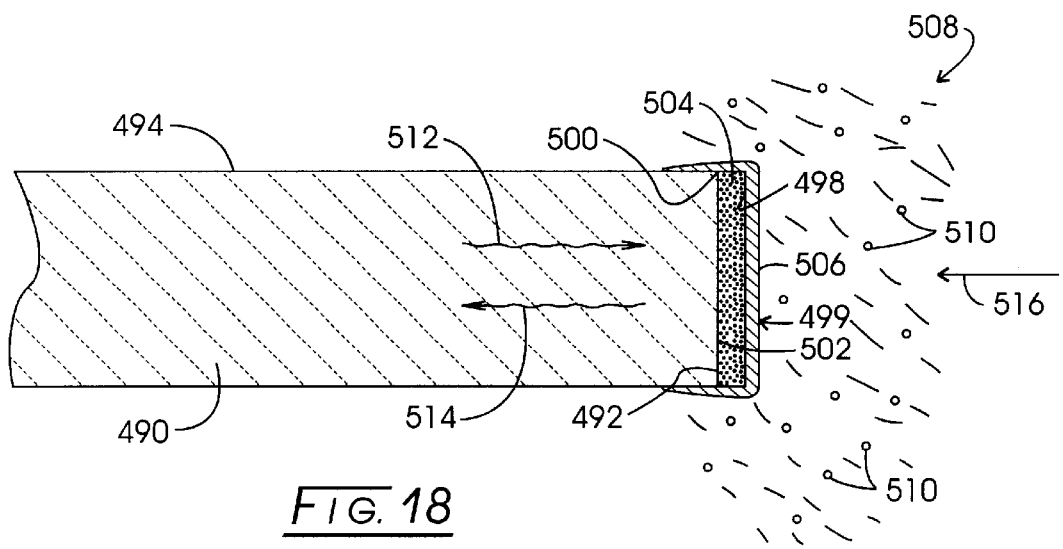
FIG. 18 is a schematic representation of a front end assembly of a concentration sensor which may be employed with the invention.

Referring to FIG. 18, a sensor forward assembly is illustrated schematically which has a structure common to both colorimetric and fluorometric sensors. The sensor arrangement includes a fiberoptic assembly 490 implemented as a single fiberoptic strand which extends to a tip surface or face 492 and is surrounded by a sheath 494 at its outer surface. Mounted over the sheath 494 and fiberoptic assembly 490 is a cap-shaped membrane represented generally at 496 having an inwardly disposed surface 498 and an inwardly-peripherally disposed surface 500. Surface 500 is sealed to the outer surface of sheath 494 in a manner spacing the inward surface 498 from the tip surface or face 492 a distance defining a gap 502. Located within this gap is a reactor 504 which, for the structure shown, may be an analyte component responsive dye for the preferred colorimetric version of the sensor, or a reactor which fluoresces under light stimulation. The outward surface 506 of membrane 496 is immersed in blood or flowing blood of a bloodstream as represented in general at 508 and containing analyte component elected for sensing as represented at 510. For the preferred embodiment of the invention, wherein ammonia ($NH_3$) is the analyte component and an analyte component-sensitive dye is employed for reactor 504, the membrane 496 is configured having microscopic pores through which the ammonia may migrate and chemically react with the dye-defined reactor 504. This will result in a change in coloration of the dye-defined reactor 504 which may be analyzed by colorimetric procedures. Accordingly, the reactor 504 is stimulated by light at one or more wavelengths as represented by the light wave transmission arrow 512. The resultant light reflected from the reactor dye is represented at reflection arrow 514. As before, it is preferred that the forward assembly of the sensor be located to confront the direction of flow of the bloodstream as represented by arrow 516.

Figure 19:
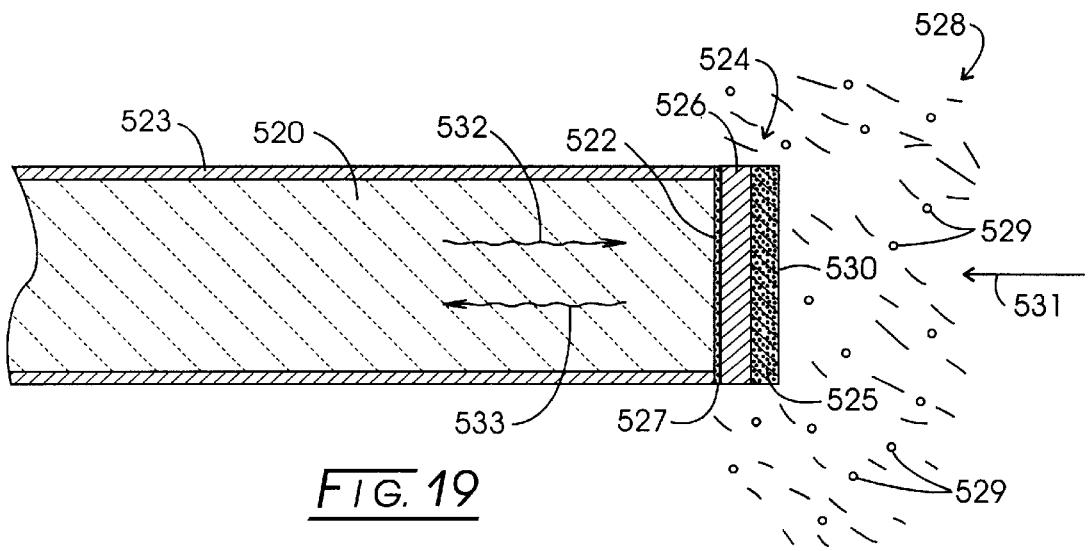
FIG. 19 is a schematic representation of a front end assembly of a concentration sensor which may be employed with the invention.

Referring to FIG. 19, a preferred arrangement for a sensor forward assembly, particularly with respect to the sensing of the analyte component ammonia ($NH_3$) is revealed. The sensor arrangement includes a fiberoptic assembly 520 which is implemented as a single fiberoptic strand. Assembly 520 extends from a proximal region (not shown) from which sensor outputs are transmissible to a tip surface or distal end face 522 and its outer surface is covered with an optical fiber cladding 523. Cladding or sheath 523 may be, for example, fluoroacrylate having a thickness selected from within a range of about 5 to 20 microns. The reactor and support components are shown generally at 524 and, preferably, are formed as a subassembly. That subassembly includes a porous polymer reactor support 525. Support 525 may, for example, be formed of polytetrafluoroethylene configured with a matrix of pores having, for example, a size of 0.2 microns. The support 525 thickness is selected within a range of about one to four mils. An analyte sensitive dye is immobilized within the porous membrane or matrix 525. That dye may, for example be bromocreosol green. Bonded to the inward face of the support 525 is a non-porous optically transparent polymer 526. Bonding between the polymer support 525 and the non-porous layer 526 is carried out with heat and pressure. Accordingly, there is no adhesive invasion of the matrix of pores within the support 525. The layer or backing component 526 may be formed of polyetheylene having a thickness, for example, of about 1 to 4 mils. That backing component 526 then is adhesively attached to the face 522 of fiberoptic assembly 520 with an optically transparent adhesive layer 527. Adhesive layer 527 may, for example, be provided as cyanoacrylate or may be provided as a pressure sensitive or pressure activated adhesive. Generally the adhesive layer 527 will have a thickness of from about 0.2 to 1 mil. The fiberoptic assembly 520 typically will be provided with a diameter of between about 100 to 200 microns. In general, membrane 525 will incorporate a dye which changes color with respect to the concentration of ammonia within a bloodstream represented generally at 528. Reactor support 525 may also be provided, for example, as a silicone perthiorinated urethane, cellulose acetate, butyrate, or methymethacrylate polymer matrix incorporating a dye. The outward surface 530 of support 525 is shown within the bloodstream 528 in an orientation wherein it confronts the flow of blood, here represented at arrow 531 The analyte component or ammonia affected reactor dye incorporated within the support 525 will respond to the migration of that component thereinto to evoke the noted change in coloration and that coloration change may be analyzed, inter alia, by colorimetric procedures. Accordingly, the dye-containing pore matrix support 525 is seen to be interrogated at light at one or more wavelengths as represented by lightwave transmission arrow 532. The resultant light reflected from the reactor dye as integrated within the pore matrix support 525 is represented at reflection arrow 533.

A system utilizing ammonia as the analyte component measured and ammonia sensitive dye as a reactor which is incorporated within a membrane, is a preferred embodiment of the invention. Of the ammonia dyes available for use as such reactor, bromocreosol green, excited at wavelengths in a first band of 380 to 480 nm; in a second band of 520 to 680 nm; and in a third band of 700 to 900 nm; chlorophenol red excited at wavelengths in a first band of 380 to 420 nm; in a second band of 520 to 620 nm; and in a third band of 650 to 900 nm; bromophenol blue excited at wavelengths in a first band of 380 to 440 nm; in a second band of 520 to 640 nm; and in a third band of 700 to 900 nm; m-creosol purple; thymol blue; and congo red may also be considered. The light wavelengths for stimulation or interrogation conventionally are generated by light emitting diodes (LEDs) and the wavelengths utilized are based upon the wavelengths corresponding to the peak absorption intensity and wavelengths which are insensitive to changes in, for example, the ammonia concentration. If a plastic fiberoptic assembly is used, the preferred third wavelength is about 700 nm. If a glass fiberoptic light transmitting assembly is used, the preferred third wavelength of those recited above is within the range specified. Dyes serving as reactors quite rapidly reach an equilibrium with the analyte component under analysis. The intensity normalized reflectance of the responding wavelengths of light, for example, that at 533, is utilized to quantitate the concentration of analyte component (e.g., ammonia). Where the sensor assembly reactor is provided as an analyte-sensitive fluorescent material, then upon excitation by light wavelengths, the level or intensity of fluorescence or the rate of quenching when a stimulation source is extinguished is correlated with the concentration of analyte component.

Where the analyte component is ammonia, as is preferred, in order to derive the value of total ammoniacal concentration, the value of the corresponding pH of the blood is utilized in a straightforward computation to find total ammoniacal concentration. h general, the Henderson-Hasselbalch relationship is resorted to. The pH may be measured with a variety of techniques using reactors which are chemical or ion selective electrode-based. A pH sensitive dye is employed in connection with the embodiment described in conjunction with FIGS. 4–6. Looking to FIG. 20, a sensor front end assembly is revealed in schematic fashion. In the figure, a fiberoptic assembly embodied as a fiberoptic strand is illustrated. The outer cylindrical surface 552 of assembly 550 is covered with a sheath 554 and the tip surface or face 556 of the fiberoptic assembly 550 is coated with a pH sensitive dye which is applied as a porous coating and is represented at 558. Sealingly positioned over the tip surface or face 556 and the dye or pH reactor 558 is a hydrogen ion permeable membrane represented generally at 560 which is cap-shaped having a cylindrical side component 562 sealed to the sheath 552. The inner forward surface 564 of membrane 560 is spaced from the dye layer or pH reactor 558 to accommodate a medium 566 whose pH is at equilibrium with the pH of the blood within which this sensor forward assembly is immersed. The pH sensitive dye or the like is interrogated by light at one or more wavelengths to determine the value of pH of the blood. The sensor forwarded assembly of FIG. 20 may, for example, be incorporated in the catheter structure described in connection with FIGS. 10–12. It also may perform at other locations, for example, adjacent an injectate port as described in those figures. Additionally, for sensor support structures of minimal size as described later herein, the forward assembly of FIG. 20 may be incorporated within a separate catheter or separate support structure.

Optical sensors for the measurement of pH, particularly in connection with the in vivo measurement of pH of the blood are described, for example, in U.S. Patent No. 5,607,644 by Olstein, et al., entitled "Optical Sensor for the Measurement of pH in a Fluid, and Related Sensing Compositions and Methods", issued Mar. 4, 1997. Additionally, description of such pH sensors is provided in the following publication:

Zhang, et al., "Evaluation of Fluorescent Dyes for in vivo pH Measurement", *Medical & Biological Engineering & Computing*, March, 1994, pp 224–227.

These references describe, in particular, fluorescing analysis techniques.

Referring to FIGS. 21 and 22, the light source and transducing function (LS+T) described at block 294 in FIG. 5, representing a component of the signal treatment system of the invention is revealed in more detail. This light source and transducing function also may be utilized for the function of that figure represented at block 300 employed for carrying out pH analysis. This particular assembly is utilized with the colorimetric sensor embodiment (FIGS. 18 and 19) wherein the reactor is an analyte component-sensitive dye, preferably sensitive to ammonia ($NH_3$). In FIG. 21, a fiberoptic transmission assembly as described in FIG. 10 at 122 and 124 is seen to provide a fiberoptic input 570 to a step-down chamber 572. Through the utilization of this chamber 572, a singular fiberoptic strand or assembly 570 is positioned in light exchange relationship with an assemblage of seven fiberoptic components or channels represented generally at 574. The discrete fiberoptic components of the assemblage 574 include: a fiberoptic component 576 which transmits light at a wavelength, for example, of 450 nm from an LED source 578; a transmitting fiberoptic component or strand 580 which transmits light at a wavelength, for example, of 615 nm from an LED source 582; and a fiberoptic strand or component 584 which carries light, for example, at a wavelength of 700 nm from an LED source 586. Reference fiberoptic components 588, 590 and 592 transmit light from respective sources 578, 582 and 586 to a photodiode reference function represented at block 594. Light returning from impingement upon the analyte component sensitive dyes is collected or gathered and transmitted by core gathering fiberoptic components 596–599. Optical components 596–599 are directed to a combining input at a photodiode sensor represented at block 600.

Looking to FIG. 22, a cross-section of the assemblage 574 is provided. The gathering component 596 is seen to be centrally disposed within the assemblage 574, while remaining gathering components 597–599 are disposed symmetrically about it. Transmitting fiberoptic components 576, 580 and 584 have the same diameters and are seen to be symmetrically disposed about the centrally located collecting component 596. With this arrangement, about 11% of the source light from each of the sources 578, 582 and 586 is transmitted to the associated reactor and about 44% of the light reflected from the reactor is transmitted to the photo diode detector 600.

Figure 23:
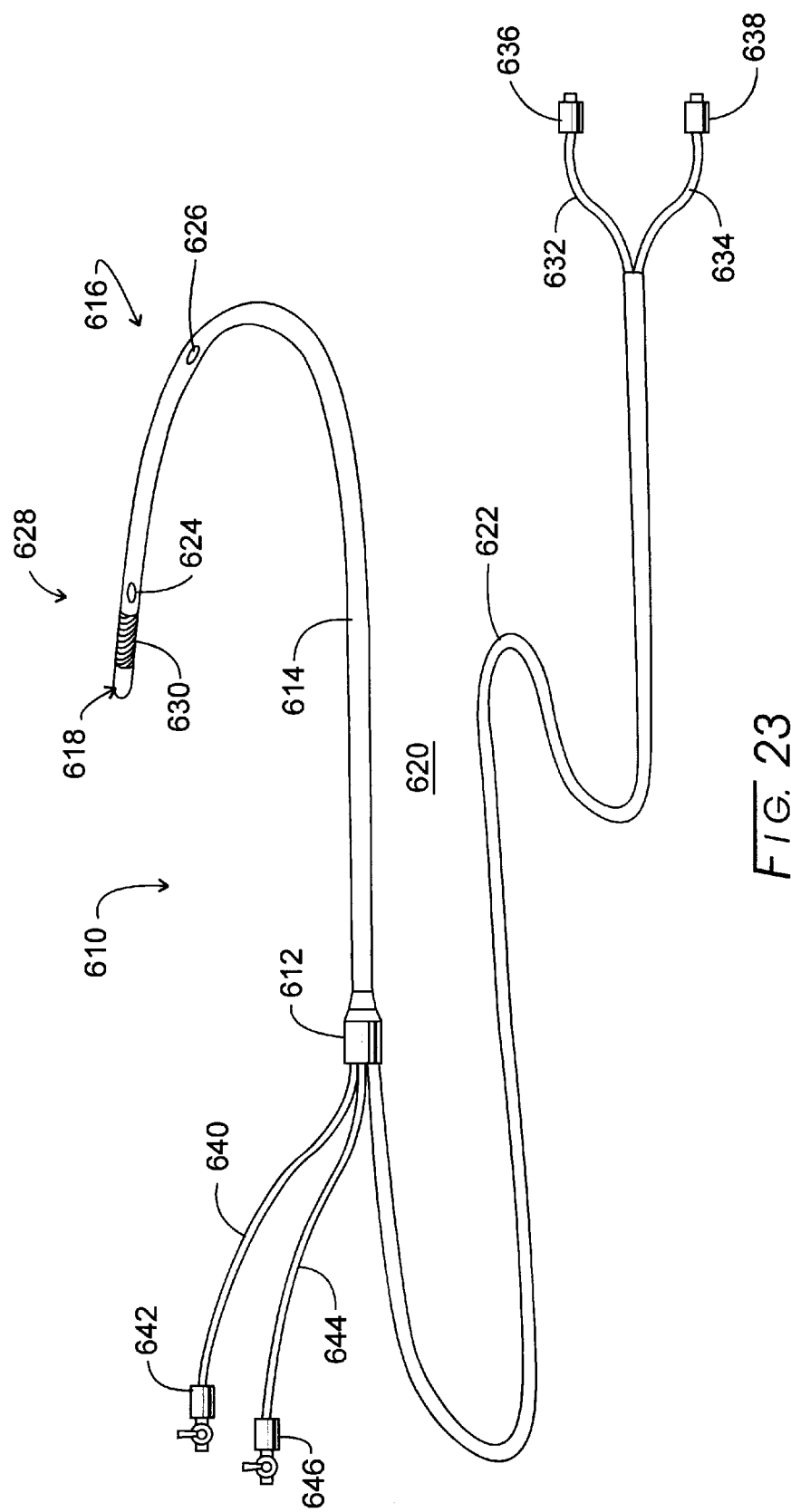
FIG. 23 is a pictorial view of a catheter incorporating a concentration sensor with non-optical technology.

Analyte concentration and sensing systems may be configured using technologies other than those which are optically based. Where such alternate approaches are utilized, some modification of the design of a catheter-based embodiment is undertaken. Referring to FIG. 23, a catheter is shown at 610 being structured with an analyte concentration sensor which is non-optical in design. Catheter 610 may employ a variety of sensor technologies, for example, sensors based on amperometry and voltometry, as well as Schottky diode-based technologies and acoustic-wave based technologies. Catheter 610 includes a base component 612 from which extends a catheter body 614 configured for positioning within a vessel of a vascular system at a peripheral region of the body. Body 614 incorporates a measurement region 616 which extends to a tip 618. Base 612 is located within a proximal region represented generally at 620 which includes a communication cable 622. Spaced rearwardly from the tip 618 is a distal auxiliary port 624 and, still further rearwardly positioned, is a second or proximal auxiliary port 626. Ports 624 and 626 are optional within the catheter 610 and may be employed for deriving, for example, blood samples, introducing medicants or the like. The forward assembly of the analyte sensor is represented generally at 628 within measurement region 616. Preferably, assemblage 628 is located adjacent tip 618. For most implementations of this form of forward assembly 628, a membrane of the nature discussed above is employed. Catheter 610 is dimensioned having a principal cross sectional dimension or outer diameter which is as minimal as practical to avoid blood hydraulic impedance phenomena. A membrane 630 covers a sensor assembly adjacent the tip 618. This sensor assembly is electrically associated with the proximal regional 620 via cable 622 and is seen to extend to electrical leads 632 and 634 terminating, in turn, at respective electrical connectors 636 and 638. Communication with auxiliary port 624 is provided by a channel extending through the body portion 614 to base 612. From that location a flexible conduit 640 is seen to extend to a connector and valve assembly 642. In similar fashion, the proximal port 626 is in fluid communication with a channel extending through the body portion 614 to base 612. At base 612 this channel is coupled in fluid transfer communication with a flexible conduit 644 extending to a connector and valve assembly 646.

Referring to FIGS. 24 and 25, the structure of catheter 610 at its forward assembly 628 is revealed. At forward assembly 628 the polymeric body portion 614 is configured of reduced diameter to accommodate for the sensor structure associated with membrane 630. FIG. 25 reveals this reduced cylindrical outer diametric surface 650 which additionally is configured to form three channels or lumens 652–654. Channel 653 is revealed in FIG. 25. Channels 652 and 653 communicate with respective auxiliary ports 624 and 626 (FIG. 23). These channels are plugged with a cylindrically-shaped tip plug 656 forming the outer tip 618 of catheter 610. The analyte concentration sensor is represented generally at 660 and, being formed in conjunction with membrane 630, is structured as an ion-specific electrode-based device. Membrane 630 is provided as a microporous, hydrophobic polymer such as the earlier-described Teflon or polytetrafluoroethylene. Membrane 630 is semi-permeable to the ion of interest. For 15 example, where the analyte containing fluid is an ammoniacal fluid, the ion of interest is the ammonium ion ($NH_4^+$). FIG. 25 reveals that the cylindrical body surface 650 at the sensor 660 forms the inner wall of an electrolyte retaining chamber or gap 662, the outer wall of that gap or chamber being the membrane 630. Within the gap 662 is an electrolyte or electrically conducting liquid 664. Where the sensor 660 is configured for detecting the noted ammonium ion analyte component, the electrolyte liquid 664 may be a solution containing, for example, 0.1 molar ammonium chloride. That liquid 664 reaches equilibrium with blood-carried ammonium ion flow across membrane 630 to change or alter the pH of the solution or liquid 664. For the ammonium ion component, the higher the concentration of ammonium ion in the bloodstream passing over the membrane 630, a corresponding effect will be observed in the ammonium ion concentration in liquid 664. Ion selective electrodes are employed to measure this ion concentration within liquid 664. In this regard, the cylindrical surface 650 is coated at the forward assembly 628 with a pH electrode which may be implemented as a glass electrode selective to the hydrogen ion. Such an electrode is shown at 666. Electrode 666 may be a glass comprising silicon dioxide, lithium oxide and calcium oxide in the ratio 68:25.7. Note in FIG. 24, that electrode 666 extends from an annular shoulder 668 formed in body portion 614 adjacent tip 618 to an edge or termination at 670 and is connected to an electrical lead 672 extending within channel 654. A cylindrically shaped reference electrode 674 completes the forward assembly 628. This second electrode 674 may be provided as a metallic coating, for example, silver/silver chloride. Electrode 674 is spaced from the glass electrode 666 but remains operationally associated therewith within the electrolyte containing cavity or gap 662. Electrode 674 is connected to an electrical lead 676 which also extends through the channel 654. Sensor 660 may perform either in a potentiometric mode wherein voltage across the reference and glass electrode is determined, or may operate in an amperometric mode wherein the current flow between these two electrodes is evaluated during the application of a d.c. voltage difference.

Referring to FIGS. 26 and 27, sections of the catheter 610 adjacent the proximal auxiliary port 626 are revealed. In the figure, catheter body portion 614 is seen to have an enlarged diameter as compared with its diametric extent at the sensor 660. FIG. 26 reveals auxiliary channel or lumen 653 as it extends to the port 626. In this regard, while the channel 653 extends essentially the length of the catheter 610, fluid is restricted to fluid outflow from the port 626 by a plug 680 just forward of the proximal port. FIG. 27 reveals the electrical leads 672 and 676 extending within the electrical lead channel 654.

These leads become a component of the cable 622 at base 612 and further evolve as the leads 632 and 634 leading to respective connectors 636 and 638 (FIG. 23).

Figure 28:
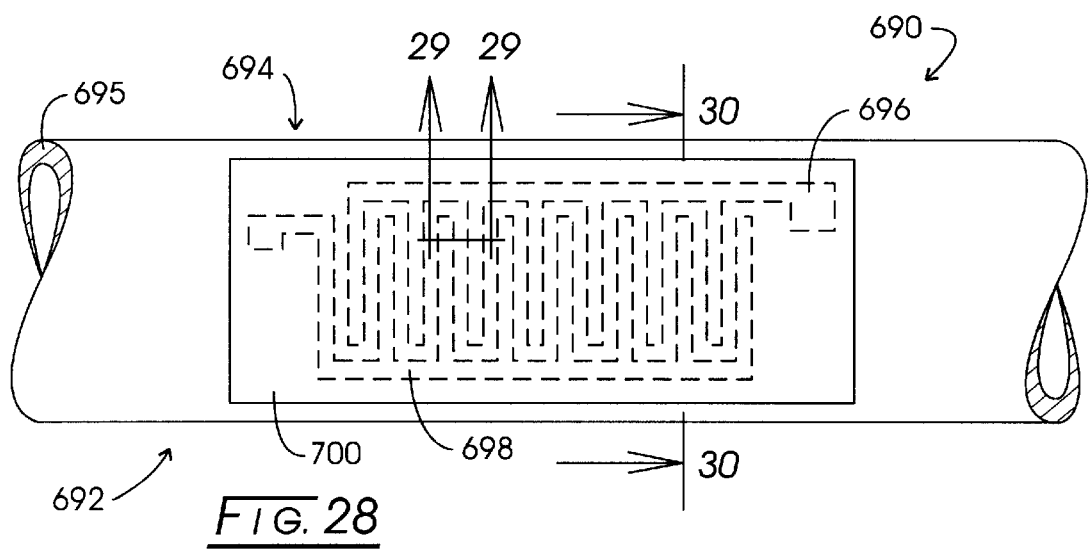
FIG. 28 is a schematic diagram of a Schottky diode-based ammoniacal component concentration sensor.
Figure 29:
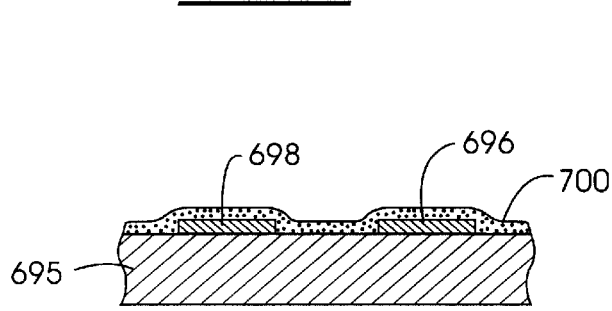
FIG. 29 is a sectional view taken through the plane 29—29 in FIG. 28.
Figure 30:
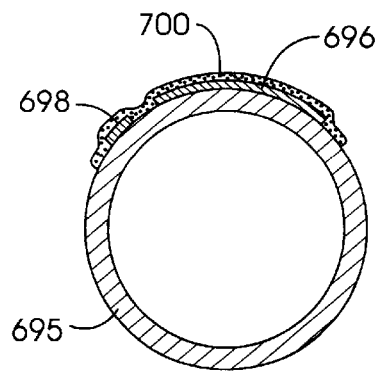
FIG. 30 is a is a sectional view taken through the plane 30—30 in FIG. 28.

Now looking to the utilization of Schottky diode-based analyte sensor assemblies, reference is made to FIGS. 28–30. In the figures, the sensor assembly is represented in schematic fashion. Looking to FIG. 28, the measurement region 690 of a catheter 692 of a variety described in connection with FIG. 23 is seen to incorporate a front end assembly 694 which employs the technology based upon the interaction of planner Schottky barrier diodes with an analyte component. In this embodiment, the sensor or front end assembly 694 is mounted upon, for example, a wall 695. Sensor 694 is formed having two metal electrodes configured in spaced relationship and in an interdigitated geometry. These electrodes are provided as a gold electrode 696 configured in conjunction with an aluminum electrode 698. Gold electrode 696 creates an ohmic contact and aluminum electrode 698 creates a Schottky barrier contact with a conducting polymer layer 700. For example, a p-doped semi-conductor such as P3TO may be employed (poly (3-Octylthiophene)). The conducting polymer 700 exhibits an electrical conductivity which is correlatable with the concentration of the analyte component at hand. Conducting polymers which may be employed with the sensor at hand may be substituted polypyrroles, polythiothenes, or polyanillianes. Not shown in the drawings is an analyte component permeable membrane as discussed earlier herein which covers the active sensor components. As before, the outer surface of such membrane is in contact with flowing blood of the bloodstream. See generally:

Assadi, A., et al., "Interaction of Planner Polymer Schottky Barrier Diodes with Gaseous Substances", *Sensors and Actuators*, Vol.

20, pp 71–77 (1994).

Figure 31:
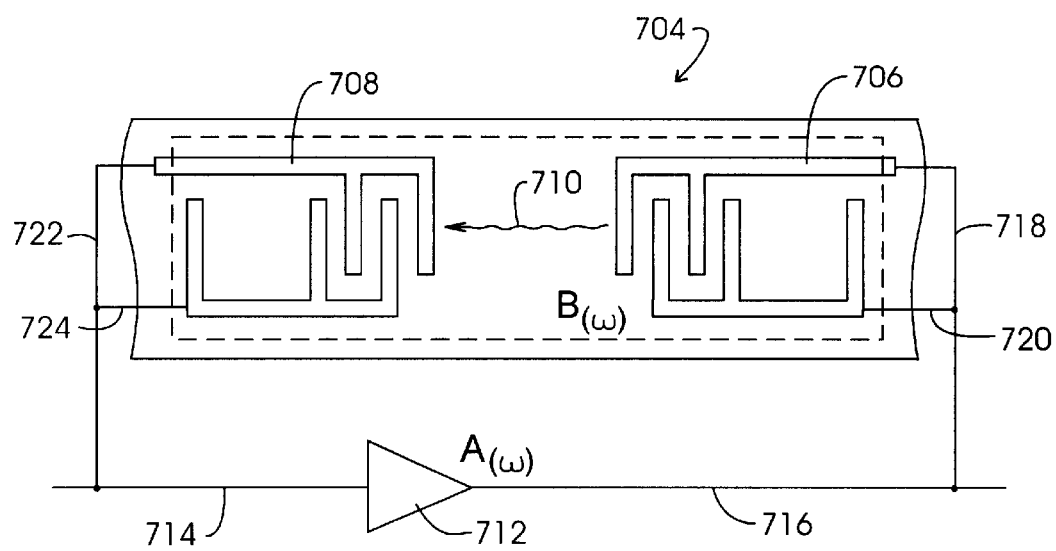
FIG. 31 is a schematic representation of an acoustic wave-based ammoniacal concentration sensor.

Now considering analyte component sensors which are acoustic wave-based, reference is made to FIG. 31. In the figure, the sensor forward assembly as it would be mounted in the manner of the sensor of FIGS. 28–30 is depicted schematically at 704. The sensing principle of such acoustic sensors is based upon the detection of changes of a wave velocity and attenuation caused by perturbations at the surface of the material in which the wave propagates. If an acoustic wave delay line is placed in a oscillator loop as the frequency-determining elements, velocity shift causes a shift of the delay time of the wave. This results in a shift of the oscillation frequency. In the figure, an intricate digitated transmission transducer is shown at 706 spaced from a reception transducer 708. Sound reflectance from the analyte component being investigated is represented by the arrow 710. Transducers 706 and 708 are connected in a delay line oscillator circuit. The latter circuit includes an oscillator amplifier 712 having an input at line 714 and an output at line 716. Transducers 706 and 708 are incorporated within a feedback path or delay line, transducer 706 being coupled via lines 718 and 720 to line 716 and transducer 708 being coupled via lines 722 and 724 to line 714. Accordingly, the output of the amplifier 712 is fed back by the delay line incorporating the transducers where $A_{(\omega)}$ represents amplifier gain and $B_{(107)}$ represents delay line losses. The transducers, as well as the oscillator circuit may be multi-layered devices constructed using conventional integrated circuit manufacturing methods employing silicon (base), silicon dioxide, aluminum, and zinc oxide (surface). See generally the following publication:

Vellekoop, et al.,"Integrated-Circuit-Compatible Design and Technology of Acoustic-Wave-Based Microsensors", Sensors and Actuators, Vol. 44, pp 249–263 (1994).

Other analyte or analyte component sensors may be provided as follows:

A glucose sensor may be constructed using well-known enzyme-based methods (e,g., involving glucose oxidase in conjunction with an oxygen sensor). In such a devices, an immobilized biological/biochemical component interacts with the analyte to produce, via an appropriate transducer, a signal proportional to the quantity or activity of analyte. The recognition interaction may entail either a binding process (e.g. for antibodies) or a biochemical reaction (e.g. enzyme catalysis). Transduction can be achieved by any of several detection approaches: optical (e.g. absorbance, fluorescence, chemiluminescence and bioluminescence), mass measurement (e.g. piezoelectric and surface acoustic wave), heat and electromechanical-based measurement. By way of example, the sensor may be constructed based on the principles first described by Clark and Lyons (Clark, L. C. and Lyons, C., "Electrode System for Continuous Monitoring in Cardiovascular Surgery," Ann. N.Y. Acad. Science, Vol. 102, p. 29ff [1962]). The concentration of glucose in the blood is achieved by means of a dissolved oxygen ($PO_2$) sensor used in conjunction with the glucose oxidase-catalyzed reaction.

Figure 32:
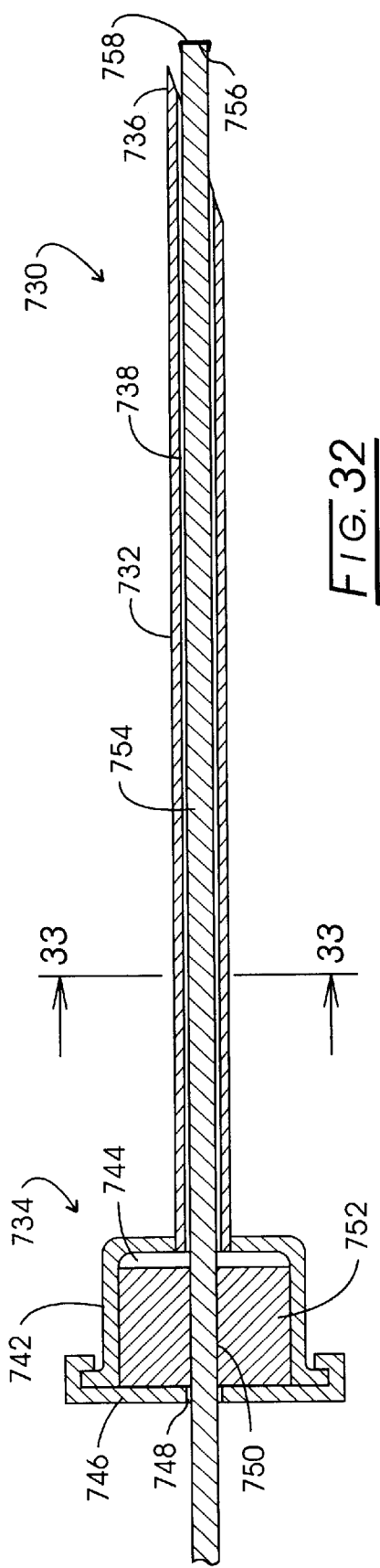
FIG. 32 is a sectional view of a catheter of minimal dimension employed with the system and method of the invention.
Figure 33:
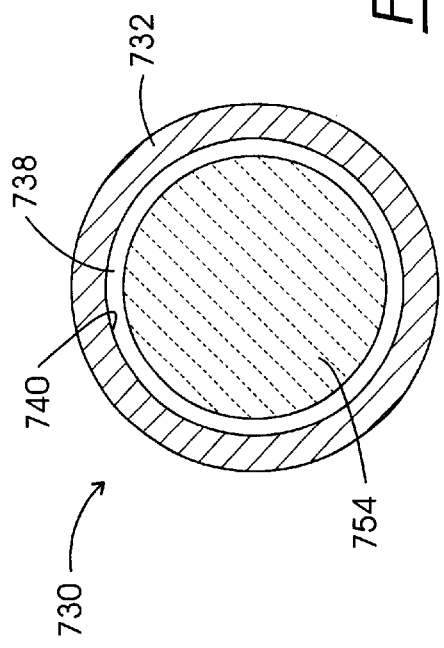
FIG. 33 is a sectional view taken through the plane 33—33 shown in FIG. 32.

In the practice of accessing the vessels of the vascular system to carry out analyte component monitoring according to the invention, a variety of vessel sizes and vessel conditions will be encountered by the practitioner. In this regard, a catheter of conventional diametric extent may evoke a hydraulic impedance in the vessel carrying blood to the extent that the vascular system may divert the blood flow or bloodstream to a branch vessel. Further in this regard, particularly where infants such as neonates are the subject of analyte component measurement, the vessels themselves may be so small as to call for a catheter which, in effect is simply a sensor support exhibiting a very minimal principal cross-sectional dimension. For example such dimension may represent a diameter in a range of about 0.010 inch to 0.060 inch. In this regard, such a catheter can be developed which is quite similar to a hypodermic needle wherein the central channel supports a singular fiberoptic strand to carry out monitoring. Where the analyte component of interest is gaseous ammonia, two such catheters may be employed, one to measure pH and the other to measure the component ammonia gas. The forward end assemblies of such optical sensor devices are structured in the manner described above, for example, in connection FIGS. 19 and 20. Looking to FIGS. 32 and 33, a catheter configured as a thin sensor support structure of requisite minimized shaft diameter is revealed generally at 730. Catheter 730 includes a rigid shaft 732 extending from a base shown generally at 734 to a pointed tip 736. Configured in similar fashion as a hypodermic needle, the shaft 732 incorporates a cylindrical channel 738 as defined by its inner, curved surface 740 (FIG. 33). Base 734 includes a cap-shaped cylindrical hub 742, the internal cavity 744 of which is enclosed by a cover member 746. Member 746 includes a circular opening 748 which is aligned with a centrally disposed channel 750 within a sealing gland or seal 752. Seal 752 may be formed of silicone rubber. Extending through this support assembly is a fiberoptic strand 754, the forward tip 756 of which is covered with a membrane-based reactor structure 758 which is configured, for example, as described in connection with the above-noted FIGS. 19 and 20. Catheter configurations as at 730 may have overall lengths within a range of about 1.0 inch to about 6.0 inch and perform with fiberoptic strands of diameter within a range of about 0.005 inch to 0.040 inch.

Figure 34:
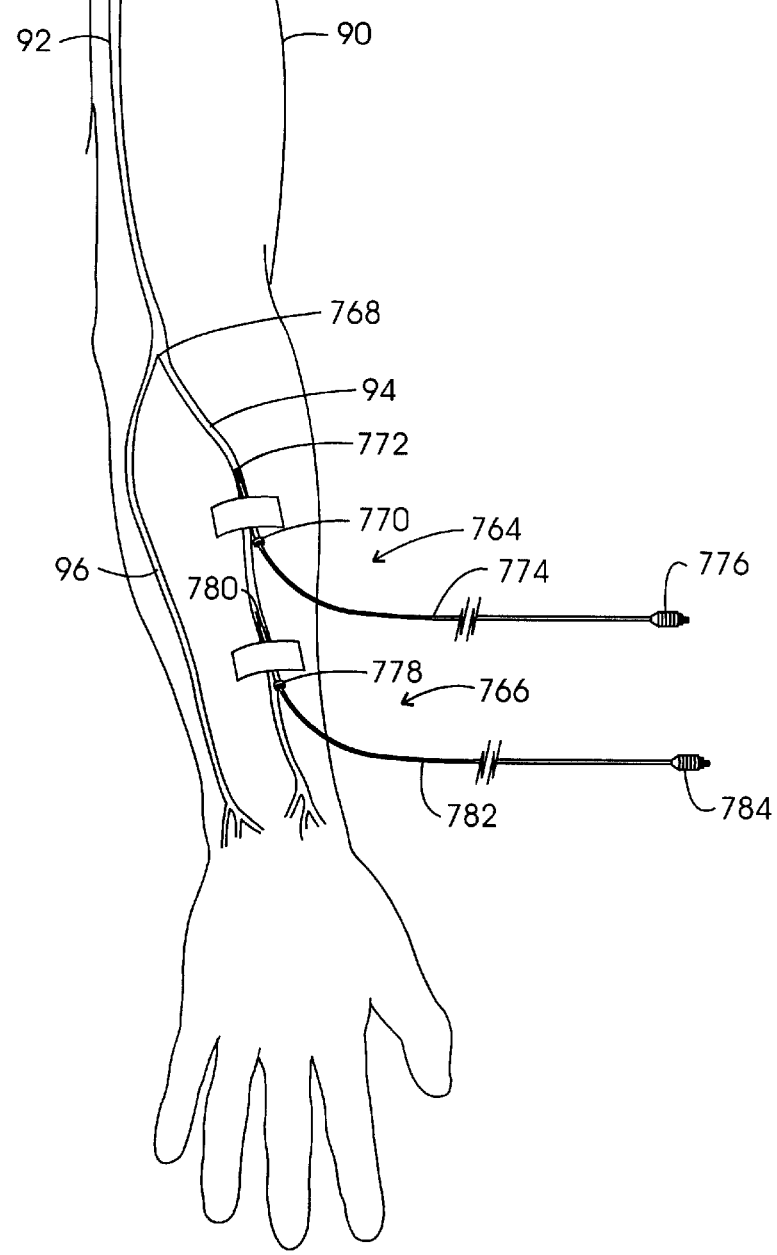
FIG. 34 is a pictorial representation of a human arm with the insertion of a pair of catheters of minimal dimension according to the invention.

Animal testing carried out in conjunction with fiberoptic-based catheters according to the invention have shown that improved sensor response is achieved where the catheter is inserted within a vessel of the vascular system in a manner wherein the sensing tip employed with the sensors is in a confrontational orientation with respect to the direction of blood flow. Where the sensing tip of such sensor structures is located within a blood carrying vessel in a manner wherein blood passes over it from what may be considered a rearward location, the surface of such a sensor may encounter a more or less quiescent or back flowing blood. This has a tendency to extend the response time or sensitivity of the sensors. Confronting orientations for the sensors are represented in FIGS. 3 and 34. Referring to the latter figure, arm 90 is reproduced from FIG. 3 along with the earlier noted arteries which are identified with the same numeration as utilized in FIG. 3. The figure illustrates the utilization of catheters or sensor support assemblies as described at 730 in connection with FIGS. 32 and 33. Two of these diminutive sensor assemblies are represented in FIG. 34, one shown generally at 764 having been inserted within radial artery 94 and another downstream therefrom shown generally at 786. The diminutive size of these sensors minimizes the amount of hydraulic disturbance within the bloodstream to avoid diversion of bloodstream flow at the arterial branch 768 from the radial artery 94 into the ulnar artery 96. Sensor 764 functions to measure an analyte component such as ammonia gas, the hub and cover member assembly being seen at 770 and the reactor structure at 772. The fiberglass strand positional within the central channel of the hub and cover member 770 and the shaft is shown at 774 extending to an optical coupler 776. Coupler 776 is configured for connection into the optical receiving components of a controller. In similar fashion, the sensor assembly 766 is shown incorporating a hub and cover member assembly 778 and the tip of the inserted catheter assembly extends to a reactor structure 780. The fiberoptic strand which extends through the support assembly to that structure 780 is represented at 782 extending to an optical coupler 784.

The positioning of sensor assemblies 764 and 766 so as to monitor the blood flow within the radial artery 94 involves the removal of a co-extruded polymeric reinforcement covering from the fiberoptic strands as at 774 and 782 a distance of about three inches from the reactor contained tip and the insertion thereof within the shaft of the support assembly or catheter. Upon insertion of the catheter within the radial artery 94, this sensor assembly then is pushed forwardly to expose the reactors as at 772 and 780 to confront the bloodstream flow. Measurement procedures then ensue.

Figure 35:
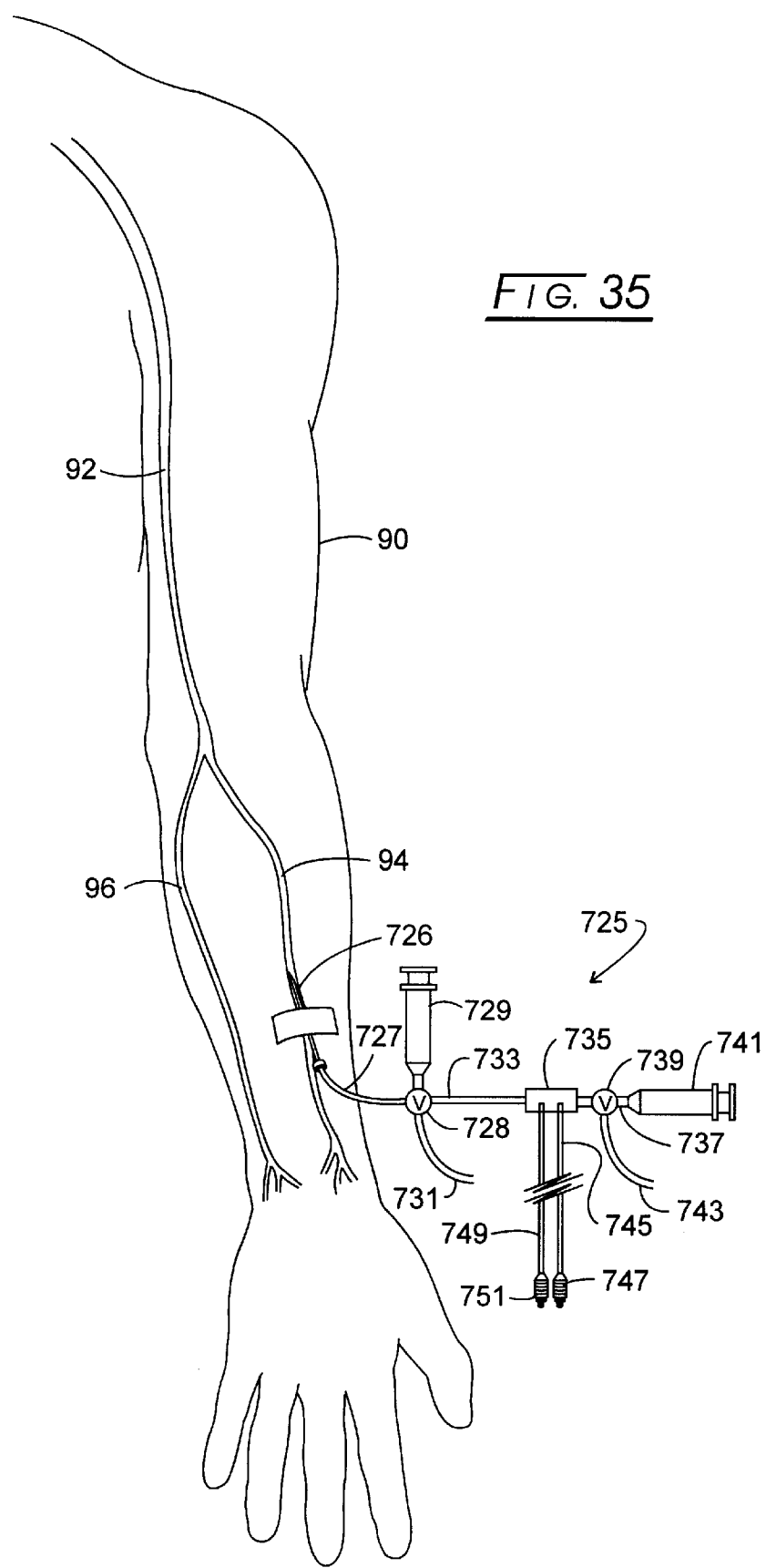
FIGS. 35 is a pictorial representation of a human arm with a bypass sampling arrangement for carrying out the measurement procedures of the invention.

The measurement of CO and TCBV according to the invention may be employed with analyte concentration sensor assemblies which are not invasive into the bloodstream in the sense that a catheter or similar assembly is not utilized. For example, the sensing approach may be carried out with a variety of blood bypassing systems or assemblies such as a hand actuated blood dose collecting system; a cardiac bypass system; or a hemodialysis system. Referring to FIG. 35, the former approach is illustrated. In the figure, the arm 90 again is reproduced along with arterial vessels 92, 94 and 96. Delivery of the analyte into the bloodstream is in the manner as above described. In the instant embodiment, the blood bypass assembly is represented in general at 725. Assembly 725 includes a hypodermic needle or the like, 726 which has been positioned such that its tip extends within the radial artery 94. A conduit 727 extends to a valve represented at symbol 728 which is coupled to a hypodermic syringe 729 utilized for flushing purposes in conjunction with a flushing fluid input at conduit 731. Valve 728 additionally is coupled to conduit 733 which extends to a sampling chamber 735. From the chamber 735, a conduit 737 incorporating a valve 739 extends to a sampling syringe or pump 741. A flushing drain conduit 743 is coupled to valve 739. Sampling chamber 735 is accessed, for the instant embodiment, by a fiberoptic based pH sensor having an output cable 745 extending to an optical connector 747. Also communicating with the sampling chamber 735 is a fiberoptic based ammonia sensor having an output cable 749 extending to an optical connector 751

For the arrangement at hand, following the infusion of analyte fluid within the bloodstream, the syringe 741 is actuated by the practitioner to draw a sample of blood into sampling chamber 735. As the blood enters chamber 735, it is sensed for ammonia concentration and pH level and the resultant values are submitted to a controller (not shown) via connectors 747 and 751. Following submittal of data to the controller, the syringe 741, again may be actuated to return the sample of blood to the radial artery 94 via the hypodermic needle 726. It may be desirable from time to time to flush such bypass systems. For such an arrangement, the syringe 729 withdraws a quantity of flushing liquid of conduit 731 with appropriate manipulation of valve 728 to cutoff fluid communication with conduit 727. The syringe 729 then is actuated to pump the flushing liquid through conduit 733 and the sampling chamber 735. Valve 739 is manipulated such that the flushing liquid will drain through conduit 743 and the input to pumping syringe 741 is blocked.

To develop a concentration curve, a relatively small volume of blood is withdrawn over an interval. As an example, about two milliliters of blood may be introduced into chamber 735 over about a 120 second interval. It may be desirable from time to time to flush such bypass systems. For such an arrangement, the syringe 729 withdraws a quantity of flushing liquid from conduit 731 with appropriate manipulation of valve 728 to cut off fluid communication with conduit 727. The syringe 729 then is actuated to pump the flushing liquid through conduit 733 and the sampling chamber 735. Valve 739 is manipulated such that the flushing liquid will drain through conduit 743 and the input to pumping syringe 741 is blocked. Bypass measurement may be under the control of a controller and associated control modalities, as opposed to the hand actuated arrangement shown. A baseline measurement is carried out prior to each delivery or infusion to provide for hemodynamic parameter computation. Particularly where ammoniacal fluid is infused, these baseline values may be used to monitor total ammoniacal concentration (TAC).

Figure 36:
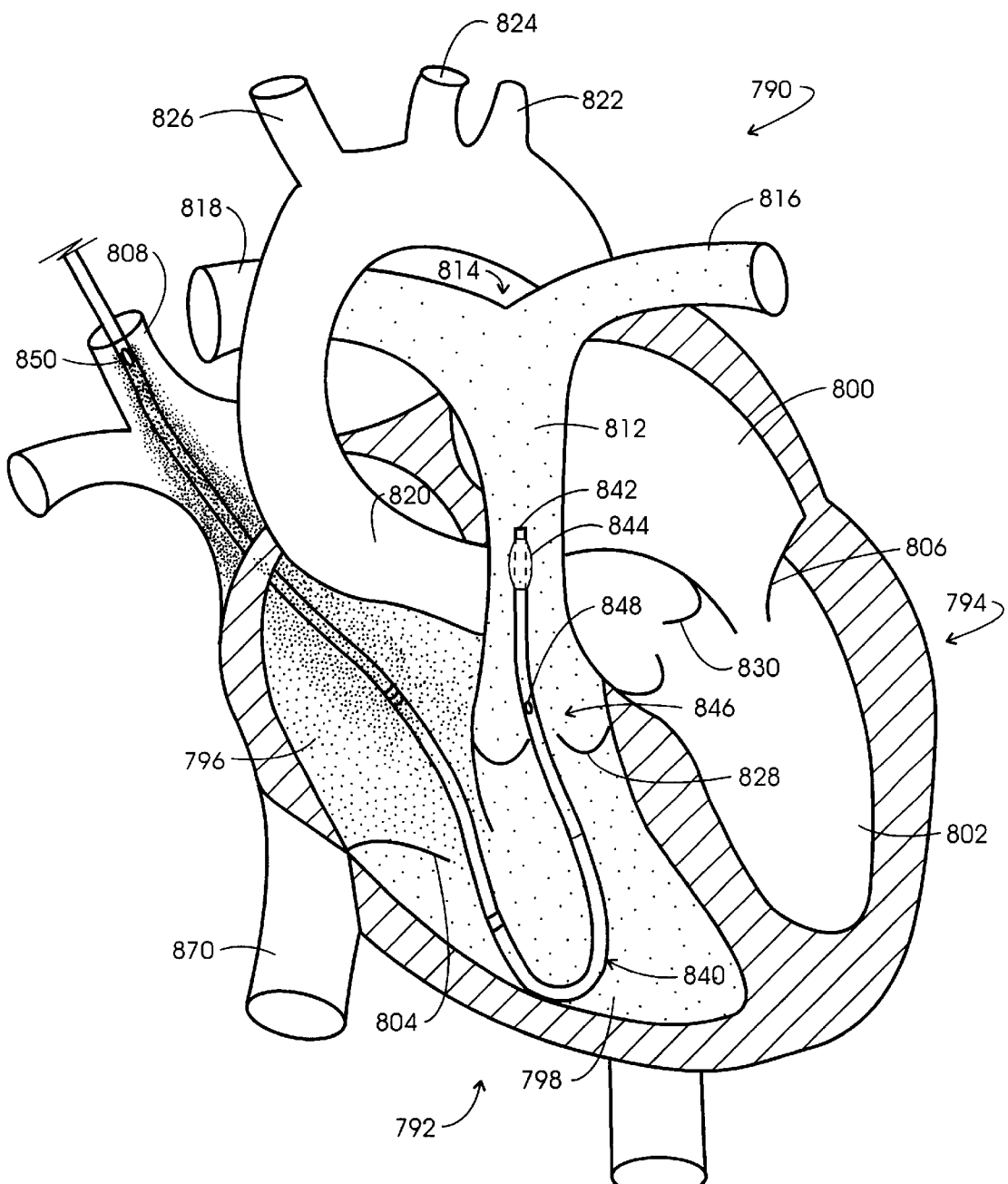
FIG. 36 is a schematic, partially sectional view of a heart showing the placement and use of a pulmonary catheter structured to incorporate the system of the invention.

While the substantial utilization of the instant system is one wherein the analyte concentration sensors and delivery assemblies are positioned within peripheral regions of the vascular system, it also has application to invasive catheter structures configured for indwelling within the heart. In particular, those structures can be configured to measure both cardiac output and total circulating blood volume. Looking to FIG. 36, a schematic representation of a human heart 790 is provided. In general the heart 790 has a right side which receives venous-based blood returning from various tissues and vessels of the body. This right side of the heart is generally represented at 792. The blood is returned from the lungs and pumped arterially against the vascular resistance of the entire body by the left side of the heart generally represented at 794. The pumping chambers of the heart are represented in FIG. 36 as a right atrium 796 and a right ventricle 798. Correspondingly, the left atrium is shown at 800 and the left ventricle at 802. The right atrioventricular valve is schematically portrayed at 804, and the left atrioventricular (mitral) valve is represented at 806. Looking to the input to the right side 792 of the heart 790, the superior vena cava is represented at 808, while the inferior vena cava is represented at 810. The output of the right ventricle 798 is shown extending to the pulmonary artery 812 which, in turn, extends to a bifurcation represented generally at 814 to define a left pulmonary artery 816 and a right pulmonary artery 818. Left ventricle 802 is seen extending to the aorta 820 having an aortic arch from which the left subclavian artery extends as shown at 822, the common carotid artery extends as shown at 824, and the brachiocephalic trunk extends as shown at 826. The pulmonary valve is seen at 828, while the aortic valve is represented at 830. As noted earlier herein, essentially all blood within the circulating blood volume passes through the right ventricle to the pulmonary artery 812. Accordingly, not only cardiac output (CO) but also total circulating blood volume (TCBV) can be measured at this location. As noted earlier, however, a reasonably thorough mixing of the analyte within the blood is required to achieve an accurate measurement of TCBV.

A pulmonary artery catheter adopted to carry out the system and method of the invention is represented generally at 840 at the indwelling location normally encountered for heart monitoring. For the present application the catheter 840 is adapted to carry out CO and TCBV measurement. The location of the catheter 840 within the heart 790 is similar to that of the positioning of a conventional Swan-Ganz flow directed thermodilution catheter. See in this regard:

Daily, E., "Techniques in Bedside Hemodynamic Monitoring", *C. B. Mosby Co.*, 1985.

The tip 842 of catheter 840 is seen to be positioned within the pulmonary artery 812 upstream from the bifurcation 814. Adjacent the tip 842 is a partially inflated balloon 844. Positioned upstream in the sense of blood flow is a measurement region represented generally at 846 which is seen to incorporate an analyte concentration sensor 848. For the preferred embodiment wherein ammonia ($NH_3$) is the analyte component sensed, a pH sensor also will be located at the measurement region. Note, additionally, that this measurement region 846 is located in adjacency with the pulmonary valve 828. With this measurement region 846 positioning, it may be observed that the sensor or sensors at 848 are positioned centrally within the bloodstream by the valve 828. This avoids a positioning of the sensors 848 in adjacency with the wall of the pulmonary artery 812 to avoid, in turn, loss of sensitivity due to the hydraulic wall effect. In the latter regard, the velocity of a fluid within a conduit at a wall surface is considered to be zero for analytic purposes. Catheters as at 840 conventionally are multi-channeled and formed of a soft or compliant material so as not to unduly interfere with the valve activities of the right side 792 of heart 790. Typically, the devices as at 840 will have a diameter of about 7.5 French (0.09 inch) and a length of about 40 inches extending from an externally disposed proximal end (not shown). The devices are introduced into the body percutaneously as in the embodiment of FIG. 3, normally being entered from the subclavian vein and the jugular vein at the shoulder/neck region or alternately from a femoral vein in the leg. Devices 840 are termed as "flow directed" movement into position being achieved as a consequence of blood flow by virtue of the partially inflated balloon 844. Correspondingly, the proper positioning of the tip 842 and measurement region 846 is confirmed, for example, by the pulmonary blood pressure waveform developed by utilization of an open-ended fluid filled channel or lumen extending through catheter 840. Insertion of the catheter 840 is stopped when a pressure monitor employed with the blood pressure channel exhibits an appropriate pressure profile. Tip region 842 may contain a temperature sensor for alternate utilization of the cold bolus procedure for measuring cardiac output. Located upstream in the sense of blood flow, an analyte-containing fluid injectate or infusion port of catheter 840, shown at 850, serves to infuse or express such solution into the bloodstream at a controlled mass flow rate. Such infusion into the bloodstream occurs in the region shown, i.e., at the entrance to and within the right atrium. The expression of such fluid and its dilution is shown in the figure as a density of "dots". The dots are representative of dilution occurring during or very shortly following the interval of infusion. It may be recalled that for TCBV measurements, the dilution will be to an extent wherein a thorough mixing of the analyte in blood will have occurred such that the descending component of the concentration curve is evolved. The procedure of the invention also can be carried out with a catheter introduced through a major artery into the left side 794 of the heart 790. The procedure for measuring CO and TCBV are the same as discussed in connection with FIGS. 4–8.

Figures 37, 38:
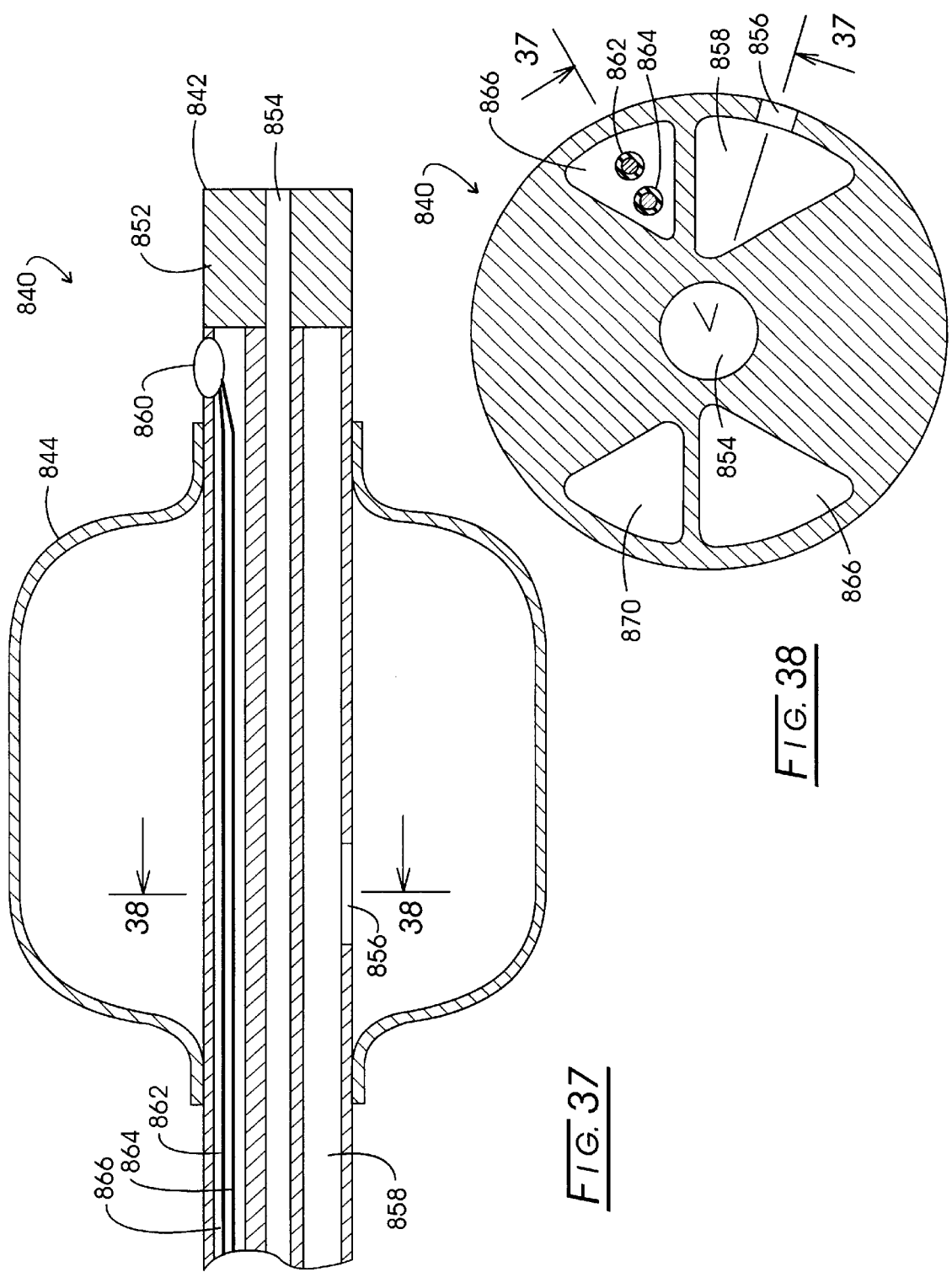
FIG. 37 is a sectional view of the catheter of FIG. 36 taken through the plane 37—37 shown in FIG. 38.
FIG. 38 is a sectional view taken through the plane 38—38 shown if FIG. 37.

Referring to FIGS. 37 and 38, the structure of catheter 840 in the region of its tip 842 is revealed in sectional fashion. FIG. 37 is a developed view taken along the wedge-shaped section 37—37 shown in FIG. 38. While the latter figure is a sectional view taken along the plane 38—38 in FIG. 37. In FIG. 37, the tip 842 is shown to include a polymeric collar 852 which functions to block certain of the channels of the catheter and to provide end support for a blood pressure channel. In this regard, channel or lumen 854 extends through the catheter 840 and carries a saline solution for purposes of transmitting blood pressure witnessed at the tip 842. Balloon 844 is inflated from an internally disposed port 856 which, in turn, is in gas flow communication with a lumen or channel 858. Channel 858 is blocked at the collar 842 and receives an inflating gas such as carbon dioxide as earlier described. A temperature sensor 860 is shown positioned adjacent the collar 842 which may be provided as a thermister or the like. Device 860 is controlled and monitored by two electrical leads 862 and 864 which extend to connection with a controller (not shown) and which are located within a channel or lumen 866 blocked by collar 842. FIG. 38 additionally reveals an analyte-containing fluid delivery channel 868 and an auxiliary IV channel 870. The latter two channels are blocked rearwardly adjacent their outlet ports, for example, port 850 shown in FIG. 36.

The preferred embodiment for the catheter 840 is one wherein the analyte component measured is ammonia ($NH_3$) which is measured using fiberoptic-based technology. For deriving total ammoniacal concentration, pH also is measured. While the latter parameter can be measured by more conventional methods, measurement for the instant embodiment of catheter 840 is carried at a location in adjacency with the measurement of ammonia content. Referring to FIGS. 39 and 40, the measurement region of catheter 840 is revealed in sectional detail. FIG. 39 reveals the continuation of blood pressure conduit 854. Adjacent that centrally disposed conduit is the analyte concentration sensor 848 here implemented in the manner of the sensor described in connection with FIG. 19. In this regard, the sensor 848 is configured with an optical fiber 872 the surface of which is clad and which extends within a channel 874 to a tip or face 76. The reactor and support components of the sensor 848 include a subassembly that incorporates a porous polymer reactor support within which an analyte, i.e., ammonia sensitive dye is immobilized. Bonded to the inward face of that support is a nonporous optically transparent polymer or backer component which, in turn, is adhesively attached to the fiberoptic face 876. Note that the forward surface 878 of the sensor 848 is retracted within the channel 874 which extends along a transition region represented generally at 880 to an opening or port 882. Once the catheter 840 is in appropriate position, then the fiberoptic component 872 is pushed forwardly such that the surface 878 is immersed within flowing blood. That orientation is shown in connection with the pH measurement component of catheter 840.

Figure 20:
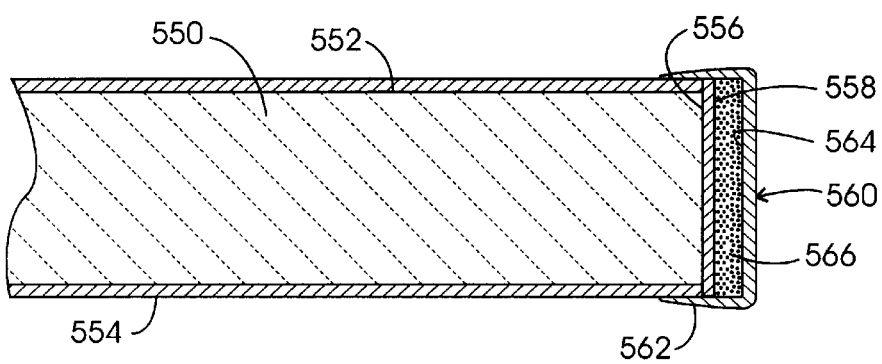
FIG. 20 is a schematic representation of a pH sensor which may be employed with the invention.

Diametrically spaced from the sensor 848 is a pH sensor represented generally at 890 performing in the manner described in conjunction with FIGS. 19 or 20, the sensor 890 is configured having an optical fiber 892 positioned within a channel or lumen 894 extending from connection with a manipulator and controller (not shown) to a tip or face 896. For sensor configured under the embodiment of FIG. 19, as before, a subassembly is developed which is provided as a porous polymer reactor support within which a pH sensitive dye may be immobilized. That support is bonded with an optically transparent polymeric backer component which, then, is adhesively attached to the face 898. Upon the positioning of the catheter 840 at a location for measurement, the fiberoptic component 892 is maneuvered forwardly from a retracted position similar to that illustrated in connection with sensor 848 above. As the fiberoptic component 892 is urged forwardly, the forward face 898 of the sensor moves through a transition region 900 and opening 902 to be immersed within blood flowing within the bloodstream. This deployed orientation is represented in the figure. Prior to withdraw of the catheter 840, the analyte or ammonia concentration sensor and the pH sensor may be retracted back to the orientation shown with respect to sensor 848. Similar to the sensor 848, the pH sensor 890 is controlled from a controller (not shown).

Figure 41A:
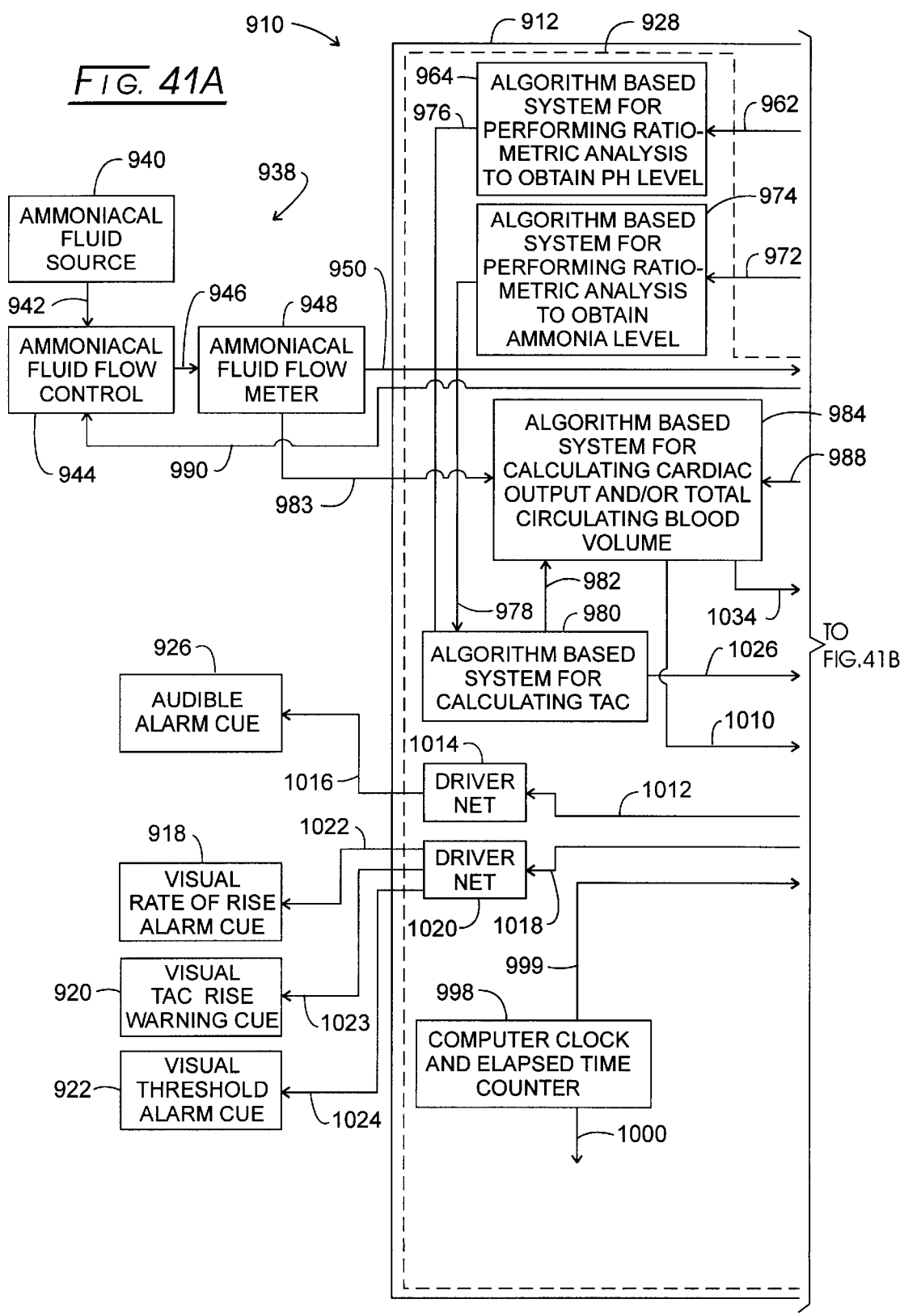
FIGS. 41A and 41B combine as labeled thereon to provide a block diagram of a control system configured according to the invention.
Figure 41B:
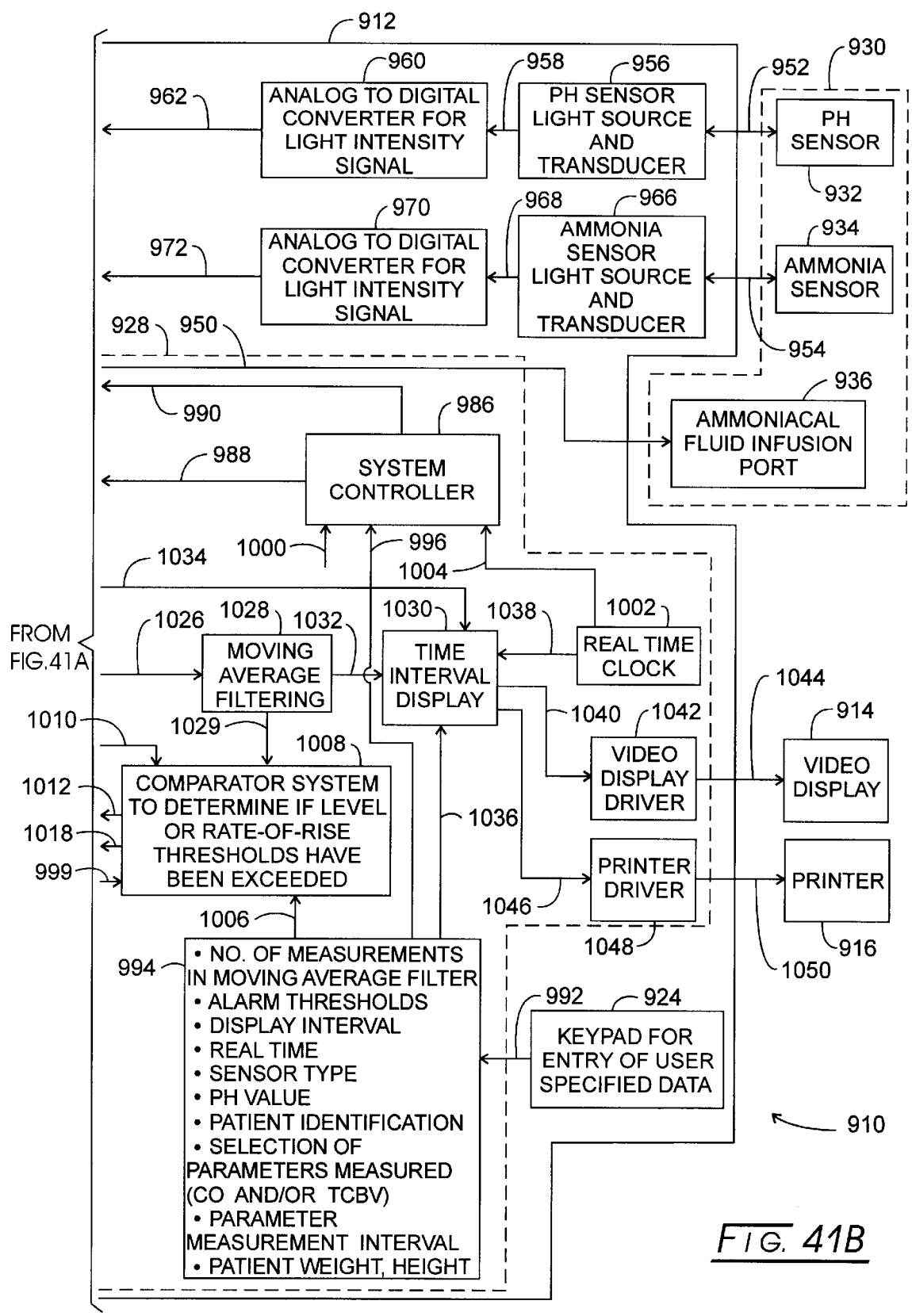

Referring to FIGS. 41A and 41B, a block diagram is provided illustrating the overall system 910 of the invention. In the figure, a controller is represented within the boundary 912. This controller 912 will function as described in conjunction with controller 214 illustrated in FIG. 9. The video display earlier described at 230 is seen at block 914, while the printer function described at 232 is represented at block 916. The LED warning and alarm output described at LED array 238 and FIG. 9 now is represented at blocks 918, 920 and 922. Similarly the array of keys 226 are represented at block 924 and an audible alarm cue is represented at block 926. Controller 912 is microprocessor driven and the microprocessing or software functions of it are represented within a dashed boundary 928.

System 910 is configured in accordance with the preferred arrangement of the invention wherein the analyte containing fluid is an ammoniacal fluid and the analyte component monitored is ammonia gas ($NH_3$), an election which further requires the value of pH of the blood. Preferably, this pH value is monitored within the vascular system of the body somewhat in adjacency with the ammonia monitoring function. Recall that the embodiments of FIGS. 10 and 34 provide sensor functions which include a pH measurement either within a common catheter structure or utilizing two distinct sensing instruments. The bloodstream of the patient is represented in the drawings within dashed boundary 930, a pH sensor function being represented at block 932 and an ammonia sensor being represented at block 934. An ammoniacal fluid infusion port within the bloodstream 930 is represented at block 936 and the delivery system for so infusing this ammoniacal fluid is represented in general at 938. Within the system 938, block 940 is seen to represent an ammoniacal fluid source as described in conjunction with FIG. 9 at 220. Source 940 is delivered, as represented at arrow 942 to an ammoniacal fluid flow control represented at block 944. Flow control 944 performs, as represented by arrow 946 and block 940 with an ammoniacal fluid flow meter represented at block 940 to provide a controlled mass flow rate fluid delivery for infusion as represented at arrow 950 directed to port 936. Arrow 950 corresponds with conduit 108 and port 936 corresponds with tip 106 of the delivery apparatus of FIG. 9.

A fiberoptic based approach is preferred for the ammonia and pH sensing function represented at blocks 932 and 934. Optical interaction of these sensing devices with the controller 912 is represented by dual directional arrows shown respectively at 952 and 954. The fiberoptic input and interrogation represented at arrow 952 is directed to a pH sensor light source and transducer function as represented at block 956. The pH related analog signals evoked from this function at block 956 are directed, as represented at arrow 958, to an analog-to-digital conversion function represented at block 960. The resultant digitized pH value then, as represented at arrow 962 is introduced to the microprocessor function 928 and a software program carries out a ratiometric analysis to obtain pH level as represented at block 964.

Correspondingly, the interactive fiberoptic signals at arrow 954 are controlled from an ammonia sensor light source and transducer function represented at block 966. Light intensity related analog signals corresponding with ammonia concentration then, as represented at arrow 968 are digitized, as represented at block 970. Resultant digital signals, having been converted at the analog-to-digital function block 970, then are directed to the processor function as represented by arrow 972. Arrow 972 is seen to be directed to the software algorithm function represented at block 974 wherein a ratiometric analysis is carried out to obtain ammonia levels. A pH level or value and ammonia level concentration value, then, as represented at respective arrows 976 and 978 are directed to an algorithm-based system which functions to calculate total ammoniacal concentration (TAC).

Total ammoniacal concentration in blood, $C_a$ may be computed by applying the well known Henderson-Hasselbalch equation with respect to the equilibrated ammonia gas-ammonium ion $(NH_3)$–$(NH_4^+)$ system. See generally in this regard:

Hindfelt, D., "The Distribution of Ammonia Between Extracellular and Intracellular Compartments of the Rat Brain", Clinical Science and Molecular Medicine, Vol 48, pp 33–37, (1975).

The relative distribution of ammonia gas $(NH_3)$ and ammonium ion $(NH_4^+)$ in solution is given by that Henderson-Hasselbalch equation as follows:

$$pH = pK_a + \log \frac{[C_a(NH_3)]}{[C_a(NH_4^+)]} \quad (6)$$

This equation can be restated in terms of the unknown $Ca(NH_4^+)$ as follows:

$$C_a(NH_4^+) = C_a(NH_3)/[10 \exp (pH-pK_a)] \quad (7)$$

where
$C_a(NH_4^+)$=concentration of ammonium ions $(NH_4^+)$ in blood (micromole/liter)
$C_a(NH_3)$=measured concentration of ammonia gas $(NH_3)$ in blood (micromole/liter)
pH=measured blood pH
pKa=pH level of solution above which all ammonia exists as a gas $(NH_3)$ where pKa=9.15 (Hindfelt, ibid).

The total ammonia content of the blood, $C_a$ (total) may be calculated as follows:

$$C_a(total) = C_a(NH_3) + C_a(NH_4^+) \quad (8)$$

Figure 6:
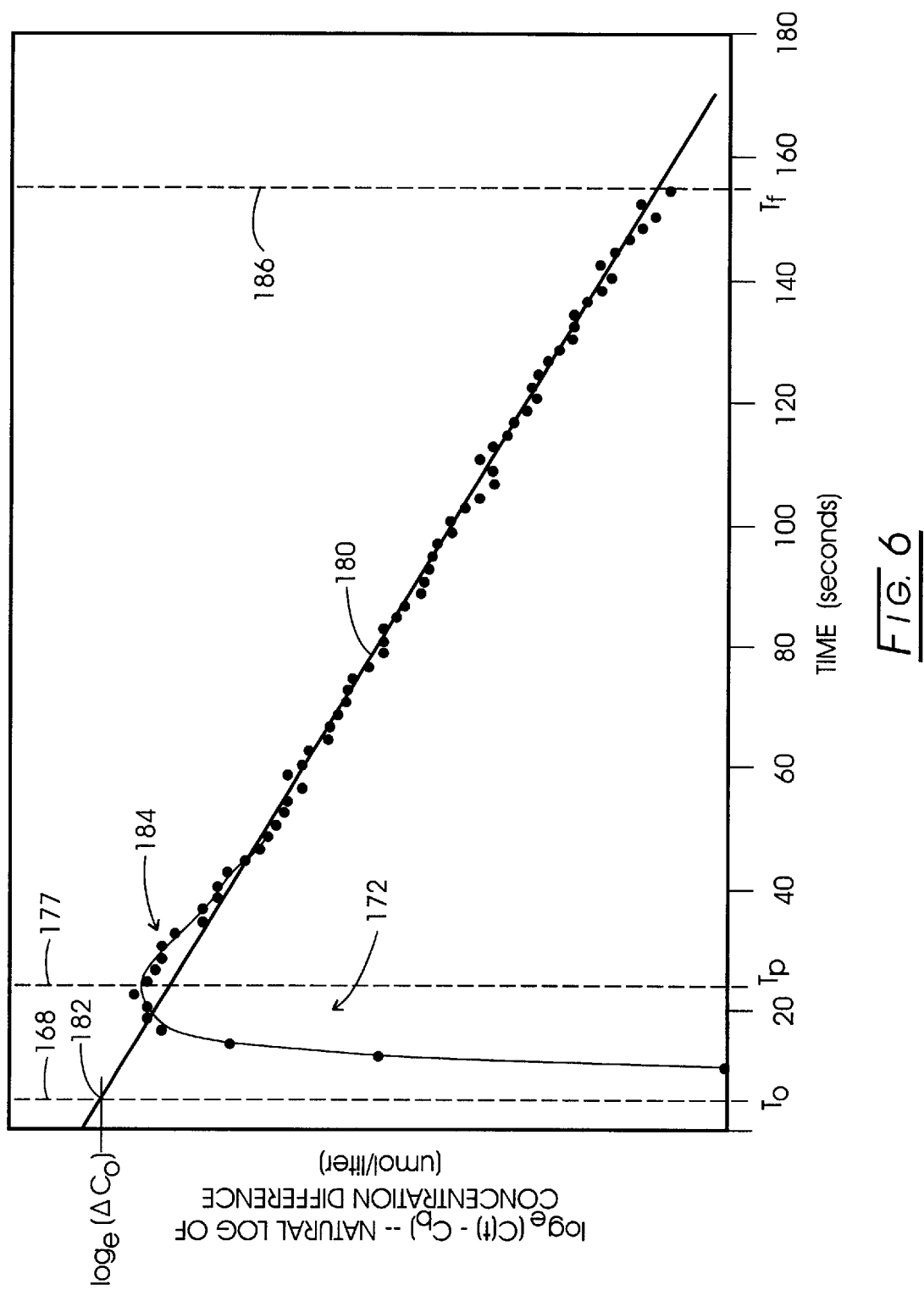
FIG. 6 is a plot of the concentration curve of FIG. 5 employing a semi-log format.

The above computations are represented at block 980. These measurements evolving TAC are carried out with substantial rapidity, for example, as illustrated in FIG. 6 above in order to, in effect, define the concentration curve. In turn, the concentration curves are evolved with relative rapidity, for example, each two to three minutes for CO and each four to eight minutes for TCBV. The TAC values are utilized at the option of the practitioner in a number of different algorithms, for example, carrying out the equilibrium or non-equilibrium based evaluation of cardiac output (CO) and for determining total circulating blood volume (TCBV). Additionally, the ammoniacal level of the blood may be monitored for a variety of purposes to aid the practitioner in patient management.

Digital TAC values and fluid flow data are shown directed as represented respectively at arrows 982 and 983 to block 984 representing an algorithm function for calculating cardiac output (CO) and/or total circulating blood volume (TCBV). That algorithm, as represented at block 984, is seen to be under the control of a system controller as represented at block 986 and arrow 988. The controller function 986 provides for carrying out control based upon the type of CO measurement involved, i.e., equilibrium or non-equilibrium and for the infusion intervals and analyte-containing fluid mass flow rates, associated with them. Additionally, the controller effects control over the infusion rates and infusion intervals for TCBV. In the latter regard, the infusion rates generally are higher for that measurement and the infusion interval is selected as shorter in duration. Accordingly, control inputs are made to the ammoniacal fluid flow control at block 944 as represented at arrow 990.

The preferred equilibrium based approach for measuring CO as discussed in connection with expression (1) above initially may be expressed as follows:

$$CO(t_i) = \frac{K * m_I * [IC_a - C_a(t_i)]}{[C_a(t'_i) - C_a(t_i)]} \quad (9)$$

Where:
CO=cardiac output measured at time, $t_i$ (liters/minute);
K=constant;
$m_I$=mass flow rate of injection of ammoniacal fluid (liters/minute);
$IC_a$=total ammoniacal concentration of the analyte-containing fluid (predetermined analyte concentration) (micromol/liter);
$C_a(t'_i)$=total ammoniacal concentration of the analyte-containing fluid in blood measuring effect of infusion (micromol/liter);
$C_a(t_i)$=total ammoniacal concentration of analyte in blood measured prior to analyte infusion (baseline) (micromol/liter)

The measured volumetric output of the heart often is normalized to the size of the patient by dividing the measured cardiac output by the patient's "body surface area," BSA (estimated in square meters), the latter parameter generally being derived based on the height and weight of the patient. This normalized cardiac output value is referred to as the cardiac index, CI, and is given by the expression:

$$CI(t_i) = \frac{CO(t_i)}{BSA} \quad (10)$$

The value, CO as computed using the non-equilibrium method as discussed in connection with expression (4) above additionally may be expressed as follows:

$$CO = \frac{\dot{m} \times ID \times 60}{\int_{t_1}^{t_2} C^*(t) \, dt}$$

Where: CO=cardiac output (liters/minute)
$\dot{m}$=mass flow rate of indicator (micromol/second)

ID=duration of indication injection (seconds)
60=conversion of seconds into minutes
C*(t)=difference between c(t), total ammoniacal concentration at time, t, and $C_0(t)$, total ammoniacal concentration of baseline at time, t, (adjusted for recirculation) (micromol/liter*second)
$t_1$=the time at the commencement of the formation of the concentration curve($t_2$ in FIG. 8)
$t_2$=time of termination of the concentration curve ($t_3$ in FIG. 8)

Total circulating blood volume as discussed in connection with expression (3) above further may be expressed as follows:

$$\{TCBV\} = \frac{D_o}{\Delta C_o}$$

Where: TCBV=total circulating blood volume (liters)
$D_0$=dose of indicator infused in micromoles
$\Delta C_0$=extrapolated maximum concentration increase at time $T_0$ (FIG. 6)
$\Delta C_0 = \exp(\log_{e[\Delta C0]})$
$C_0$=mean infusion interval time Practitioner input to the controller function 986 is from the keypad feature represented at block 924, the output of which is represented at arrow 992 extending to block 994 providing a cataloging of the operational features to which the system 910 will respond. Certain of those features are utilized in conjunction with the controller function 986 as represented at arrow 996. In this regard, the practitioner may select alarm thresholds for both CO and TCBV. The sensor type is inserted. Where pH is not measured as represented at block 932, it may be entered manually when patient identification is entered for the record and the practitioner will select whether to measure either or both CO and TCBV. This parameter measurement interval, for example, each two minutes is elected by the practitioner and the patient weight and height is entered for the purpose of computing cardiac index (CI) from the computed CO value. System controller 986 additionally employs the computer elapsed clock and elapsed time counter function represented at block 998 as depicted by the dual arrows 1000. That function also is associated with comparator 1008 as represented by arrow 999. Additionally, it is desirable that the time of computation of CO and TCBV be associated with the data and this input to the controller function 986 is represented at block 1002 and arrow 1004.

The practitioner elected thresholds as cataloged at block 994 are directed, as represented by arrow 1006 to a comparator system or function represented at block 1008. Also directed to this function are the computed values of CO and TCBV as represented at arrow 1010. Accordingly, where CO or TCBV values exceed an upper threshold limit or fall below a lower threshold, then the comparator function 1008 provides outputs to alarm functions. In this regard, an output is provided as represented at arrow 1012 to a driver network represented at block 1014 to, in turn, provide an audio drive represented at arrow 1016 to the audible alarm cue function represented at block 926. Further, as represented by arrow 1018 and block 1020 the comparator function 1008 provides an input to a driver network to activate visual alarm cues. In this regard, network 1020 is coupled to drive a visual LED rate of rise alarm as represented at block 918 and arrow 1022. Correspondingly, the driver network serves to drive a visual threshold alarm cue at block 922 as represented by arrow 1024.

TAC values as are represented as baseline initially are monitored by the system 910. Returning to block 980, the system carries out a moving average filtering of these baseline TAC values as represented at arrow 1026 and block 1028. Such filtering serves to avoid update rates at a visual display which may become distracting to the practitioner. Thus, among the practitioner elected features set forth in block 994, the opportunity is present for electing a number, n, of measurements which are compiled or queued in a first (newest) in, last (oldest) out basis to provide a display both numerically and graphically which is "smooth" in its observable nature. The moving average filter is available for this purpose, inasmuch as very rapid excursions in ammoniacal concentration values will not occur in the realm of practical medical monitoring. Comparator function 1008 compares the filtered TAC value with the next previous filtered TAC value. Where a rise in filtered TAC value is determined, then as represented at arrow 1018, an appropriate signal is provided to Driver Network 1020 which, in turn, as represented by arrow 1023 and block 920, provides a TAC Rise Warning Cue. The input from Moving Average Filter is provided to comparator system 1008 as represented at arrow 1029.

Looking to the display function of system 910, the filtered TAC values as well as the values of CO and TCBV are directed to a time interval display feature at block 1030 as represented by respective arrows 1032 and 1034. The interval for such display is elected by the practitioner as set forth at block 994 and is represented at arrow 1036. Real time values are submitted to the function at block 1030 as represented at arrow 1038 and the resulting data is directed to a video display as at block 914 as represented by arrow 1040, driver block 1042 and arrow 1044. In similar fashion, data is provided at the printer function represented at block 916 as represented by arrow 1046, driver block 1048 and arrow 1050. The flow rate of the ammoniacal fluid flow as represented at block 940 also is employed for parameter computation as represented at arrow 983.

FIGS. 42A–42G combine as labeled thereon to present a flowchart describing the measuring and monitoring methodology of the invention. In the discourse to follow concerning that flowchart, a variety of system parameters are employed. These parameters are defined in the tabulation set forth in Table II below.

TABLE II i = index
t = real (actual) time
$t_i$ = real (actual) time of measurement of pH
$t_i'$ = real (actual) time of measurement of ammonia level in blood $C_a(t_i')$
$t_i''$ = next previous real (actual) time
$t_{ROR}$ = elapsed time from start @ time 0 for rate-of-rise (TAC)
$\delta t_{ROR}$ = time interval used for rate-of-rise calculation
$t_{REL}$ = elapsed time from start of each displayable measurement set (pH, TAC rate-of-rise)
ET = elapsed time between display of rate of change of TAC
RT = elapsed relative time
$\Delta T$ = display update interval for TAC
n = filter number
$\delta$ = interval between pH and ammonia measurement
$C_{TAC}(t_i')$ = total ammoniacal concentration (TAC) calculated for real time $t_i'$
$\bar{C}_{TAC,n}(t_i')$ = filtered TAC (n-value average taken at time of last TAC calculated) i.e., at time $t_i'$
$\dot{C}_{TAC}(t_i')$ = rate of change of TAC taken over interval, $\delta t_{ROR}$ $$\dot{C}_{TAC,n}(t_i') = \left\{ \frac{[\bar{C}_{TAC,n}(t_i') - \bar{C}_{TAC,n}(t_i''')]}{\delta t_{ROR}} \right\}$$

where $t_i''' = t_i' - \delta t_{ROR}$
$C_{th}$ = Threshold for adverse effects, TAC

TABLE II-continued $\dot{C}_{th}$ = Rate of Rise Threshold. TAC
ICa = Concentration of analyte in analyte-containing fluid (injectate)
$\dot{m}$CO = Infusion rate of analyte (indicator) (liters/second) during cardiac output measurement
IDCO = Infusion duration for analyte (indicator) (seconds) for cardiac output measurement
CO = Cardiac output (liters/minute)
CI = Cardiac index (liters/minute-miter$^2$)
BSA = Body surface area (meter$^2$)
ICA = Ammonium/ammonia concentration, i.e. indicator concentration (micromoles/liter)
TCBV = Total circulating blood volume (liters)
MICO = Inputted minimum time interval between cardiac output measurements (minutes); MICO usually > MITCBV.
MITCBV = Inputted minimum time interval between total circulating blood volume measurements (minutes)
$CO_{uth}$ = Upper threshold of cardiac output for adverse effects (liters/minute)
mTCBV = Infusion rate of analyte (indicator) during TCBV measurement (liter/second)
IDTCBV = Infusion duration for analyte (indicator) for TCBV measurement (seconds).
$CO_{lth}$ = Lower threshold of cardiac output for adverse effects (liters/minute).
$CI_{uth}$ = Upper threshold of cardiac index for adverse effects (liters/minute—m$^2$)
$CI_{lth}$ = Lower threshold of cardiac index for adverse effects (liters/minute—m$^2$).
$TCBV_{uth}$ = Upper threshold of total circulating blood volume for adverse effects (liters).
$TCBV_{lth}$ = Lower threshold of total circulating blood volume for adverse effects (liters)
$t_{CO}$ = Relative time elapsed between CO measurements (minutes).
$t_{TCBV}$ = Relative time elapsed between TCBV measurements (minutes).
COLAST = Flag indicating that the last parameter measured was cardiac output when value equals unity, i.e., (COLAST = 1).
TCBVET = Relative time at beginning of each TCBV measurement cycle (minutes)
TCBVMD = Measurement duration of TCBV measurement, factory set (minutes).
TCBLAST = Flag indicating that last parameter measured was total circulating blood volume when value equals unity, i.e., (TCBVLAST = 1).
COET = Relative time at beginning of each CO measurement period (minutes)
COMD = Measurement duration of CO measurement (factor set minutes)
CO FLAG = Flag indicating that it is time for cardiac output measurement.
TCBVEST = Estimated total circulating blood volume; this parameter is calculated based on sex, height and weight of patient (liters); used in recirculation correction algorithm for calculation of cardiac output.
TCBVFLAG = Flag indicating that it is time for total circulating blood volume measurement.
CT = Cumulative time clock which is reset to zero each time TAC is displayed and/or printed.

Figure 42A:
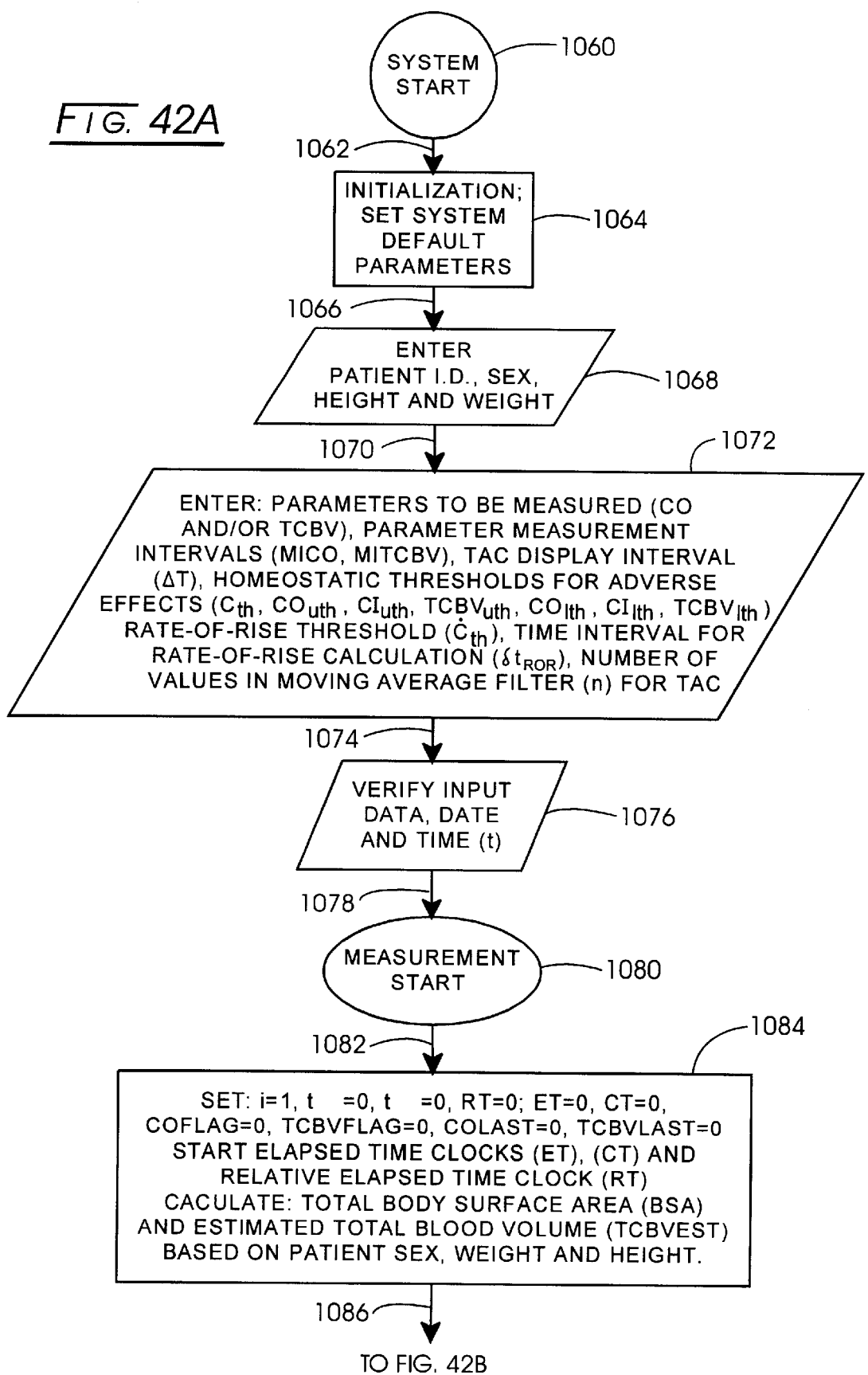
FIGS. 42A–42I combine as labeled thereon to provide a flowchart describing the operation of a controller employed with the invention.

Referring to FIG. 42A, system start is represented at node 1060 and arrow 1062. At startup, as represented at block 1064, conventional initialization activities are carried out, including the entry of any default parameters. Then, as represented at arrow 1066 and block 1068, patient identification including sex, height and weight is added at the keypad as described in conjunction with block 924 (FIG. 41B). It may be recalled that cardiac index, (CI) is computed in conjunction with BSA which, in turn, is developed from sex in combination with height and weight values. As represented at arrow 1070 and block 1072, the practitioner then enters the hemodynamic parameters to be measured, i.e., CO and/or TCBV. Additionally entered are the parameter measurement intervals (MICO) which is the measurement interval minimum between CO measurements in minutes; and MITCBV is the measurement interval minimum between TCBV measurements in minutes. The practitioner also enters the TAC measurement display interval, ΔT. Homeostatic thresholds for adverse effects are entered. These thresholds include: $C_{th}$ which is the TAC threshold for adverse effects; $CO_{uth}$ which is the upper threshold of CO for adverse effects; $CI_{uth}$ which is the upper threshold of CI for adverse effects; $TCBV_{uth}$ which is the upper threshold of TCBV for adverse effects; $CO_{lth}$ which is the lower threshold of CO for adverse effects; $Cl_{lth}$ which is the lower threshold for CI; and $TCBV_{uth}$, which is the lower threshold of TCBV for adverse effects. Additionally entered are the TAC rate-of-rise threshold, $\dot{C}_{th}$, the time interval for the rate-of-rise calculation ($\delta t_{ROR}$); and the number of values(n) in the moving average filter for TAC. Then, as represented at arrow 1074 and block 1076, the real time, i.e., time of day and date is entered by the practitioner. As represented at arrow 1078 and symbol 1080, the measurement function of the system then commences. As represented at arrow 1082 and block 1084 an index, i, is set to one. The elapsed time, $t_{REL}$ from the start of each displayable measurement is set equal to zero. The parameter $t_{ROR}$, which is the elapsed time from the start at time zero for rate-of-rise of TAC is set to zero. The elapsed time between displays, RT, is set to zero and the elapsed time, ET, between display of rate of change of TAC is set to zero, and the clock CT is set to zero. The flags: "COLAST, TCBVLAST, COFLAG, and TCBVFLAG are set to zero. Total body surface area (BSA) and estimated total blood volume (TCBVEST) are calculated based upon the sex, weight and height of the patient. Then, the elapsed time clocks (ET) and (CT) and the relative elapsed time clock (RT) are started. The program then continues as represented at arrow 1086 and block 1088 wherein a query is posed as to whether a system stop command has been received. In the event that it has been received, then as represented at arrow 1090 and node 1092, the program ends. In the, event that no system stop command has been received, then as represented at arrow 1094 and block 1096, the pH of the blood is measured at time, $t_i$. In this regard, the system at hand is one wherein ammonia gas concentration is measured and combined with a corresponding pH measurement to derive total ammoniacal concentration. The program then continues as represented at arrow 1098 and block 1100 which provides for measuring the ammonia concentration at the time, $t'_i$ which is the real or actual time of measurement of ammonia level in blood, $Ca(t'_i)$. Symbol δ, represents the interval between measurement of pH and ammonia content. Following such measurement, as represented at arrow 1102 and block 1104 total ammoniacal concentration in blood (TAC) is computed and that computation is assigned the real or actual time, $t'_i$. The resultant value is represented as: $C_{TAC}(t'_i)$. That time to be associated with this TAC is established as the time of ammonia concentration measurement, $t'_i$. As represented at arrow 1106 and block 1108, the system then sets the relative time elapsed between CO measurements, $t_{CO}$; and the relative time elapsed between TCBV measurements, $t_{TCBV}$ as equal to the elapsed relative time RT. The relative time or elapsed time from the start of each displayable measurement, $t_{REL}$ is set to CT. Initially, the elapsed time from the start for determining TAC rate-of-rise, $t_{ROR}$ is set equal to elapsed time, ET as is provided as an elapsed time counter which, in general, is not reset. Next, as represented by arrow 1110 and block 1112, a query is posed as to whether the relative time elapsed between CO measurements, $t_{CO}$ is greater than or equal to the inputted minimum interval between the cardiac measurements, MICO. It may be noted that the interval MICO typically is less than the corresponding inputted minimum interval between TCBV measurements, MITCBV. In the event that an affirmative/determinator occurs with respect to the query posed at block 1112, then as represented at arrow 1114 and block 1116 the cardiac output measurement flag, COFLAG, is set to one. The program then continues as represented at arrow 1118. Where the determination at block 1112 is that the relative time elapsed between CO measurements is not greater or equal to the inputted minimum interval between cardiac output measurements, then as represented at arrow 1120 and block 1122, a query is posed as to whether the relative elapsed time between TCBV measurements is greater than or equal to the inputted measurement interval between TCBV measurements. In the event of an affirmative determination, then as represented at arrow 1124 and block 1126 the flag indicating that the measurement time is at hand for measuring TCBV is set to one. The program continues as represented at arrows 1128 and 1118. In the event of a negative determination with respect to the query posed at block 1122, the program diverts as represented at arrow 1130 to carry out TAC monitoring measurements. With the logic, provided by the decision blocks 1112 and 1122, a determination is made as to which hemodynamic parameter measurement flag is to be set based upon their respective minimum measurement intervals and the knowledge that MICO is usually quite smaller than MITCBV. For example, the time interval between cardiac output measurements (MICO) may be about three minutes, while the time interval between TCBV measurements (MITCBV) for example, may be about eight minutes if both CO and TCBV are selected for measurement, and about four minutes if only TCBV is selected for measurement. Following the setting of one or the other of the flags as represented at blocks 1116 and 1126, the program proceeds as represented at arrow 1118 to identify which of these flags has been set. In this regard, arrow 1118 extends to block 1132 wherein a query is posed as to whether the cardiac output flag has been set to one. In the event that it has, then as represented at arrow 1114 and block 1136 a query is posed as to whether the COLAST flag is set to one. The COLAST flag indicates that the last hemodynamic parameter measured was CO where the flag has been set to unity. In general, if both TCBV and CO are to be measured, they will be so measured in a sequence of one following the other. In this regard, if the last measurement was CO, then the system proceeds to measure TCBV and CO will be measured on the next measurement cycle. Accordingly, in the event of a negative determination with respect to the query posed at block 1136, then as represented at arrow 1138 and block 1140 CO measurement is commenced and the COLAST flag is set to one and the relative time at the beginning of cardiac output measurement, COET is set equal to the elapsed time RT. Next, as represented at arrow 1142 and block 1144 infusion of the analyte-containing fluid is commenced. That fluid will have a known analyte concentration, $IC_a$ and the injectate will be infused at a fixed and predetermined infusion rate, mCO, and for an infusion duration selected for the measurement of CO, IDCO. In general, this latter value will be greater than the corresponding infusion interval for TCBV. Correspondingly, the infusion rate typically will be slower than the corresponding rate for the infusion carrying out measurement of TCBV. The program then proceeds as represented at arrow 1146 and block 1148 in carrying out the measurement of blood pH at the actual time, $t_i$ i.e., pH $(t_i)$. The program then continues as represented at arrow 1150 and block 1152 which provides for measuring the ammonia concentration at time $t'_i$, which is the real or actual time of measurement of ammonia level in blood, $C_a(t'_i)$. The symbol, δ, represents the interval between the measurement of pH and ammonia content. Following such measurement, as represented at arrow 1154 and block 1156, total ammoniacal concentration in blood (TAC) is computed and that computation is, assigned the actual or real time, $t'_i$. The resultant value is represented as: $C_{TAC(t'i)}$.

The program then proceeds as represented at arrow 1158 and block 1160 whereat a determination is made as to whether the elapsed relative time from the measurement start represented at symbol 1080 less the value of COET which, at block 1140 will have been set to the value RT and retains that value until the next program cycle. The difference (RT-COET) is then compared with COMD which is a factory set measurement duration for carryout CO measurement. Until a condition of "equality" or "greater than" is met, measurements continue to be taken as represented by loop line 1162. This provides for the identification of a peak value as discussed in connection with FIG. 4. When an affirmative determination is developed with respect to the query at block 1160, then as represented at arrow 1164 cardiac output and cardiac index are computed and are assigned a real or actual time $t'_i$. The resultant values are identified as: $CO(t'_i)$ and $CI(t'_i)$.

The program then continues as represented by arrow 1168 and block 1170. Block 1170 provides for the display of cardiac output and cardiac index as well as total circulating blood volume. Additionally, the last computed filtered or average total ammoniacal concentration in blood (TAC) and pH measurement most recently taken are displayed in association with the real time $t'_i$. Those values are symbolically identified as: $CO(t'_i)$; $CI(t'_i)$; $TCBV(t'_i)$; $t'_i$; $\overline{C}_{TAC,n}(t'_i)$ and pH $(t'_i)$. As a correlative to this display of numerical values, as represented at arrow 1172 and block 1174, the system generates real time graphics displaying a time versus TAC value curve, as well as an associated TAC level threshold. Additionally, time based curves are generated showing running pH values, cardiac output, cardiac index and total circulating blood volume. The last entries to these curves are presented with respect to the real time $t'_i$. Correspondingly, a printed document or strip may be generated as represented at arrow 1176 and block 1178. The program then carries out a sequence of threshold comparisons with respect to CO, CI and TCBV. As represented at arrow 1180 and block 1182, a determination is made as to whether the currently measured value of cardiac output is greater than the practitioner inserted upper threshold of cardiac output for adverse effects. Alternately, a determination is made as to whether the currently measured value of cardiac output is less than a practitioner inputted lower threshold of cardiac output for adverse effects. In the event that neither of those conditions is present, then the program continues as represented at arrow 1184. However, where either of the thresholds is passed, then as represented at arrow 1186 and block 1188, a visual warning is activated as described at block 922 in FIG. 41A and, as described in connection with block 926 of that figure, an aural alarm cue is sounded. The program then continues as represented at arrows 1190 and 1184 to the query posed at block 1192. This query compares the currently measured value for cardiac index with a practitioner inputted upper threshold value for cardiac index. Alternately, the contemporaneous value for cardiac index is compared with a cardiac index lower threshold. Where neither of these thresholds are passed, then the program continues as represented at arrow 1194. However, in the event that either the upper or lower threshold for cardiac index has been passed, then as represented at arrow 1196 and block 1198 the above-noted threshold visual warning and aural alarm cues are activated to alert the practitioner. Following the generation of these cues, as represented at arrows 1200 and 1194, the program progresses to the query posed at block 1202. This query compares the recently measured value for TCBV with an upper threshold level for TCBV which will have been inputted by the practitioner, and it further compares that most recent value for TCBV with a lower threshold value for that parameter as inputted by the practitioner. The computed value for TCBV will have entered the program from that measuring function as represented by arrow 1204. Where neither the upper nor the lower threshold is passed, then the program continues as represented at arrow 1206. However, where either of these thresholds is passed, then, as represented by arrow 1208 and block 1210, the visual warning and aural alarm cues are activated as above discussed. The program then continues as represented by arrows 1206 and 1212 to the activity at block 1214 wherein the elapsed relative time, RT and an index i, are set to zero. At this time in the program, the measurement of hemodynamic parameters of CO or TCBV will have been completed. These parameter measurements require substantially more time to complete than, for example, TAC measurement and thus, in effect, a new cycle for their measurement is undertaken and the zeroing activity of block 1214 is appropriate. Following such zeroing activity, as represented at arrows 1216 and 1218, the program increments the index, i, by one as represented at block 1220 and continues to arrow 1094 as represented at arrow 1222. (FIG. 42B)

Returning to FIG. 42C and block 1132, where it is determined that the cardiac output flag (COFLAG) is not at a one value, then as represented at arrow 1224 and block 1226, a determination is made as to whether the TCBV-FLAG has been set to a one value. Where it has not been so set to a one value, then as represented at arrows 1228 and 1130 the program commences to carry out TAC measurements and associated running average filtering. This same test as represented at block 1226 is entered, as represented at block 1136 and arrow 1230 when the cardiac COLAST flag showing that cardiac output was last measured is at a one value. This logic provides for the alternation between the measurement of CO and the measurement of TCBV.

Where the TCBV flag has been set to a value of one, then as represented at arrow 1232 and block 1234, COLAST, the flag indicating that the last parameter measured was CO, is set to zero and the program continues as represented at arrow 1236 and block 1238. Block 1238 describes the commencement of the measurement of total circulating blood volume and, in this regard, similar to the activity at block 1140, the flag TCBVLAST representing that TCBV measurement is now the last measurement taken is set to one. Additionally, the term, TCBVET representing relative time at the beginning at each TCBV measurement cycle is set equal to the elapsed relative time, RT. Similar to the procedure represented at block 1140, this term, TCBVET remains constant throughout the instant measuring procedure. The program then continues as represented at arrow 1240 and block 1242. The latter block provides for the commencement of infusion of analyte-containing fluid or injectate. This fluid will have a known concentration of analyte ($IC_a$) and the infusion mass flow rate or rate of analyte infusion, mTCBV will be fixed and the infusion duration, IDTCBV, will be a predetermined interval. Next, as represented at arrow 1244 and block 1246, blood pH is measured at time, $t'_i$, to provide the value designated as pH ($t_i$). The program continues as represented at arrow 1248 and block 1250 to the measurement of the ammonia concentration in blood at a time, $t'_i$ which represents the time for measuring pH, $t_i$ plus the increment, δ to provide the quantity $C_a(t'_i)$. Upon deriving the latter value, as represented at arrow 1252 and block 1254, total ammoniacal concentration in blood (TAC) is calculated and the value is assigned the time, $t'_i$ as the time of TAC measurement occurrence. This value is represented as: $C_{TAC}(t'_i)$. The program continues as represented by arrow 1256 to the query posed at block 1258. A determination similar to that described in conjunction with block 1160 then ensues wherein the difference between elapsed relative time, RT and the term TCBVET, which was initially set at the value of RT, is compared with the factory established duration for the measurement of TCBV, identified by the term TCBVMD. As the number of measurements progress, the value of the elapsed relative time, RT will increase while the value of the term TCBVET will remain constant until the program again cycles to block 1238. Where the test posed at block 1258 is not met, then, as represented at arrow 1260 the program sub-loops to arrow 1244 to continue the derivation of TAC measurements and evolve a concentration curve (FIG. 5). When the test posed at block 1258 results in an affirmative determination, then as represented at arrow 1262 and block 1264, total circulating blood volume is calculated and assigned the time, $t'_i$, representing the time assigned to the most recent TAC derivation. This parameter is represented as: $TCBV(t'_i)$. The program then proceeds as represented at arrow 1204 to the test posed at block 1202 determining whether the inputted thresholds for TCBV have been passed. Following that activity, the program returns as represented at arrows 1206 and 1212. The resetting activities at block 1214 are carried out and the program then continues as represented at arrows 1216 and 1218 to index incrementation at block 1220 and via arrow 1222 to arrow 1094 to recommence baseline TAC measurement.

Figure 42B:
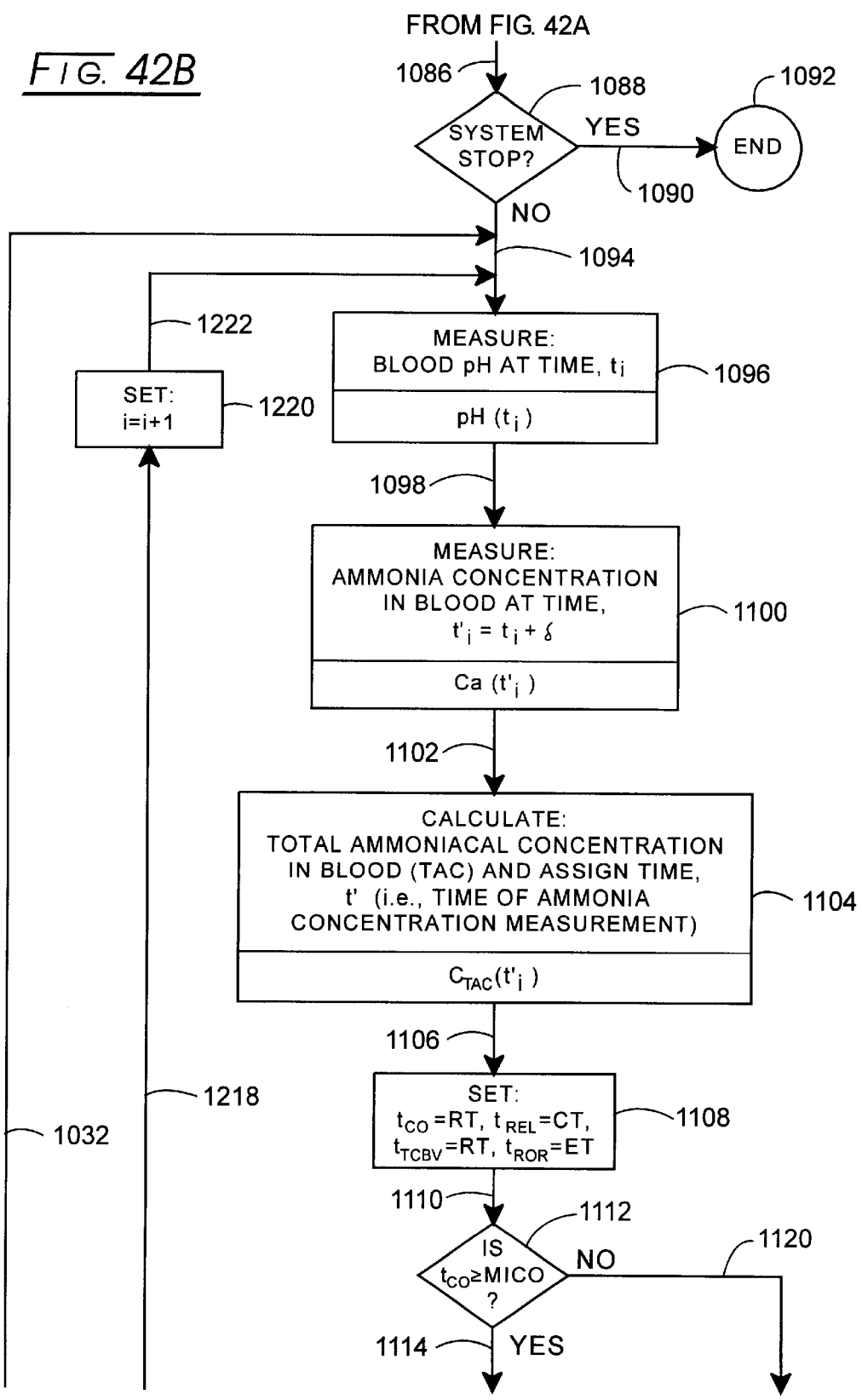
Figure 42C:
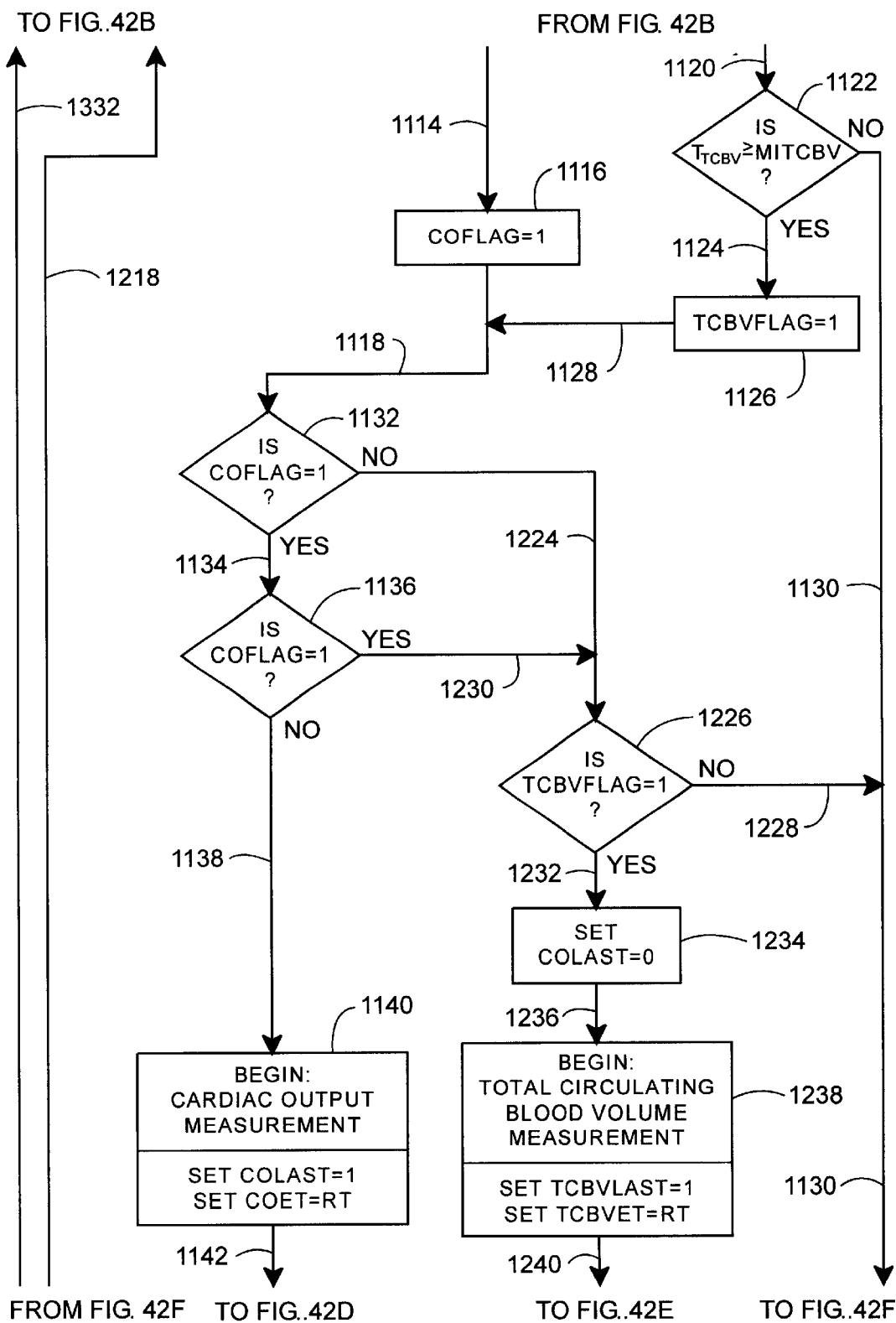
Figure 42D:
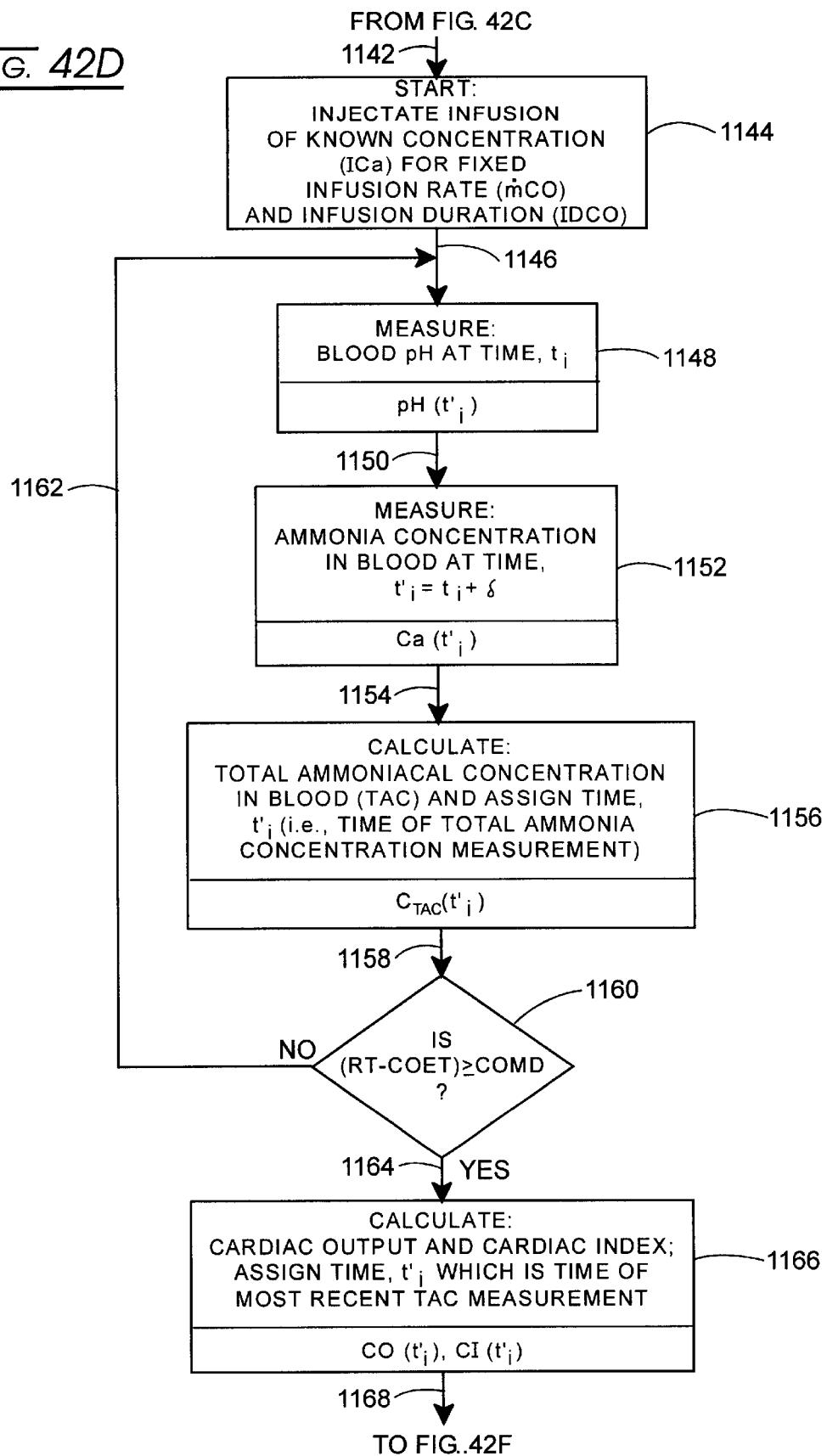
Figure 42E:
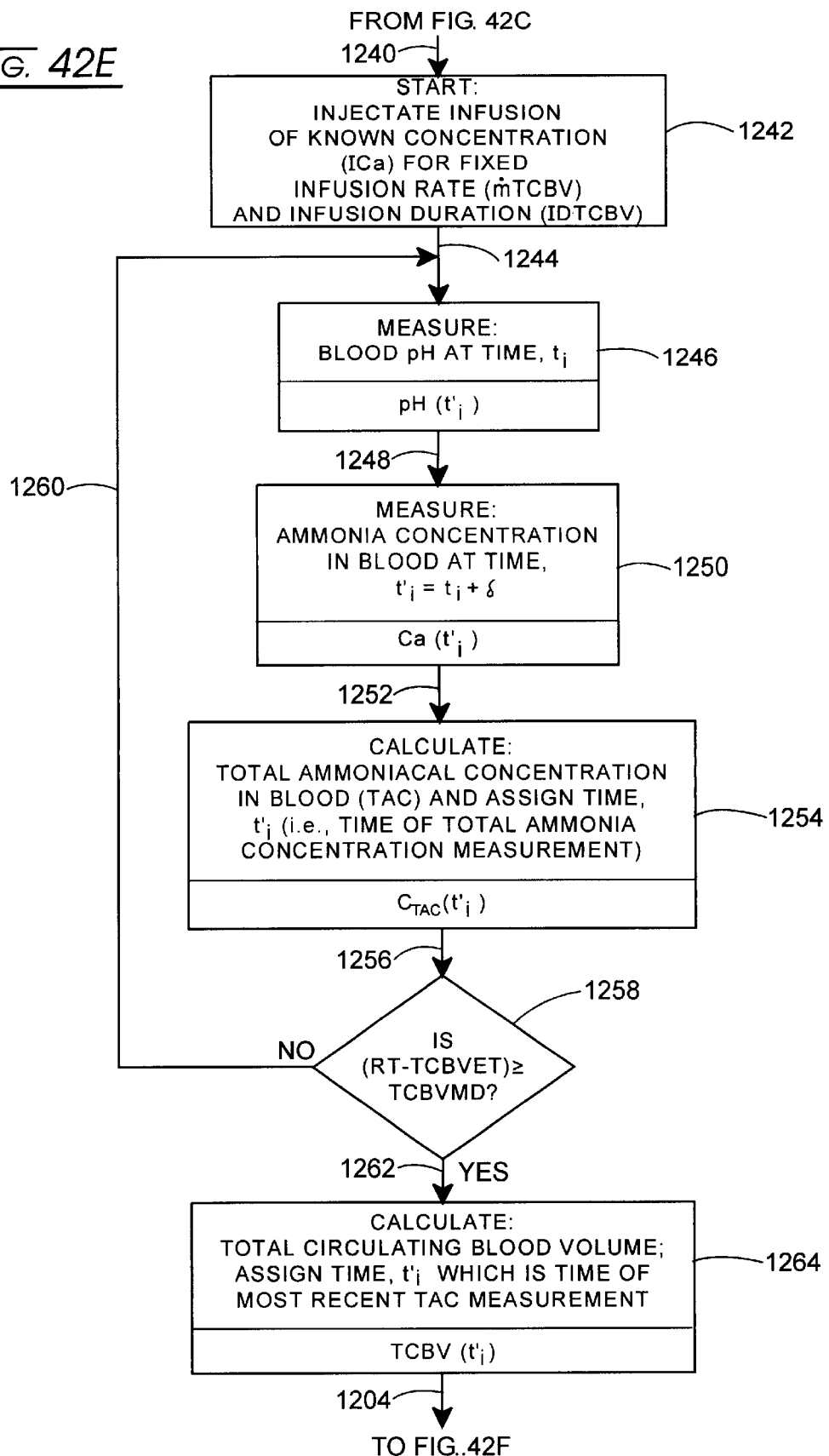
Figure 42F:
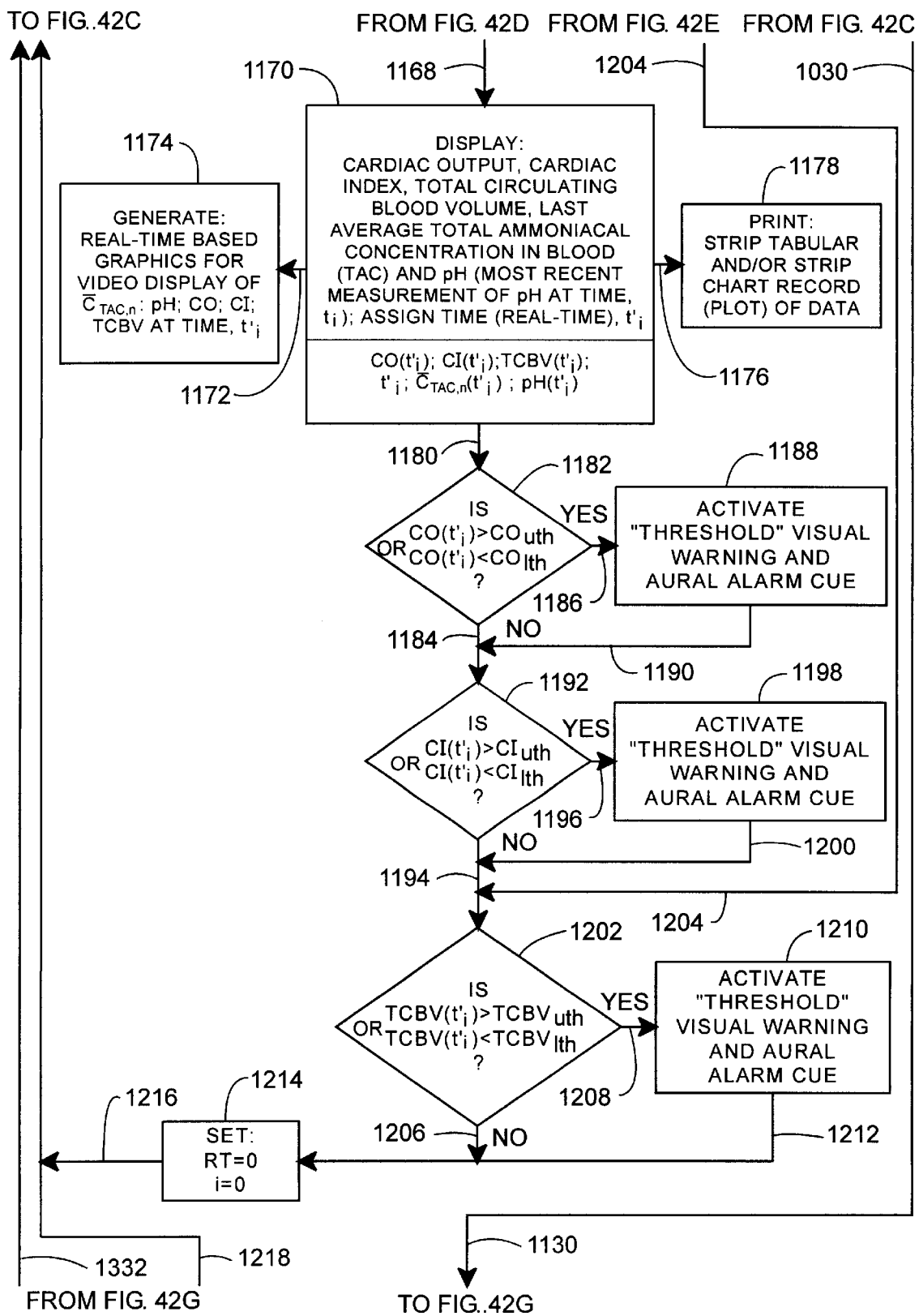
Figure 42G:
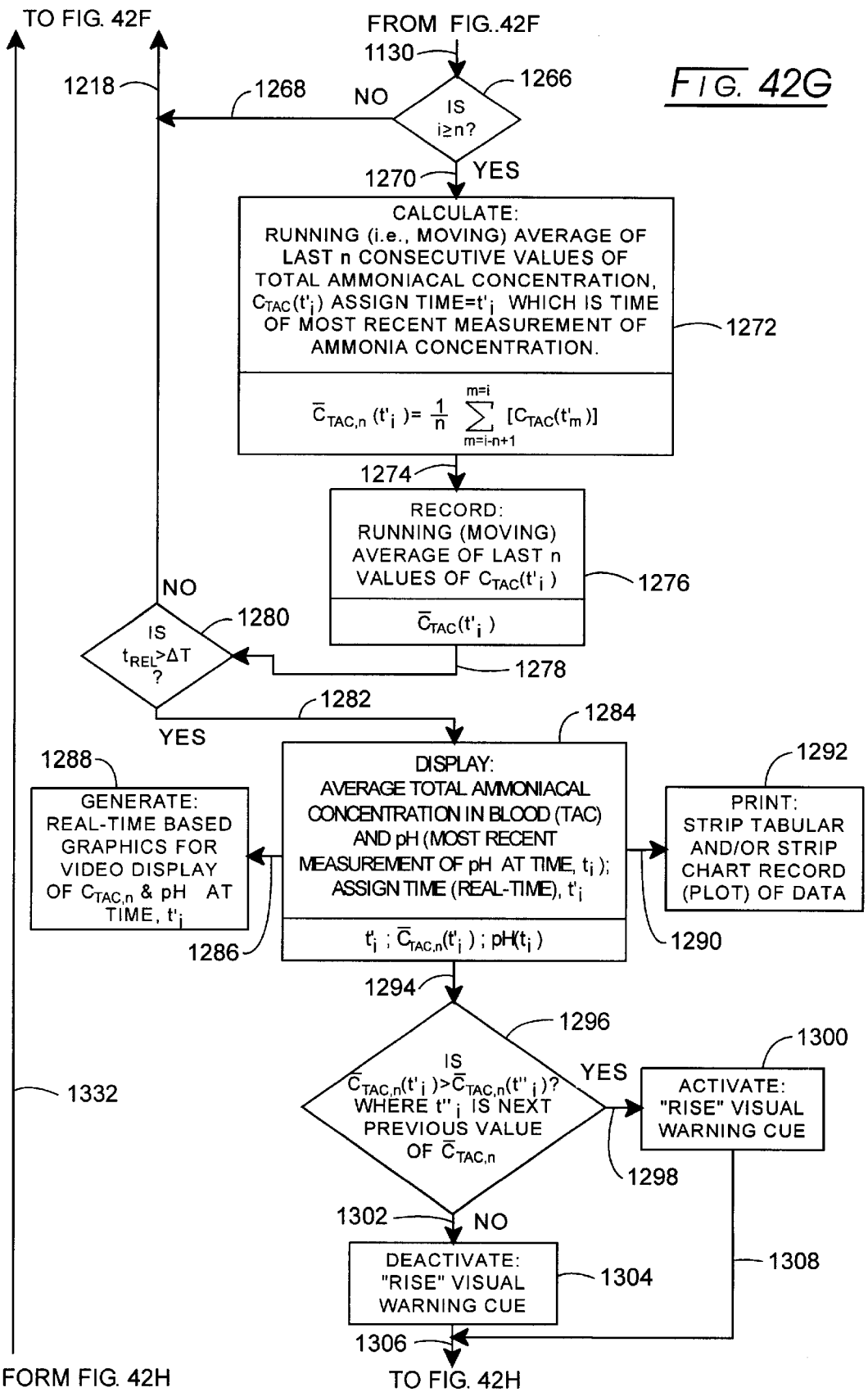
Figure 42H:
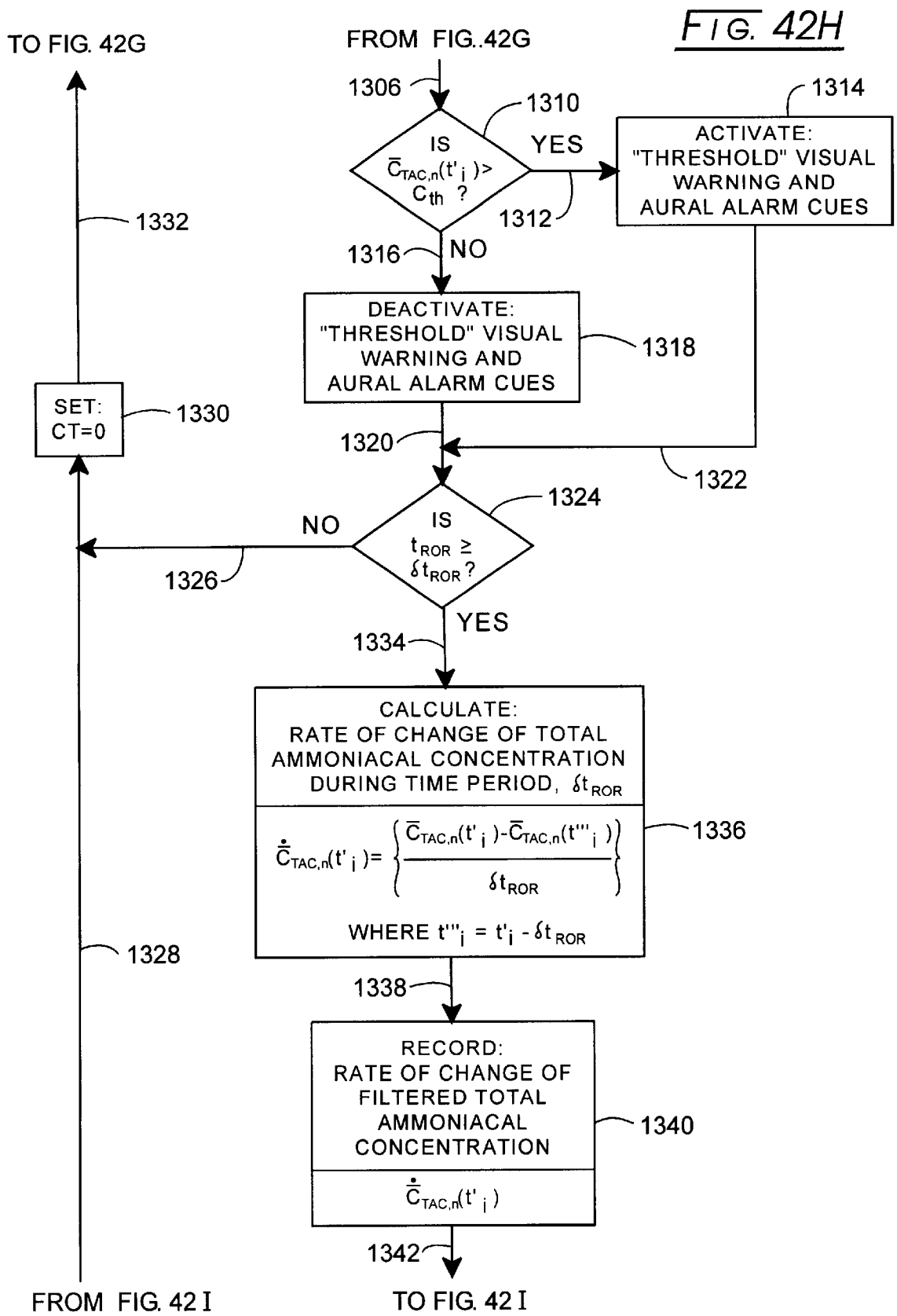
Figure 42I:
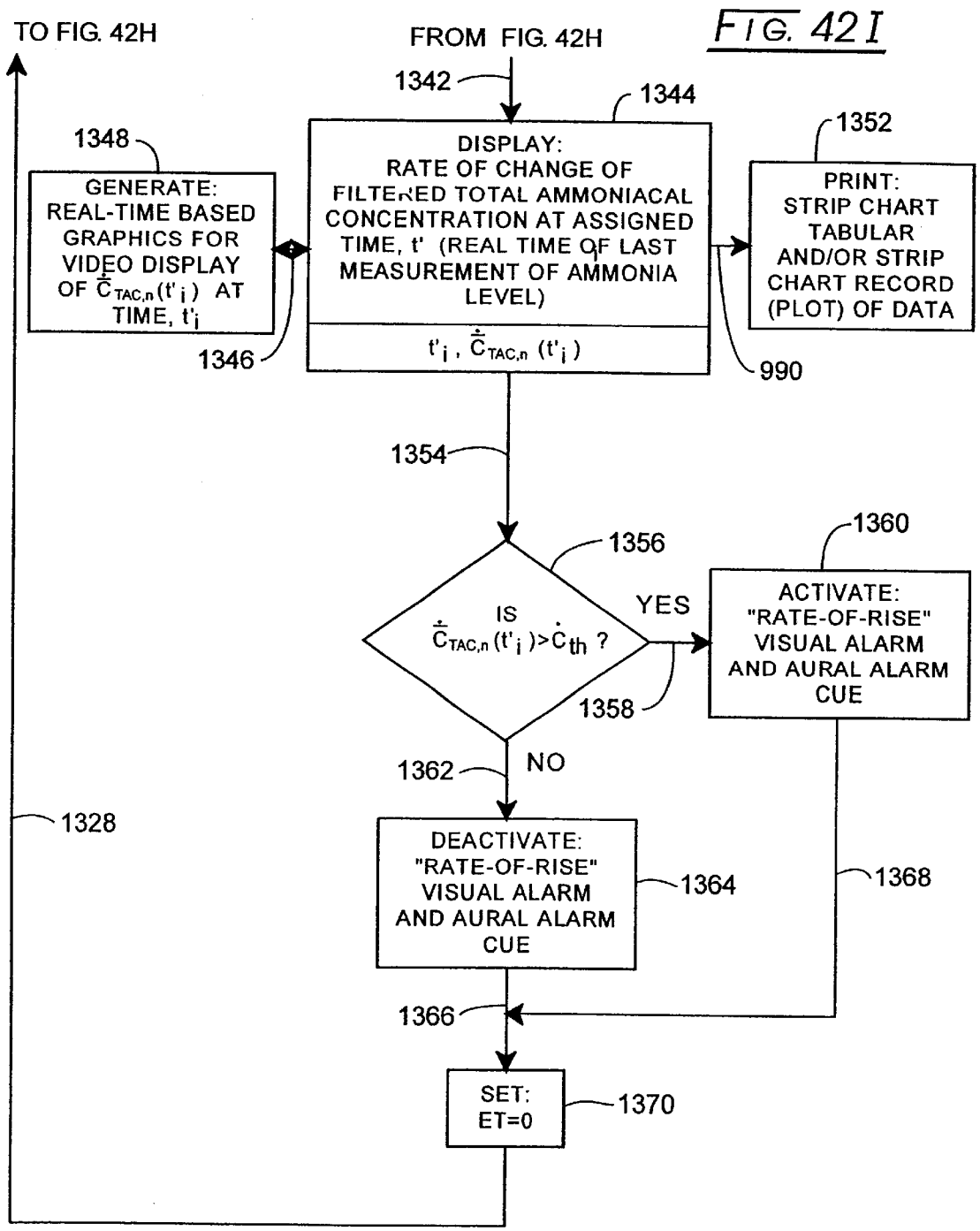

Refering to FIGS. 42B and 42C, and revisiting the inquiries represented at blocks 1112 and 1122, where the relative time elapsed between CO measurements has not equaled the preestablished time interval between CO measurements, MICO and wherein the corresponding relative time lapsed between TCBV measurements has not equaled the preestablished time interval between total circulating blood volume measurements, MITCBV, then as represented at arrow 1130, the program commences the filtering, display and threshold testing of total ammoniacal concentration in blood (TAC), the value of which was calculated in connection with block 1104. Arrow 1130 extends to FIG. 42G and the test posed at block 1266. That test represents a gate keeping function wherein a determination is made as to whether the index, i, is greater than or equal to the number of components, n, elected for the moving average filtering function. Where the value of n is not reached, then as represented at arrows 1268, 1218 and block 1220, the index, i is incremented by one and, as represented at arrows 1222 and 1094, the program returns to commence measuring blood pH again, as set forth at block 1096. In the event that the index counter indicates that a number, n, of measurements has been obtained, then as represented by arrow 1270, the computations represented at block 1272 are carried out. In this regard, the moving average filtering approach utilizes, n, total ammoniacal concentration values to derive an average value. In carrying out this filtering, each TAC measurement is entered into a queue from which the oldest TAC value then is dropped. Additionally, the time assigned for a TAC value which is published at the display is the time $t'_i$ of the most recent measurement which is entered into the queue. The value which is published or displayed is represented as: $\overline{C}_{TAC,n}(t'_i)$. This filtering feature may be expressed as follows:

$$\overline{C}_{TAC,n}(t'_i) = \frac{1}{n} \sum_{m=i-n+1}^{m=i} (C_{TAC}(t'_m)) \quad (13)$$

As represented at 1274 and block 1276 the filtered total ammoniacal concentration is recorded in memory and the program moves, as represented at arrow 278 to the query posed at block 1280 determining whether the elapsed time from the start of each displayable measurement is greater than ΔT, which is the display update interval for TAC. In the event that it is not equal to or greater than that value, then as represented at arrow 1218, the program loops to block 1220 providing for the incrementing of the index, i, by one and, thereafter the program continues as represented at arrow 1222 to arrow 1094 for the commencement of measurement of blood pH at block 1096. Where the time interval for display is at hand, then as represented at arrow 1282 and block 1284, the filtered or averaged total ammoniacal concentration in blood and the pH measurement most recently taken are displayed at a real time, $t'_i$. As a correlative to this display of the numerical values, the system generates a real time graphics output displaying a time versus TAC value curve, as well as an associated TAC level threshold. Additionally, a real-time based graphic display is provided for pH. This arrangement is represented at arrow 1286 and block 1288. Correspondingly, a printed document or strip may be generated as represented by arrow 1290 and block 1292. Next, as represented at arrow 1294 and block 1296, a determination is made as to whether the computed and filtered total ammoniacal concentration assigned for the time, $t'_i$ has a value greater than the corresponding filtered TAC value at the next previous measurement time, $t''_i$. Where the contemporaneous value is greater, then a rise in filtered TAC is at hand and, as represented at arrow 1298 and block 1300, a visual warning cue is activated. This warning cue may be provided as an illumination of an amber or yellow spectrum colored LED and is described in connection with block 920 above. In the event of a negative determination with respect to the query posed at block 1296, then as represented at arrow 1302 and block 1304, any preexisting visual warning is deactivated and the program continues as represented at arrow 1306. Correspondingly, where the warning cue is activated as represented at block 1300, the program continues to arrow 1306 as represented at arrow 1308. Arrow 1306 is seen to extend to block 1310 wherein a determination is made as to whether the filtered value for total ammoniacal concentration in blood as currently measured $\overline{C}_{TAC,n}(t'_i)$ is greater than an inputted threshold value, $C_{th}$. In the event that the threshold value is exceeded, then as represented at arrow 1312 and block 1314 both visual and aural cues are activated to alert the practitioner. In the event that the threshold is not exceeded, then as represented at arrow 1316 and block 1318, any visual warning and aural alarm cues are deactivated. The program then continues as represented at arrow 1320. Where a warning activation has been developed as represented at block 1314, the program continues to arrow 1320 as represented by arrow 1322. Arrow 1320 leads to the query posed at block 1324 determining whether the time elapsed from the start time, $t_{ROR}$ is greater than or equal to the time interval utilized for carrying out a rate-of-rise calculation with respect to TAC. In the event that the elapsed time has not reached that value, then the program proceeds as represented at arrows 1326, 1328 and block 1330. At block 1330, the cumulative time clock CT is set to zero. In effect, this occurs each time filtered TAC concentration value is displayed and/or printed. The program then loops as represented at arrows 1332 and 1094.

In the event of an affirmative response to the query posed at block 1324, then the time interval for calculating rate-of-rise of filtered TAC is at hand and, as represented at arrow 1334 and block 1336, the rate-of-change of filtered total ammoniacal concentration during the period $\delta t_{ROR}$ is computed, the resulting value being identified as: $\dot{\overline{C}}_{TAC,n}(t'_i)$. As represented at arrow 1338 and block 1340, the program then records the rate-of-change of filtered total ammoniacal concentration in memory and continues as represented at arrow 1342. Arrow 1342 leads to the display operation represented at block 1344. In this regard, the rate-of-change of filtered total ammoniacal concentration is assigned a real time, $t'_i$ for the time of the last measurement of ammonia level and that value is numerically displayed and may be incorporated graphically in the display program, for example, as a bar chart or the like. The latter approach is represented by dual arrow 1346 and block 1348. Correspondingly, as represented at arrow 1350 and block 1352, a printout is provided showing this rate valuation. The program then continues as represented at arrow 1354 and block 1356 where a query is posed as to whether the computed rate-of-change of filtered total ammoniacal content is greater than the practitioner inputted rate-of-rise threshold, $\dot{C}_{th}$. In the event that the threshold is exceeded, then as represented at arrow 1358 and block 1360, visual and aural alarm cues are activated. Preferably, an LED in the red spectrum is illuminated and a warning sound is provided. Where the inquiry as posed at block 1356 indicates that no rate-of-rise threshold has been exceeded, then as represented at arrow 1362 and block 1364, any rate-of-rise warning is deactivated and the program continues as represented at arrow 1366. Where the rate-of-rise alarms have been activated as represented at block 1360, the program continues to the former arrow 1366 as represented at arrow 1368. Arrow 1366 leads to the instructions at block 1370 wherein the elapsed time, ET, or elapsed time between the displays of rate-of-change of filtered TAC is set to zero. The program then loops as represented at arrow 1328, block 1330 and arrow 1332 to arrow 1094.

Rate-of-change determination and a testing thereof also may be carried out using compacted values of CO and TCBV. In providing such rate data, procedures emulating those described in conjunction with blocks 1324 through 1352 may be employed. That rate data may be compared against rate threshold rising procedures emulating blocks 1356 through 1362 and arro2 1366.

Since certain changes may be made in the above system and method without departing from the scope of the invention herein involved, it is intended that all matter contained in the above-description or shown in the accompanying drawings shall be interpreted as illustrative and not in a limiting sense.

What is claimed is:

1. A system for determining hemodynamic parameters of a cardiovascular system said cardiovascular system circulating blood within a bloodstream extending to peripheral regions of a body comprising:

a source of analyte-containing fluid biocompatible with and metabolizable within said body and said fluid having a predetermined analyte concentration;

fluid flow control apparatus coupled with said source of analyte containing fluid and controllable to provide a flow of said analyte containing fluid at a predetermined mass flow rate at an outlet for an infusion interval having a time of delivery;

a delivery assembly having a delivery channel with an input coupled in fluid flow communication with said fluid flow control apparatus and an output positioned to express said flow of analyte-containing fluid within said bloodstream for dilutional movement therewith;

an analyte concentration sensor positioned within said bloodstream, responsive to analyte within said bloodstream and controllable to provide sensor outputs corresponding with the sensed concentration of said analyte; and a controller coupled in controlling relationship with said fluid flow control apparatus and said analyte concentration sensor, responsive to control said analyte concentration sensor to provide said sensor outputs and to derive corresponding analyte concentration values, responsive to control said fluid flow control apparatus to effect provision of said flow of said analyte-containing fluid at said outlet for said infusion interval, responsive to a sequence of said analyte concentration values, as time associated analyte concentration values, said sequence exhibiting time associated concentration values rising in value toward a peak value and descending in value therefrom, responsive to correlate said time associated concentration values, said predetermined mass flow rate, said predetermined analyte concentration and said infusion interval to derive an output signal representing a value corresponding with a select said hemodynamic parameter; and a readout responsive to said output signal for providing a perceptible output corresponding therewith.

2. The system of claim 1 in which said controller is responsive to control said analyte concentration sensor prior to said provision of said flow of analyte-containing fluid to provide said sensor outputs and derive a corresponding baseline value for concentration of said analyte, and is responsive to correlate said baseline value for concentration of said analyte with said time associated concentration values, said predetermined mass flow-rate said predetermined analyte concentration and said infusion interval to derive said output signal.

3. The system of claim 2 in which:

said select hemodynamic parameter is cardiac output; and said controller is responsive to correlate said baseline value for concentration of said analyte, said predetermined mass flow rate, said predetermined analyte concentration and said peak value of said time associated concentration values to derive said output signal as corresponding with cardiac output.

4. The system of claim 2 in which said controller is responsive to a sequence of said baseline analyte concentration level outputs to derive a comparison analyte concentration level in blood corresponding with metabolic homeostasis of said body, and responsive to compare an inputted homeostasis threshold value corresponding with analyte concentration in blood for iatrogenesis with said comparison analyte concentration level in blood to derive a second output signal when said comparison analyte concentration level in blood represents a value greater than said inputted homeostasis threshold value.

5. The system of claim 1 in which said source of analyte-containing fluid is selected from the group consisting of: ammoniacal fluid, heparin, ethanol, glucose and anesthesia agent.

6. The system of claim 1 in which:

said controller includes a real time clock providing a real time output;

said controller is responsive to said real time output with the contemporaneous derived occurrence of a said output signal to derive a time associated display signal; and said readout is responsive to said time associated display signal to provide a visually perceptible display of the derived value of said select hemodynamic parameter and the time of its derivation.

7. The system of claim 6 in which:

said readout is responsive to each of a sequence of said time associated display signals to produce a trend defining graphics display thereof.

8. The system of claim 1 in which said analyte concentration sensor comprises:

an analyte concentration reactor having an output condition in response to the concentration of said analyte;

a support and transmission assembly for conveying said sensor outputs corresponding with said output condition to said controller; and a membrane mounted upon said support and transmission assembly, permeable to said analyte, having an outer surface contactable with said blood and positioned to communicate said analyte with said reactor.

9. The system of claim 8 in which:

said analyte-containing fluid is ammoniacal fluid;

said membrane is permeable to ammonium ion ($NH_4^+$);

said reactor comprises first and second electrodes immersed within an electrolyte sensitive to said ammonium ion; and said controller controls said analyte concentration sensor to derive said sensor outputs as amperometric outputs.

10. The system of claim 8 in which:

said analyte-containing fluid is ammoniacal fluid;

said membrane is permeable to ammonium ion ($NH_4^+$);

said reactor comprises first and second electrodes immersed within an electrolyte sensitive to said ammonium ion; and said controller controls said analyte concentration sensor to derive said sensor output as potentiometric signals.

11. The system of claim 8 in which:

said analyte concentration reactor comprises an analyte-sensitive fluorescent material having a fluorescence intensity as said output condition;

said support and transmission assembly comprises a fiberoptic assembly; and said controller controls said analyte concentration sensor by stimulating said fluorescent material through said fiberoptic assembly and deriving said sensor outputs as fluorescence intensity conveyed by said fiberoptic assembly.

12. The system of claim 8 in which:

said analyte concentration reactor comprises an analyte-sensitive fluorescent material stimulatable into fluorescence, the rate of quenching of said fluorescence being said output condition;

said support and transmission assembly comprises a fiberoptic assembly; and said controller controls said analyte concentration sensor by stimulating said fluorescent material through said fiberoptic assembly and deriving said sensor outputs as said rate of quenching conveyed by said fiberoptic assembly.

13. The system of claim 8 in which:

said analyte concentration reactor comprises a Schottky diode array having a conductive polymer responsive to said analyte to effect a forward bias alteration as said output condition.

14. The system of claim 8 in which:

said analyte-containing fluid is ammoniacal fluid;

said membrane is permeable to gaseous ammonia ($NH_3$);

said reactor is a gaseous ammonia sensitive dye;

said support and transmission assembly is a fiberoptic colorimetric measurement assembly which quantitates a change in color of the dye to provide said sensor outputs; and said controller is responsive to said sensor outputs and the pH exhibited by said blood to derive said analyte concentration values.

15. The system of claim 14 in which:

said controller derives a said analyte concentration value as total ammoniacal concentration in blood in correspondence with the expressions:

$$Ca(NH_4^+) = Ca(NH_3)/[10\exp(pH-pKa)]$$

$$Ca = Ca(NH_3) + Ca(NH_4^+)$$

where: $Ca(NH_4^+)$ is the concentration of ammonium ions in blood, $Ca(NH_3)$ is the measured concentration of ammonia gas in blood, pH is measured blood pH, pKa is the pH level of solution above which ammoniacal fluid exists only as a gas, and Ca is the total ammoniacal concentration in blood.

16. The system of claim 14 including:

a pH sensor configured for positioning within said bloodstream at a said peripheral region and controllable to provide a pH sensor output corresponding with the pH value of blood with which it is in contact; and said controller effects control of said pH sensor to derive said pH sensor output and said pH exhibited by said blood corresponding therewith.

17. The system of claim 1 in which said analyte concentration sensor comprises an acoustic-wave sensor having an acoustic-wave delay line within an oscillator loop to derive said sensor outputs.

18. The system of claim 1 in which:

said analyte concentration sensor comprises:

a fiberoptic assembly extending from a proximal region to a tip;

a membrane permeable to said analyte, having an outer surface within said bloodstream and an inner surface spaced from said fiberoptic tip to define an analyte equilibration cavity; and said controller includes a light transmission and reception assembly optically coupled with said fiberoptic assembly proximal region and actuable to derive said sensor outputs with respect to analyte at said equilibration cavity.

19. The system of claim 1 in which:

said analyte concentration sensor comprises:

a fiberoptic assembly extending from a proximal region to a tip, including an outer surface extending inwardly from said tip;

an end plug impervious to blood having an inwardly disposed surface spaced from said tip to define the length of an equilibration cavity;

a membrane permeable to said analyte, having an outer surface contactable with said bloodstream and extending sealingly about said outer surface and said end plug to define the rider of said equilibration cavity; and said controller includes a light transmission and reception assembly optically coupled with said fiberoptic assembly proximal region and actuable to derive said sensor output with respect to analyte at said equilibration cavity.

20. The system of claim 1 in which:

said analyte concentration sensor comprises:

a fiberoptic assembly extending from a proximal region to a forward region located within said bloodstream, said forward region having a forward light transmission leg and a return transmission leg spaced from said forward transmission leg to define a gap; and a membrane permeable to said analyte having an outer surface exposable to said blood in said bloodstream; said membrane sealingly extending about said gap to define an equilibration cavity; and said controller includes a light transmission assembly optically coupled with said fiberoptic assembly forward light transmission leg at said proximal region and including a light reception assembly optically coupled with said fiberoptic assembly return transmission leg at said proximal region and actuable to derive said sensor outputs with respect to analyte at said equilibration cavity.

21. The system of claim 1 in which: said analyte concentration sensor comprises a fiberoptic support and transmission assembly extending from a proximal region from which said sensor outputs are transmissible, to a distal end face;

a porous reactor support configured with a matrix of receptor pores and having a support thickness defined between a forward surface and a support rearward region;

an analyte concentration reactor confined within said matrix of receptor pores and having an output condition in response tot he concentration of said analyte;

a non-porous, optically transparent backer component having a forward region bonded with said support rearward region substantially non-invasive with said receptor pores and having an oppositely disposed backer rearward region spaced from said forward region a backer thickness and coupled with said fiberoptic support and transmission assembly distal end face with an optically transparent adhesive.

22. The system of claim 21 in which:

said reactor is an analyte-sensitive dye; and said fiberoptic support and transmission assembly is configured to quantitate said output condition by the transmission to and reception from said reactor of light of predetermined wavelength.

23. The system of claim 1 in which:

said analyte-containing fluid is ammoniacal fluid;

said reactor is an ammonia sensitive dye;

said fiberoptic support and transmission assembly is configured for colorimetric evaluation of changes in color of said dye to derive said sensor outputs; and said controller is responsive to said sensor outputs and the pH exhibited by said blood to derive said analyte concentration values.

24. The system of claim 23 in which:

said controller derives a said analyte concentration value as total ammoniacal concentration in blood in correspondence with the expressions:

$$Ca(NH_4^+) = Ca(NH_3)/[10\exp(pH-pKa)]$$

$$Ca = Ca(NH_3) + Ca(NH_4^+)$$

where: $Ca(NH_4^+)$ is the concentration of ammonium ions in blood, $Ca(NH_3)$ is the measured concentration of ammonia gas in blood, pH is measured blood pH, pKa is the pH level of solution above which ammoniacal fluid exists only as a gas, and Ca is the total ammoniacal concentration in blood.

25. The system of claim 21 in which:

said backer component backer thickness is in a range of about one to four mils.

26. The system of claim 21 in which:

said reactor support thickness is in a range of about one to four mils.

27. The system of claim 1 in which:

said analyte concentration sensor is mounted within a catheter configured for indwelling positioning within the heart.

28. The system of claim 1 in which:

said analyte concentration sensor is mounted within a pulmonary artery catheter at a location effective for positioning in adjacency with the pulmonary valve of the heart of said body.

29. The system of 28 in which:

said delivery assembly is mounted within said pulmonary artery catheter.

30. The system of claim 1 in which:

said analyte concentration sensor comprises:

a rigid thin tube extending from a base region to a tip configured for positioning within said bloodstream and having an open, internal channel extending from said base region through said tip;

a fiberoptic assembly from which said sensor outputs are transmissible slideably positioned within said chamber and having an end face moveable from a retracted position outwardly from said tip;

a reactor support mounted upon said end face;

an analyte concentration reactor retained by said reactor support, having an output condition in response to the concentration of said analyte; and said controller includes a light transmission and reception assembly optically coupled with said fiberoptic assembly which is actuable to derive said sensor output by the application of light of predetermined wavelength to said reactor.

31. The system of claim 30 in which:

said reactor support is a porous polymeric optically transparent component having a matrix of receptor pores; and said analyte concentration reactor is confined within said matrix of receptor pores.

32. The system of claim 31 in which said analyte concentration sensor includes a non-porous, optically transparent backer component having a forward region non-adhesively bonded to said reactor support and an oppositely disposed rearward region adhesively bonded to said fiberoptic assembly end face.

33. The method for determining hemodynamic parameter of a cardiovascular system wherein blood within a bloodstream is circulated to peripheral regions of the body, comprising the steps of:

(a) providing a source of analyte-containing fluid biocompatible with and metabolizable within said body and having a predetermined analyte concentration;

(b) providing fluid flow control apparatus having an input coupled in fluid flow communication with said source of analyte-containing fluid and actuable to provide a flow of said analyte-containing fluid at a mass flow rate at an outlet for an infusion interval;

(c) providing an analyte concentration sensor having a distal analyte responsive portion and a communication channel extending therefrom to a proximal region, and being controllable from said proximal region to provide sensor outputs corresponding with the sensed concentration of said analyte;

(d) providing a delivery assembly having a delivery channel with an input coupled in fluid flow communication with said fluid flow and an output positionable within said bloodstream through which said analyte containing fluid is expressible at said mass flow rate;

(e) providing a controller operatively responsive with said fluid flow control apparatus and coupled in controlling relationship with said analyte concentration sensor, and actuable to record the time of delivery of said analyte-containing fluid at the commencement of said infusion interval, responsive thereafter to control said analyte concentration sensor to effect provision of timed sequence of said sensor outputs and derive a corresponding sequence of time associated analyte concentration values, said time associated sequence of analyte concentration values rising in value toward a peak value and decreasing in value therefrom, responsive to correlate said time associated sequence of analyte concentration values, said mass flow rate and said time of delivery to derive an output signal representing a value corresponding with a select hemodynamic parameter;

(f) positioning said analyte concentration sensor distal analyte responsive portion and said delivery assembly output within said bloodstream at a said peripheral region:

(g) actuating said controller to derive said output signal; and (h) providing a readout responsive to said output signal and having a perceptible output identifying the value of the hemodynamic parameter corresponding therewith.

34. The method for determining the total circulating blood volume of a cardiovascular system circulating blood within a bloodstream extending to a peripheral region of a body and exhibiting a pH value, comprising the steps of:

(a) providing a source of analyte-containing fluid biocompatible with and metabolizable within said body and having a predetermined analyte concentration;

(b) providing an analyte concentration sensor having a distal analyte responsive portion configured for positioning within said bloodstream and responsive to the presence of said analyte to provide sensor outputs corresponding with the sensed concentration of analyte;

(c) providing a delivery assembly having a delivery channel with an input coupled in fluid flow communication with said source of analyte containing fluid and an output configured for positioning within said bloodstream;

(d) positioning said analyte concentration sensor distal analyte responsive portion and said delivery assembly output within said bloodstream;

(e) delivering said analyte-containing fluid from said source into said delivery channel at a time of delivery, and at a dose value defining mass flow rate, at said predetermined analyte concentration, and over an infusion interval;

(f) deriving a sequence of time associated analyte concentration values from said sensor outputs;

(g) monitoring said sequence of time associated concentration values and identifying a sequence thereof descending in value from a peak-defining inflection value; and (h) deriving a value for total circulating blood volume by correlating said time of delivery, said dose value and identified sequence of time associated concentration values descending in value.

35. The method of claim 34 in which:

said step (d) includes the step of (d1) prior to said step (e) deriving a baseline value corresponding with the concentration of said analyte in said body from said analyte concentration sensor outputs; and said step (h) further correlates said baseline value to derive said value for total circulating blood volume.

36. The method of claim 35 including the step:

(i) deriving a value for cardiac output by correlating said baseline value for concentration of said analyte, said mass flow rate, said predetermined analyte concentration and said identified peak-defining inflection value.

37. The method of claim 35 in which:

said step (g) further identifies a sequence of said time associated concentration values rising in value towards said peak-defining inflection value; and including the step:

(i) deriving a value for cardiac output by correlating said baseline value for concentration of said analyte, said mass flow rate, said predetermined analyte concentration, said infusion interval and an integrated value of said time associated concentration values.

38. The method of claim 34 in which said step (f) derivation of time associated concentration values is carried out in conjunction with a sensor output frequency of about one measurement per second.

39. The method of claim 34 in which said analyte-containing fluid source is selected from the group consisting of: ammoniacal fluid, heparin, ethanol, glucose and anesthesia agent and excluding oxygen and carbon dioxide releasing fluid.

40. The method of claim 34 which said step (d) is carried out by positioning said analyte concentration sensor distal analyte responsive portion and said delivery assembly output within said bloodstream said peripheral region.

41. The method of claim 40 including the step:

(i) deriving a value for cardiac output in correspondence with the expression:

$$CO(t_i) = \frac{K * m_l * [IC_a - C_a(t_i')]}{[C_a(t_i') - C_a(t_i)]}$$

where: $CO(t_i)$ is cardiac output measured at time ($t_i$), K is a constant, $m_l$ is the fluid mass flow rate of ammoniacal fluid, ICa is total ammoniacal concentration of the analyte-containing fluid, $C_a(t_i')$ is the total ammoniacal concentration in blood based upon said peak defining inflection value, and $C_a(t_i)$ is the total ammoniacal concentration in blood based upon said baseline value.

42. The method of claim 34 in which said step (h) correlates said time of delivery and said identified time associated concentration values descending in value to derive a maximum increase value for said analyte within said bloodstream and correlates said maximum increase value with said dose value to derive said total circulating blood volume.

43. The method of claim 42 in which said maximum increase value is derived by regression analysis of said time associated sensor outputs descending in value with respect to said time of delivery.

44. The method of claim 43 in which said time of delivery is the mean of the time interval of occurrence of said infusion interval.

45. The method of claim 34 in which:

said analyte-containing fluid is an ammoniacal fluid; and said step (f) is carried out by correlating said pH value and said sensor outputs.

46. The method of claim 34 including the steps of:

(i) selecting a homostasis threshold value corresponding with an analyte concentration level in blood for iatrogenesis;

(j) determining a baseline of analyte concentration in said bloodstream corresponding with metabolic homeostasis of said body; and (k) determining whether said concentration of analyte determined at step (j) exceeds the threshold value at step (i).

47. The method of claim 34 in which:

said analyte-containing fluid is an ammoniacal fluid;

said step (b) provides said analyte concentration sensor distal analyte portion as being responsive to provide said sensor outputs in correspondence with the concentration of ammonia gas ($NH_3$) in said bloodstream;

said step (f) derives said time associated concentration values as representing the total ammoniacal concentration in blood in correspondence with the expressions:

$$Ca(NH_4^+) = Ca(NH_3)/[10\exp(pH-pKa)]$$

$$Ca = Ca(NH_3) + Ca(NH_4^+)$$

where: $Ca(NH_4^+)$ is the concentration of ammonium ions in blood, $Ca(NH_3)$ is the measured concentration of ammonia gas in blood, pH is said blood pH value, pKa is the pH level of solution above which ammoniacal fluid exists only as a gas, and Ca is the total ammoniacal concentration in blood.

48. The method of claim 34 in which:

said steps (d) includes the step of:

(d1) prior to said step (e) deriving a baseline value corresponding with the concentration of said analyte in said body from said analyte concentration sensor outputs;

said analyte-containing fluid is an ammoniacal fluid;

said step (b) provides said analyte concentration sensor distal analyte portion as being responsive to provide said sensor outputs in correspondence with the concentration of ammonia gas ($NH_3$) in said bloodstream;

said step (d1) derives said baseline value as representing the total ammoniacal concentration in blood in correspondence with the expressions:

$$Ca(NH_4^+) = Ca(NH_3)/[10\exp(pH-pKa)]$$

$$Ca = Ca(NH_3) + Ca(NH_4^+)$$

where: $Ca(NH_4^+)$ is the concentration of ammonium ions in blood, $Ca(NH_3)$ is the measured concentration of ammonia gas in blood, pH is measured blood pH, pKa is the pH level of solution above which ammoniacal fluid exists only as a gas, and Ca is the total ammoniacal concentration in blood.

49. The method of claim 48 in which:

said step (f) derives said time associated concentration values as representing the total ammoniacal concentration in blood in correspondence with the expressions:

$$Ca(NH_4^+)=Ca(NH_3)/[10exp(pH-pKa)]$$

$$Ca=Ca(NH_3)+Ca(NH_4^+)$$

where: $Ca(NH_{4+})$ is the concentration of ammonium ions in blood, $Ca(NH_3)$ is the measured concentration of ammonia gas in blood, pH is measured blood pH, pKa is the pH level of solution above which ammoniacal fluid exists only as a gas, and Ca is the total ammoniacal concentration in blood.

50. The method of claim 47 in which:

(i) deriving a value for cardiac output by correlating said baseline value for concentration of said analyte, said mass flow rate, said predetermined analyte concentration and said identified peak-defining inflection value.

51. The method of claim 49 in which:

said step (g) further identifies a sequence of said time associated concentration values rising in value towards said peak-defining inflection value; and including the step:

(i) deriving a value for cardiac output by correlating said baseline value for concentration of said analyte, said mass flow rate, said predetermined analyte concentration, said infusion interval and an integrated value of said time associated concentration values.

52. The method of claim 34 in which:

said analyte-containing fluid is an ammoniacal fluid;

said step (b) includes the step: (b1) providing a pH sensor having a distal pH responsive portion configured for positioning within said bloodstream and having a pH sensor output corresponding with the pH value of blood with which it is in contact;

said step (d) includes the step: (d1) positioning said distal pH responsive portion within said bloodstream; and said step (f) is carried out by correlating said pH value and said sensor outputs.

53. The method of claim 52 in which said pH sensor and said analyte concentration sensor are provided being incorporated within a single catheter assembly insertable within said bloodstream.

54. The method of claim 34 in which:

said step (b) provision of an analyte concentration sensor incorporates said distal analyte responsive portion within a pulmonary artery catheter; and said step (c) provision of a delivery assembly incorporates said delivery channel and said output within said pulmonary artery catheter.

55. The method of claim 54 in which said distal analyte responsive portion is provided at a location upon said catheter so as to be located in adjacency with the pulmonary valve of the heart of said body.

56. The method for determining hemodynamic parameters of a cardiovascular system wherein blood within a bloodstream is circulated to peripheral regions of the body and exhibits a pH value, comprising the steps of:

(a) providing a source of analyte-containing fluid biocompatible with and metabolizable within said body and having a predetermined analyte concentration;

(b) providing an analyte concentration sensor having a distal analyte responsive portion configured for positioning within said bloodstream and responsive to the presence of analyte to provide sensor outputs corresponding with the sensed concentration of analyte;

(c) providing a delivery assembly having a delivery channel with an input coupled in fluid flow communication with said source of analyte-containing fluid and an output configured for positioning within the bloodstream;

(d) positioning said analyte concentration sensor distal analyte responsive portion and said delivery assembly output within said bloodstream;

(e) delivering said analyte-containing fluid from said source into said delivery channel at a time of delivery, a mass flow rate and over an infusion interval;

(f) deriving a sequence of time associated analyte concentration values from said sensor outputs;

(g) monitoring said sequence of time associated analyte concentration values and identifying a sequence thereof rising in value to a peak defining inflection value and descending in value therefrom; and (h) deriving a value for a select one of said hemodynamic parameters by correlating said sequence of time associated concentration values, said mass flow rate, said infusion interval and said predetermined analyte concentration.

57. The method of claim 56 in which:

said step (d) includes the step of:

(d1) prior to said step (e) deriving from said analyte concentration sensor outputs a baseline value corresponding with the concentration of said analyte in said bloodstream; and said step (h) further correlates said baseline value to derive said select one of said hemodynamic parameters.

58. The method of claim 56 in which:

said step (f) derivation of time associated concentration values is carried out in conjunction with a sensor output frequency of about one measurement per second.

59. The method of claim 56 in which said analyte-containing fluid source is selected from the group consisting of: ammoniacal fluid, heparin, ethanol, glucose and anesthesia agent.

60. The method of claim 56 in which (i) selecting a homostasis threshold value corresponding with an analyte concentration level in blood for iatrogenesis;

(i) determining a baseline of analyte concentration in said bloodstream corresponding with metabolic homeostasis of said body; and (k) determining whether said concentration of analyte determined at step (j) exceeds the threshold value at step (i).

61. The method of claim 56 in which:

said analyte-containing fluid is an ammoniacal fluid;

said step (b) provides said analyte concentration sensor distal analyte portion as being responsive to provide said sensor outputs in correspondence with the concentration of ammonia gas ($NH_3$) in said bloodstream;

said step (f) derives said time associated concentration values as representing the total ammoniacal concentration in blood in correspondence with the expression:

$$Ca(NH_4^+)=Ca(NH_3)/[10exp(pH-pKa)]$$

$$Ca=Ca(NH_3)+Ca(NH_4^+)$$

where: $Ca(NH_4^+)$ is the concentration of ammonium ions in blood, $Ca(NH_3)$ is the measured concentration of ammonia gas in blood, pH is measured blood pH, pKa is the pH level of solution above which ammoniacal fluid exists only as a gas, and Ca is the total ammoniacal concentration in blood.

62. The method of claim 56 in which:

said step (d) includes the step of:

(d1) prior to said step (e) deriving a baseline value corresponding with the concentration of said analyte in said body from said analyte concentration sensor outputs;

said analyte-containing fluid is an ammoniacal fluid;

said step (b) provides said analyte concentration sensor distal analyte portion as being responsive to provide said sensor outputs in correspondence with the concentration of ammonia gas ($NH_3$) in said bloodstream;

said step (d1) derives said baseline value as representing the total ammoniacal concentration in blood in correspondence with the expressions:

$$Ca(NH_4^+) = Ca(NH_3)/[10\exp(pH-pKa)]$$

$$Ca = Ca(NH_3) + Ca(NH_4^+)$$

where: $Ca(NH_4^+)$ is the concentration of ammonium ions in blood, $Ca(NH_3)$ is the measured concentration of ammonia gas in blood, pH is measured blood pH, pKa is the pH level of solution above which ammoniacal fluid exists only as a gas, and Ca is the total ammoniacal concentration in blood.

63. The method of claim 62 in which:

said step (f) derives said time associated concentration values as representing the total ammoniacal concentration in blood in correspondence with the expressions:

$$Ca(NH_4^+) = Ca(NH_3)/[10\exp(pH-pKa)]$$

$$Ca = Ca(NH_3) + Ca(NH_4^+)$$

where: $Ca(NH_4^+)$ is the concentration of ammonium ions in blood, $Ca(NH_3)$ is the measured concentration of ammonia gas in blood, pH is measured blood pH, pKa is the pH level of solution above which ammoniacal fluid exists only as a gas, and Ca is the total ammoniacal concentration in blood.

64. The method of claim 56 in which:

said analyte-containing fluid is an ammoniacal fluid;

said step (b) includes the step: (b1) providing a pH sensor having a distal pH responsive portion configured for positioning within said bloodstream and having a pH sensor output corresponding with the pH value of blood with which it is in contact;

said step (d) includes the step: (d1) positioning said distal pH responsive portion within said bloodstream; and said step (f) is carried out by correlating said pH value and said sensor outputs.

65. The method of claim 64 in which said pH sensor and said analyte concentration sensor are provided being incorporated within a single catheter assembly insertable within said bloodstream.

66. The method of claim 56 which:

said step (b) provision of an analyte concentration sensor incorporates said distal analyte responsive portion within a pulmonary artery catheter.

67. The method of claim 66 in which said distal analyte responsive portion is provided at a location upon said catheter so as to be located in adjacency with the pulmonary valve of the heart of said body.

68. A system for determining hemodynamic parameters of a cardiovascular system said cardiovascular system circulating blood within a bloodstream extending to peripheral regions of a body comprising:

a source of analyte-containing fluid biocompatible with and metabolizable within said body and said fluid having a predetermined analyte concentration;

fluid flow control apparatus coupled with said source of analyte containing fluid and controllable to provide a flow of said analyte containing fluid at a predetermined mass flow rate at an outlet for an infusion interval having a time of delivery;

a delivery assembly having a delivery channel with an input coupled in fluid flow communication with said fluid flow control apparatus and an output positioned to express said flow of analyte-containing fluid within said bloodstream for dilutional movement therewith;

a blood by-passing assembly including:

a blood transport conduit extending from a proximal end to a distal tip, said distal tip being positionable in blood exchange relationship within said bloodstream a blood sampling chamber coupled in blood exchange communication with said blood transport conduit proximal end, and a pump coupled with said sampling chamber and controllable to urge the transport of blood from said bloodstream into said sampling chamber;

an analyte concentration sensor positioned within said blood sampling chamber, responsive to analyte within said blood and controllable to provide sensor outputs corresponding with the sensed concentration of said analyte; and a controller coupled in controlling relationship with said fluid flow control apparatus and said analyte concentration sensor, responsive to control said pump and analyte concentration sensor to provide said sensor outputs and to derive corresponding analyte concentration values, responsive to control said fluid flow control apparatus to effect provision of said flow of said analyte-containing fluid at said outlet for said infusion interval, responsive to a sequence of said analyte concentration values, as time associated analyte concentration values, said sequence exhibiting time associated concentration values rising in value toward a peak value and descending in value, therefrom, responsive to correlate said time associated concentration values, said predetermined mass flow rate, said predetermined analyte concentration and said infusion interval to derive an output signal representing a value corresponding with a select said hemodynamic parameter; and a readout responsive to said output signal for providing a perceptible output corresponding therewith.

69. The system of claim 68 in which said controller is responsive to control said pump and said analyte concentration sensor prior to said provision of said flow of analyte-containing fluid to provide said sensor outputs and derive a corresponding baseline value for concentration of said analyte, and is responsive to correlate said baseline value for concentration of said analyte with said time associated concentration values, said predetermined mass flow-rate said predetermined analyte concentration and said infusion interval to derive said output signal.

70. The system of claim 69 in which:

said select hemodynamic parameter is total circulating blood volume; and said controller is responsive to correlate said baseline value for concentration of said analyte, said predetermined mass flow rate, said infusion interval, said time of delivery and said time associated concentration values descending in value from said peak to derive said output signal as corresponding with total circulating blood volume.

71. The system of claim 69 in which:

said select hemodynamic parameter is cardiac output; and said controller is responsive to correlate said baseline value for concentration of said analyte, said predetermined mass flow rate, said predetermined analyte concentration and said peak value of said time associated concentration values to derive said output signal as corresponding with cardiac output.

72. The system of claim 69 which:

said select hemodynamic parameter is cardiac output; and said controller is responsive to correlate said baseline value for concentration of said analyte, said predetermined mass flow rate, said predetermined analyte concentration, said infusion interval, and an integrated value of said time associated concentration values to derive said output signal as corresponding with cardiac output.

73. The system of claim 68 in which:

said select hemodynamic parameter is total circulating blood volume; and said controller is responsive to correlate said predetermined analyte concentration, said predetermined mass flow rate and said infusion interval to derive a dose value, and is responsive to derive a maximum increase value for said analyte within said bloodstream by correlating said time associated concentration values descending in value with said time of delivery, and is responsive to said dose value and to said maximum increase value to derive said output signal as corresponding with total circulating blood volume.

74. The system of claim 73 in which said controller is responsive to derive said maximum increase value by regression analysis of said time associated sensor outputs descending in value.

75. The system of claim 68 in which said source of analyte-containing fluid is selected from the group consisting of: ammoniacal fluid, heparin, ethanol, glucose and anesthesia agent.

76. A system for determining hemodynamic parameters of a cardiovascular system said cardiovascular system circulating blood within a bloodstream extending to peripheral regions of a body comprising:

a source of analyte-containing fluid biocompatible with and metabolizable within said body and said fluid having a predetermined analyte concentration;

fluid flow control apparatus coupled with said source of analyte containing fluid and controllable to provide a flow of said analyte containing fluid at a predetermined mass flow rate at an outlet for an infusion interval having a time of delivery;

a delivery assembly having a delivery channel with an input coupled in fluid flow communication with said fluid flow control apparatus and an output positioned to express said flow of analyte-containing fluid within said bloodstream for dilutional movement therewith;

an analyte concentration sensor positioned within said bloodstream, responsive to analyte within said bloodstream and controllable to provide sensor outputs corresponding with the sensed concentration of said analyte;

a controller coupled in controlling relationship with said fluid flow control apparatus and said analyte concentration sensor, responsive to control said analyte concentration sensor to provide said sensor outputs and to derive corresponding analyte concentration values, responsive to control said fluid flow control apparatus to effect provision of said flow of said analyte-containing fluid at said outlet for said infusion interval, responsive to a sequence of said analyte concentration values, as time associated analyte concentration values, said sequence exhibiting time associated concentration values rising in value toward a peak value and descending in value, therefrom, responsive to correlate said time associated concentration values, said predetermined mass flow rate, said predetermined analyte concentration and said infusion interval to derive an output signal representing a value corresponding with a select said hemodynamic parameter;

said controller is responsive to control said analyte concentration sensor prior to said provision of said flow of analyte-containing fluid to provide said sensor outputs and derive a corresponding baseline value for concentration of said analyte, and is responsive to correlate said baseline value for concentration of said analyte with said time associated concentration values, said predetermined mass flow-rate, said predetermined analyte concentration and said infusion interval to derive said output signal;

said select hemodynamic parameter is cardiac output;

said controller is responsive to correlate said baseline value for concentration of said analyte, said predetermined mass flow rate said predetermined analyte concentration and said peak value of said time associated concentration values to derive said output signal as corresponding with cardiac output; and a readout responsive to said output signal for providing a perceptible output corresponding therewith.

77. A system for determining hemodynamic parameters of a cardiovascular system said cardiovascular system circulating blood within a bloodstream extending to peripheral regions of a body comprising:

a source of analyte-containing fluid biocompatible with and metabolizable within said body and said fluid having a predetermined analyte concentration;

fluid flow control apparatus coupled with said source of analyte containing fluid and controllable to provide a flow of said analyte containing fluid at a predetermined mass flow rate at an outlet for an infusion interval having a time of delivery;

a delivery assembly having a delivery channel with an input coupled in fluid flow communication with said fluid flow control apparatus and an output positioned to express said flow of analyte-containing fluid within said bloodstream for dilutional movement therewith;

an analyte concentration sensor positioned within said bloodstream, responsive to analyte within said bloodstream and controllable to provide sensor outputs corresponding with the sensed concentration of said analyte;

a controller coupled in controlling relationship with said fluid flow control apparatus and said analyte concentration sensor, responsive to control said analyte concentration sensor to provide said sensor outputs and to derive corresponding analyte concentration values, responsive to control said fluid flow control apparatus to effect provision of said flow of said analyte-containing fluid at said outlet for said infusion interval, responsive to a sequence of said analyte concentration values, as time associated analyte concentration values, said sequence exhibiting time associated concentration values rising in value toward a peak value and descending in value, therefrom, responsive to correlate said time associated concentration values, said predetermined mass flow rate, said predetermined analyte concentration and said infusion interval to derive an output signal representing a value corresponding with a select said hemodynamic parameter;

said controller is responsive to control said analyte concentration sensor prior to said provision of said flow of analyte-containing fluid to provide said sensor outputs and derive a corresponding baseline value for concentration of said analyte, and is responsive to correlate said baseline value for concentration of said analyte with said time associated concentration values, said predetermined mass flow-rate said predetermined analyte concentration and said infusion interval to derive said output signal;

said select hemodynamic parameter is cardiac output;

said controller is responsive to correlate said baseline value for concentration of said analyte, said predetermined mass flow rate, said predetermined analyte concentration, said infusion interval, and an integrated value of said time associated concentration values to derive said output signal as corresponding with cardiac output; and a readout responsive to said output signal for providing a perceptible output corresponding therewith.

78. A system for determining hemodynamic parameters of a cardiovascular system said cardiovascular system circulating blood within a bloodstream extending to peripheral regions of a body comprising:
 a source of analyte-containing fluid biocompatible with and metabolizable within said body and said fluid having a predetermined analyte concentration;
 fluid flow control apparatus coupled with said source of analyte containing fluid and controllable to provide a flow of said analyte containing fluid at a predetermined mass flow rate at an outlet for an infusion interval having a time of delivery;
 a delivery assembly having a delivery channel with an input coupled in fluid flow communication with said fluid flow control apparatus and an output positioned to express said flow of analyte-containing fluid within said bloodstream for dilutional movement therewith;
 an analyte concentration sensor positioned within said bloodstream, responsive to analyte within said bloodstream and controllable to provide sensor outputs corresponding with the sensed concentration of said analyte;
 a controller coupled in controlling relationship with said fluid flow control apparatus and said analyte concentration sensor, responsive to control said analyte concentration sensor to provide said sensor outputs and to derive corresponding analyte concentration values, responsive to control said fluid flow control apparatus to effect provision of said flow of said analyte-containing fluid at said outlet for said infusion interval, responsive to a sequence of said analyte concentration values, as time associated analyte concentration values, said sequence exhibiting time associated concentration values rising in value toward a peak value and descending in value, therefrom, responsive to correlate said time associated concentration values, said predetermined mass flow rate, said predetermined analyte concentration and said infusion interval to derive an output signal representing a value corresponding with a select said hemodynamic parameter;

said select hemodynamic parameter is total circulating blood volume;

said controller is responsive to correlate said predetermined analyte concentration, said predetermined mass flow rate and said infusion interval to derive a dose value, and is responsive to derive a maximum increase value for said analyte within said bloodstream by correlating said time associated concentration values descending in value with said time of delivery, and is responsive to said dose value and to said maximum increase value to derive said output signal as corresponding with total circulating blood volume; and a readout responsive to said output signal for providing a perceptible output corresponding therewith.

79. The system of claim 78 in which said controller is responsive to derive said maximum increase value by regression analysis of said time associated sensor outputs descending in value.

80. A system for determining hemodynamic parameters of a cardiovascular system said cardiovascular system circulating blood within a bloodstream extending to peripheral regions of a body comprising:
 a source of analyte-containing fluid biocompatible with and metabolizable within said body and said fluid having a predetermined analyte concentration;
 fluid flow control apparatus coupled with said source of analyte containing fluid and controllable to provide a flow of said analyte containing fluid at a predetermined mass flow rate at an outlet for an infusion interval having a time of delivery;
 a delivery assembly having a delivery channel with an input coupled in fluid flow communication with said fluid flow control apparatus and an output positioned to express said flow of analyte-containing fluid within said bloodstream for dilutional movement therewith;
 an analyte concentration sensor positioned within said bloodstream, responsive to analyte within said bloodstream and controllable to provide sensor outputs corresponding with the sensed concentration of said analyte;
 a controller coupled in controlling relationship with said fluid flow control apparatus and said analyte concentration sensor, responsive to control said analyte concentration sensor to provide said sensor outputs and to derive corresponding analyte concentration values, responsive to control said fluid flow control apparatus to effect provision of said flow of said analyte-containing fluid at said outlet for said infusion interval, responsive to a sequence of said analyte concentration values, as time associated analyte concentration values, said sequence exhibiting time associated concentration values rising in value toward a peak value and descending in value, therefrom, responsive to correlate said time associated concentration values, said predetermined mass flow rate, said predetermined analyte concentration and said infusion interval to derive an output signal representing a value corresponding with a select said hemodynamic parameter;

a readout responsive to said output signal for providing a perceptible output corresponding therewith;

said select hemodynamic parameter is total circulating blood volume;

said controller includes an inputting assembly manually controllable to provide a total circulating blood volume threshold value;

said controller is responsive to said total circulating blood volume threshold value to retain it in memory;

said controller is responsive in the presence of a given output signal corresponding with a given value for total circulating blood volume and to said memory retained total circulating blood volume threshold value to derive an alarm signal when said given value for total circulating blood volume is greater than or equal to said total circulating blood volume threshold value; and said readout is responsive to said alarm signal to provide a perceptible alarm output.

81. A system for determining hemodynamic parameters of a cardiovascular system said cardiovascular system circulating blood within a bloodstream extending to peripheral regions of a body comprising:

a source of analyte-containing fluid biocompatible with and metabolizable within said body and said fluid having a predetermined analyte concentration;

fluid flow control apparatus coupled with said source of analyte containing fluid and controllable to provide a flow of said analyte containing fluid at a predetermined mass flow rate at an outlet for an infusion interval having a time of delivery;

a delivery assembly having a delivery channel with an input coupled in fluid flow communication with said fluid flow control apparatus and an output positioned to express said flow of analyte-containing fluid within said bloodstream for dilutional movement therewith;

an analyte concentration sensor positioned within said bloodstream, responsive to analyte within said bloodstream and controllable to provide sensor outputs corresponding with the sensed concentration of said analyte;

a controller coupled in controlling relationship with said fluid flow control apparatus and said analyte concentration sensor, responsive to control said analyte concentration sensor to provide said sensor outputs and to derive corresponding analyte concentration values, responsive to control said fluid flow control apparatus to effect provision of said flow of said analyte-containing fluid at said outlet for said infusion interval, responsive to a sequence of said analyte concentration values, as time associated analyte concentration values, said sequence exhibiting time associated concentration values rising in value toward a peak value and descending in value, therefrom, responsive to correlate said time associated concentration values, said predetermined mass flow rate, said predetermined analyte concentration and said infusion interval to derive an output signal representing a value corresponding with a select said hemodynamic parameter;

a readout responsive to said output signal for providing a perceptible output corresponding therewith;

said select hemodynamic parameter is total circulating blood volume;

said controller includes an inputting assembly manually controllable to provide a total circulating blood volume threshold value;

said controller is responsive in the presence of a given output signal corresponding with a given value for total circulating blood volume and for said memory retained total circulating blood volume threshold value to derive an alarm signal when said given value for total circulating blood volume is less than or equal to said total circulating blood volume threshold value; and said readout is responsive to said alarm signal to provide a perceptible alarm output.

82. A system for determining hemodynamic parameters of a cardiovascular system said cardiovascular system circulating blood within a bloodstream extending to peripheral regions of a body comprising:

a source of analyte-containing fluid biocompatible with and metabolizable within said body and said fluid having a predetermined analyte concentration;

fluid flow control apparatus coupled with said source of analyte containing fluid and controllable to provide a flow of said analyte containing fluid at a predetermined mass flow rate at an outlet for an infusion interval having a time of delivery;

a delivery assembly having a delivery channel with an input coupled in fluid flow communication with said fluid flow control apparatus and an output positioned to express said flow of analyte-containing fluid within said bloodstream for dilutional movement therewith;

an analyte concentration sensor positioned within said bloodstream, responsive to analyte within said bloodstream and controllable to provide sensor outputs corresponding with the sensed concentration of said analyte;

a controller coupled in controlling relationship with said fluid flow control apparatus and said analyte concentration sensor, responsive to control said analyte concentration sensor to provide said sensor outputs and to derive corresponding analyte concentration values, responsive to control said fluid flow control apparatus to effect provision of said flow of said analyte-containing fluid at said outlet for said infusion interval, responsive to a sequence of said analyte concentration values, as time associated analyte concentration values, said sequence exhibiting time associated concentration values rising in value toward a peak value and descending in value, therefrom, responsive to correlate said time associated concentration values, said predetermined mass flow rate, said predetermined analyte concentration and said infusion interval to derive an output signal representing a value corresponding with a select said hemodynamic parameter;

a readout responsive to said output signal for providing a perceptible output corresponding therewith;

said select hemodynamic parameter is total circulating blood volume;

said controller includes an inputting assembly manually controllable to provide a rate of change of total circulating blood volume threshold value;

said controller is responsive to said rate of change of total circulating blood volume threshold value to retain it in memory;

said controller is responsive in the presence of a given output signal corresponding with a given value for total circulating blood volume and to a previous such value for total circulating blood volume to derive a current total circulating blood volume rate of change value, and is responsive to said rate of change of total circulating blood value threshold value and to said current total circulating blood volume rate of change value to derive an alarm signal when said current total circulating blood volume rate of change value is greater than or equal to said rate of change of total circulating blood volume threshold value; and;

said readout is responsive to said alarm signal to provide a perceptible alarm output.

83. A system for determining hemodynamic parameters of a cardiovascular system said cardiovascular system circulating blood within a bloodstream extending to peripheral regions of a body comprising:

a source of analyte-containing fluid biocompatible with and metabolizable within said body and said fluid having a predetermined analyte concentration;

fluid flow control apparatus coupled with said source of analyte containing fluid and controllable to provide a flow of said analyte containing fluid at a predetermined mass flow rate at an outlet for an infusion interval having a time of delivery;

a delivery assembly having a delivery channel with an input coupled in fluid flow communication with said fluid flow control apparatus and an output positioned to express said flow of analyte-containing fluid within said bloodstream for dilutional movement therewith;

an analyte concentration sensor positioned within said bloodstream, responsive to analyte within said bloodstream and controllable to provide sensor outputs corresponding with the sensed concentration of said analyte;

a controller coupled in controlling relationship with said fluid flow control apparatus and said analyte concentration sensor, responsive to control said analyte concentration sensor to provide said sensor outputs and to derive corresponding analyte concentration values, responsive to control said fluid flow control apparatus to effect provision of said flow of said analyte-containing fluid at said outlet for said infusion interval, responsive to a sequence of said analyte concentration values, as time associated analyte concentration values, said sequence exhibiting time associated concentration values rising in value toward a peak value and descending in value, therefrom, responsive to correlate said time associated concentration values, said predetermined mass flow rate, said predetermined analyte concentration and said infusion interval to derive an output signal representing a value corresponding with a select said hemodynamic parameter;

a readout responsive to said output signal for providing a perceptible output corresponding therewith;

said select hemodynamic parameter is total circulating blood volume;

said controller includes an inputting assembly manually controllable to provide a rate change of total circulating blood volume threshold value;

said controller is responsive to said rate of change of total circulating blood volume threshold value to retain it in memory;

said controller is responsive in the presence of a given output signal corresponding with a given value for total circulating blood volume and to a previous such value for total circulating blood volume to derive a current total circulating blood volume rate of change value, and is responsive to said rate of change of total circulating blood value threshold value and to said current total circulating blood volume rate of change value to derive an alarm signal when said current total circulating blood volume rate of change value is greater than or equal to said rate of change of total circulating blood volume threshold value; and;

said readout is responsive to said alarm signal to provide a perceptible alarm output.

84. A system for determining hemodynamic parameters of a cardiovascular system said cardiovascular system circulating blood within a bloodstream extending to peripheral regions of a body comprising:

a source of analyte-containing fluid biocompatible with and metabolizable within said body and said fluid having a predetermined analyte concentration;

fluid flow control apparatus coupled with said source of analyte containing fluid and controllable to provide a flow of said analyte containing fluid at a predetermined mass flow rate at an outlet for an infusion interval having a time of delivery;

a delivery assembly having a delivery channel with an input coupled in fluid flow communication with said fluid flow control apparatus and an output positioned to express said flow of analyte-containing fluid within said bloodstream for dilutional movement therewith;

an analyte concentration sensor positioned within said bloodstream, responsive to analyte within said bloodstream and controllable to provide sensor outputs corresponding with the sensed concentration of said analyte;

a controller coupled in controlling relationship with said fluid flow control apparatus and said analyte concentration sensor, responsive to control said analyte concentration sensor to provide said sensor outputs and to derive corresponding analyte concentration values, responsive to control said fluid flow control apparatus to effect provision of said flow of said analyte-containing fluid at said outlet for said infusion interval, responsive to a sequence of said analyte concentration values, as time associated analyte concentration values, said sequence exhibiting time associated concentration values rising in value toward a peak value and descending in value, therefrom, responsive to correlate said time associated concentration values, said predetermined mass flow rate, said predetermined analyte concentration and said infusion interval to derive an output signal representing a value corresponding with a select said hemodynamic parameter;

a readout responsive to said output signal for providing a perceptible output corresponding therewith;

said select hemodynamic parameter is total circulating blood volume;

said controller is responsive in the presence of a current output signal corresponding with a current value for total circulating blood volume and is responsive to a previous value for total circulating blood volume corresponding with a previous output signal to derive a warning signal when said previous value is greater than said current value; and said readout is responsive to said alarm signal to provide a perceptible alarm output.

85. A system for determining hemodynamic parameters of a cardiovascular system said cardiovascular system circulating blood within a bloodstream extending to peripheral regions of a body comprising:

a source of analyte-containing fluid biocompatible with and metabolizable within said body and said fluid having a predetermined analyte concentration;

fluid flow control apparatus coupled with said source of analyte containing fluid and controllable to provide a flow of said analyte containing fluid at a predetermined mass flow rate at an outlet for an infusion interval having a time of delivery;

a delivery assembly having a delivery channel with an input coupled in fluid flow communication with said fluid flow control apparatus and an output positioned to express said flow of analyte-containing fluid within said bloodstream for dilutional movement therewith;

an analyte concentration sensor positioned within said bloodstream, responsive to analyte within said bloodstream and controllable to provide sensor outputs corresponding with the sensed concentration of said analyte;

a controller coupled in controlling relationship with said fluid flow control apparatus and said analyte concentration sensor, responsive to control said analytic concentration sensor to provide said sensor outputs and to derive corresponding analyte concentration values, responsive to control said fluid flow control apparatus to effect provision of said flow of said analyte-containing fluid at said outlet for said infusion interval, responsive to a sequence of said analyte concentration values, as time associated analyte concentration values, said sequence exhibiting time associated concentration values rising in value toward a peak value and descending in value, therefrom, responsive to correlate said time associated concentration values, said predetermined mass flow rate, said predetermined analyte concentration and said infusion interval to derive an output signal representing a value corresponding with a select said hemodynamic parameter;

a readout responsive to said output signal for providing a perceptible output corresponding therewith;

said select hemodynamic parameter is total circulating blood volume;

said controller is responsive in the presence of a current output signal corresponding with a current value for total circulating blood volume and is responsive to a previous value for total circulating blood volume corresponding with a previous output signal to derive a warning signal when said previous value is less than said current value; and said readout is responsive to said alarm signal to provide a perceptible alarm output.

86. A system for determining hemodynamic parameters of a cardiovascular system said cardiovascular system circulating blood within a bloodstream extending to peripheral regions of a body comprising:

a source of analyte-containing fluid biocompatible with and metabolizable within said body and said fluid having a predetermined analyte concentration;

fluid flow control apparatus coupled with said source of analyte containing fluid and controllable to provide a flow of said analyte containing fluid at a predetermined mass flow rate at an outlet for an infusion interval having a time of delivery;

a delivery assembly having a delivery channel with an input coupled in fluid flow communication with said fluid flow control apparatus and an output positioned to express said flow of analyte-containing fluid within said bloodstream for dilutional movement therewith;

an analyte concentration sensor positioned within said bloodstream, responsive to analyte within said bloodstream and controllable to provide sensor outputs corresponding with the sensed concentration of said analyte;

a controller coupled in controlling relationship with said fluid flow control apparatus and said analyte concentration sensor, responsive to control said analyte concentration sensor to provide said sensor outputs and to derive corresponding analyte concentration values, responsive to control said fluid flow control apparatus to effect provision of said flow of said analyte-containing fluid at said outlet for said infusion interval, responsive to a sequence of said analyte concentration values, as time associated analyte concentration values, said sequence exhibiting time associated concentration values rising in value toward a peak value and descending in value, therefrom, responsive to correlate said time associated concentration values, said predetermined mass flow rate, said predetermined analyte concentration and said infusion interval to derive an output signal representing a value corresponding with a select said hemodynamic parameter;

a readout responsive to said output signal for providing a perceptible output corresponding therewith;

said system including:

a blood by-passing assembly including:

a blood transport conduit extending from a proximal end to a distal tip, said distal tip being positionable in blood exchange relationship within said bloodstream;

a blood sampling chamber coupled in blood exchange communication with said blood transport conduit proximal end, a pump coupled with said sampling chamber and actuable to urge the transport of blood from said bloodstream into said sampling chamber; and said analyte concentration sensor is positioned within said bloodstream at said blood sampling chamber and is responsive to analyte within said chamber.

87. The system of claim 86 in which said pump is actuable to return blood from said blood sampling chamber into said bloodstream.

88. The system of claim 86 in which said pump is actuable and the control of said controller.

89. The method of claim 86 in which said maximum increase value is derived by regression analysis of said time associated sensor outputs descending in value with respect to said time of delivery.

90. The method for determining hemodynamic parameters of a cardiovascular system wherein blood within a bloodstream is circulated to peripheral regions of the body and exhibits a pH value, comprising the steps of:

(a) providing a source of analyte-containing fluid biocompatible with and metabolizable within said body and having a predetermined analyte concentration;

(b) providing an analyte concentration sensor having a distal analyte responsive portion configured for positioning within said bloodstream and responsive to the presence of analyte to provide sensor outputs corresponding with the sensed concentration of analyte;

(c) providing a delivery assembly having a delivery channel with an input coupled in fluid flow communication with said source of analyte-containing fluid and an output configured for positioning within the bloodstream;

(d) positioning said analyte concentration sensor distal analyte responsive portion and said delivery assembly output within said bloodstream;

(e) delivering said analyte-containing fluid from said source into said delivery channel at a time of delivery, a mass flow rate and over an infusion interval;

(f) deriving a sequence of time associated analyte concentration values from said sensor outputs;

(g) monitoring said sequence of time associated analyte concentration values and identifying a sequence thereof rising in value to a peak defining inflection value and descending in value therefrom;

(h) deriving a value for a select one of said hemodynamic parameters by correlating said sequence of time associated concentration values, said mass flow rate, said infusion interval and said predetermined analyte concentration; and wherein said step (h) derives a value for total circulating blood volume as said select one of said hemodynamic parameters by correlating said time of delivery, said predetermined analyte concentration, said infusion interval and identified sequence of time associated concentration values descending in value from said peak defining inflection value.

91. The method for determining hemodynamic parameters of a cardiovascular system wherein blood within a bloodstream is circulated to peripheral regions of the body and exhibits a pH value, comprising the steps of:

(a) providing a source of analyte-containing fluid biocompatible with and metabolizable within said body and having a predetermined analyte concentration;

(b) providing an analyte concentration sensor having a distal analyte responsive portion configured for positioning within said bloodstream and responsive to the presence of analyte to provide sensor outputs corresponding with the sensed concentration of analyte;

(c) providing a delivery assembly having a delivery channel with an input coupled in fluid flow communication with said source of analyte-containing fluid and an output configured for positioning within the bloodstream;

(d) positioning said analyte concentration sensor distal analyte responsive portion and said delivery assembly output within said bloodstream;

(e) delivering said analyte-containing fluid from said source into said delivery channel at a time of delivery, a mass flow rate and over an infusion interval;

(f) deriving a sequence of time associated analyte concentration values from said sensor outputs;

(g) monitoring said sequence of time associated analyte concentration values and identifying a sequence thereof rising in value to a peak defining inflection value and descending in value therefrom;

(h) deriving a value for a select one of said hemodynamic parameters by correlating said sequence of time associated concentration values, said mass flow rate, said infusion interval and said predetermined analyte concentration; and wherein:
said step (d) includes the step of:
(d1) prior to said step (e) deriving from said analyte concentration sensor outputs a baseline value corresponding with the concentration of said analyte in said bloodstream;
said step (h) further correlates said baseline value to derive a said select one of said hemodynamic parameters; and
said step (h) derives a value for cardiac output as said select one of said hemodynamic parameters by correlating said baseline value for concentration of said analyte, said mass flow rate, said predetermined analyte concentration and said identified peak-defining inflection value.

92. The method for determining hemodynamic parameters of a cardiovascular system wherein blood within a bloodstream is circulated to peripheral regions of the body and exhibits a pH value, comprising the steps of:

(a) providing a source of analyte-containing fluid biocompatible with and metabolizable within said body and having a predetermined analyte concentration;

(b) providing an analyte concentration sensor having a distal analyte responsive portion configured for positioning within said bloodstream and responsive to the presence of analyte to provide sensor outputs corresponding with the sensed concentration of analyte;

(c) providing a delivery assembly having a delivery channel with an input coupled in fluid flow communication with said source of analyte-containing fluid and an output configured for positioning within the bloodstream;

(d) positioning said analyte concentration sensor distal analyte responsive portion and said delivery assembly output within said bloodstream;

(e) delivering said analyte-containing fluid from said source into said delivery channel at a time of delivery, a mass flow rate and over an infusion interval;

(f) deriving a sequence of time associated analyte concentration values from said sensor outputs;

(g) monitoring said sequence of time associated analyte concentration values and identifying a sequence thereof rising in value to a peak defining inflection value and descending in value therefrom;

(h) deriving a value for a select one of said hemodynamic parameters by correlating said sequence of time associated concentration values, said mass flow rate, said infusion interval and said predetermined analyte concentration; and wherein:
said step (d) includes the step of:
(d1) prior to said step (e) deriving from said analyte concentration sensor outputs a baseline value corresponding with the concentration of said analyte in said bloodstream;
said step (h) further correlates said baseline value to derive said select one of said hemodynamic parameters; and
said step (h) derives a value for cardiac output as said select one of said hemodynamic parameters correlating said baseline value for concentration of said analyte, said mass flow rate, said predetermined analyte concentration, said infusion interval and an integrated value of said time associated concentration values.

93. The method for determining hemodynamic parameters of a cardiovascular system wherein blood within a bloodstream is circulated to peripheral regions of the body and exhibits a pH value, comprising the steps of:

(a) providing a source of analyte-containing fluid biocompatible with and metabolizable within said body and having a predetermined analyte concentration;

(b) providing an analyte concentration sensor having a distal analyte responsive portion configured for positioning within said bloodstream and responsive to the presence of analyte to provide sensor outputs corresponding with the sensed concentration of analyte;

(c) providing a delivery assembly having a delivery channel with an input coupled in fluid flow communication with said source of analyte-containing fluid and an output configured for positioning within the bloodstream;

(d) positioning said analyte concentration sensor distal analytic responsive portion and said delivery assembly output within said bloodstream;

(e) delivering said analyte-containing fluid from said source into said delivery channel at a time of delivery, a mass flow rate and over an infusion interval;

(f) deriving a sequence of time associated analyte concentration values from said sensor outputs;

(g) monitoring said sequence of time associated analyte concentration values and identifying a sequence thereof rising in value to a peak defining inflection value and descending in value therefrom;

(h) deriving a value for a select one of said hemodynamic parameters by correlating said sequence of time associated concentration values, said mass flow rate, said infusion interval and said predetermined analyte concentration; and wherein:
said step (d) is carried out by positioning said analyte concentration sensor distal analyte responsive portion and said delivery assembly output within said bloodstream at said peripheral region.

94. The method for determining hemodynamic parameters of a cardiovascular system wherein blood within a bloodstream is circulated to peripheral regions of the body and exhibits a pH value, comprising the steps of:

(a) providing a source of analyte-containing fluid biocompatible with and metabolizable within said body and having a predetermined analyte concentration;

(b) providing an analyte concentration sensor having a distal analyte responsive portion configured for positioning within said bloodstream and responsive to the presence of analyte to provide sensor outputs corresponding with the sensed concentration of analyte;

(c) providing a delivery assembly having a delivery channel with an input coupled in fluid flow communication with said source of analyte-containing fluid and an output configured for positioning within the bloodstream;

(d) positioning said analyte concentration sensor distal analyte responsive portion and said delivery assembly output within said bloodstream;

(e) delivering said analyte-containing fluid from said source into said delivery channel at a time of delivery, a mass flow rate and over an infusion interval;

(f) deriving a sequence of time associated analyte concentration values from said sensor outputs;

(g) monitoring said sequence of time associated analyte concentration values and identifying a sequence thereof rising in value to a peak defining inflection value and descending in value therefrom;

(h) deriving a value for a select one of said hemodynamic parameters by correlating said sequence of time associated concentration values, said mass flow rate, said infusion interval and said predetermined analyte concentration; and wherein:
said select one of said hemodynamic parameters is total circulating blood volume; and said step (h) correlates said time of delivery and said time associated concentration values descending in value to derive a maximum increase value for said analyte within said bloodstream and correlates said maximum increase value with a dose value corresponding with said predetermined analyte concentration, said infusion interval and said mass flow rate to derive said total circulating blood volume.

* * * * *